(12) United States Patent
Gieffers et al.

(10) Patent No.: US 10,428,154 B2
(45) Date of Patent: Oct. 1, 2019

(54) MONOCLONAL ANTI-CD95L ANTIBODY

(71) Applicant: Apogenix AG, Heidelberg (DE)

(72) Inventors: Christian Gieffers, Dossenheim (DE);
Oliver Hill, Neckarsteinach (DE);
Meinolf Thiemann, Schriesheim (DE);
Jaromir Sykora, Heppenheim (DE);
Christian Merz, Neckarsteinach (DE);
Tim Schnyder, Igersheim (DE);
Harald Fricke, Mannheim (DE)

(73) Assignee: Apogenix AG, Heidelberg (DE)

( * ) Notice: Subject to any disclaimer, the term of this patent is extended or adjusted under 35 U.S.C. 154(b) by 0 days.

(21) Appl. No.: 15/927,255

(22) Filed: Mar. 21, 2018

(65) Prior Publication Data

US 2018/0208664 A1 Jul. 26, 2018

Related U.S. Application Data

(63) Continuation of application No. PCT/EP2016/072757, filed on Sep. 23, 2016.

(30) Foreign Application Priority Data

Sep. 23, 2015 (EP) .................................... 15186468

(51) Int. Cl.
*C07K 16/28* (2006.01)

(52) U.S. Cl.
CPC ...... *C07K 16/2875* (2013.01); *C07K 2317/21* (2013.01); *C07K 2317/24* (2013.01); *C07K 2317/34* (2013.01); *C07K 2317/55* (2013.01); *C07K 2317/565* (2013.01); *C07K 2317/622* (2013.01); *C07K 2317/76* (2013.01); *C07K 2317/92* (2013.01)

(58) Field of Classification Search
CPC ............ C07K 16/2875; C07K 2317/21; C07K 2317/24; C07K 2317/34; C07K 2317/55; C07K 2317/565; C07K 2317/622; C07K 2317/76; C07K 2317/92
See application file for complete search history.

(56) References Cited

U.S. PATENT DOCUMENTS 6,946,255 B1 9/2005 Kayagaki et al.

FOREIGN PATENT DOCUMENTS

| EP | 0842948 A1 | 5/1998 |
| EP | 0957166 A1 | 11/1999 |
| WO | 2010066914 A2 | 6/2010 |

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
Lloyd C., et al. (2009). Protein Engineering, Design & Selection. 22(3):159-168. (doi:10.1093/protein/gzn058. Published online Oct. 29, 2008).*
Edwards, BM., et al. (2003). J. Mol. Biol. 334:103-118. (doi:10.1016/j.jmb.2003.09.054).*
Nisihara T et al., "Humanization and epitope mapping of neutralizing anti-human Fas ligand monoclonal antibodies: structural insights into Fas/Fas ligand interaction", The Journal of Immunology, The American Association of Immunologists, US, vol. 167, No. 6, Sep. 15, 2001 (Sep. 15, 2001), pp. 3266-3275.
P. Schneider et al.: "Characterization of Fas (Apo-1, CD95)-Fas Ligand Interaction", Journal of Biological Chemistry, vol . 272, No. 30, Jul. 25, 1997 (Jul. 25, 1997), pp. 18827-18833.
International Search Report dated Aug. 12, 2016 for PCT/EP2016/072757.

* cited by examiner

*Primary Examiner* — Robert S Landsman
(74) *Attorney, Agent, or Firm* — Perkins Coie LLP; Viola T. Kung

(57) ABSTRACT

The present invention relates to a specific CD95L antibody and to the use thereof in the treatment or diagnosis of diseases involving CD95L-induced signalling, e.g. cancer diseases.

10 Claims, 21 Drawing Sheets

Figure 2A:
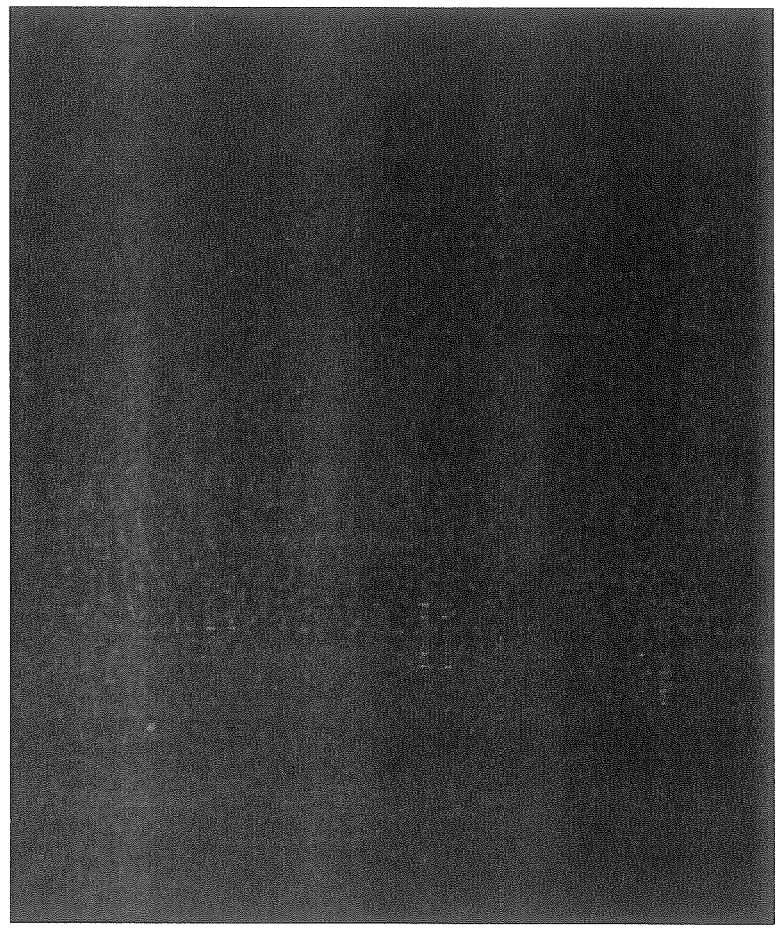

Specification includes a Sequence Listing.

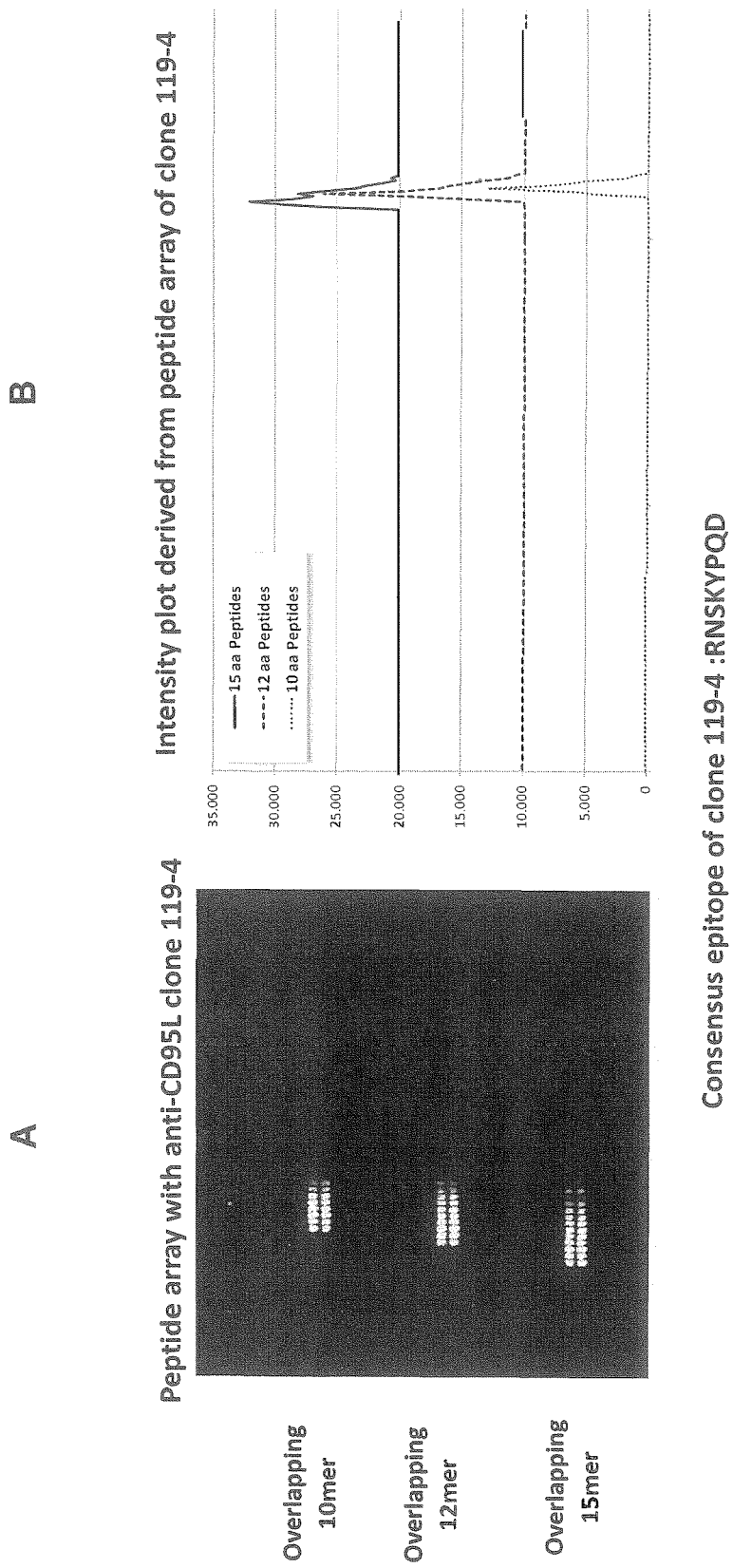

Figure 16
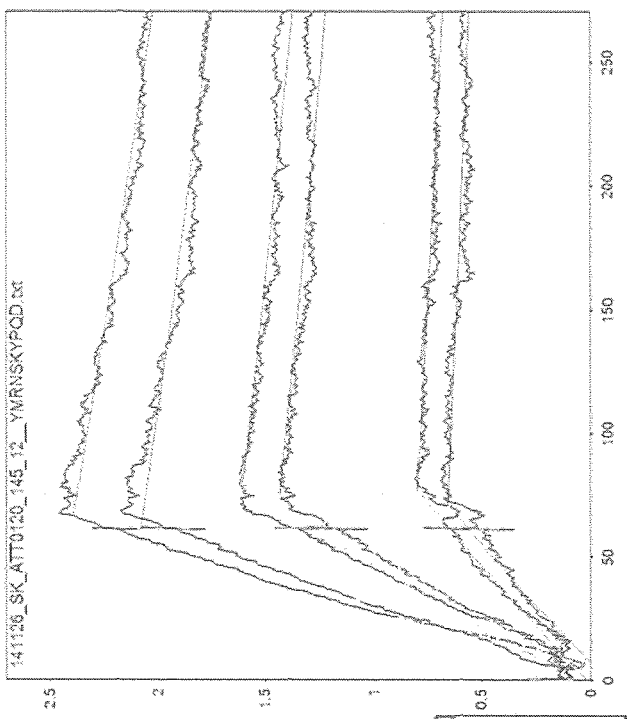
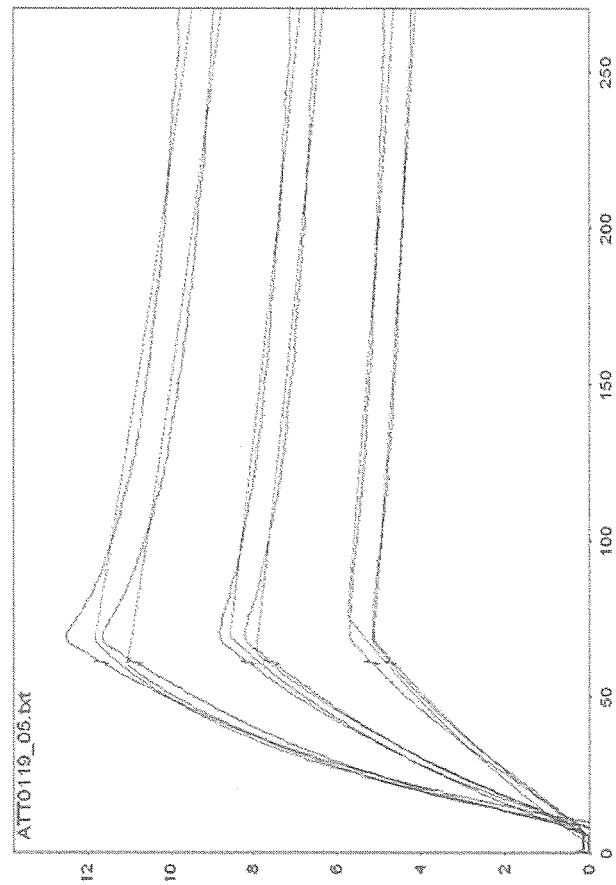
Calculation of KD for shown sensograms
QCM: Immobilized Peptide
119-4: BSA-C-YMRNSKYPQD
145-12: BSA-C-YMRNSKYPQD
| | $k_{on}$ | $k_{off}$ | $k_D$ [mol] | $k_D$ [nmol] |
|---|---|---|---|---|
| 119-4 | $9{,}17e^{+5}$ | $1{,}098e^{-3}$ | $1{,}20e^{-9}$ | 1,20 |
| 145-12 | $1{,}14e^{+5}$ | $8{,}26e^{-4}$ | $7{,}22e^{-9}$ | 7,22 |

Figure 17

Alignment of humanized variable heavy (VH) domains of clone 145-12 and human VH consensus framework

```
                                                          H28           H31a
           1
hum III    EVQLVESGGGLVQPGGSLRLSCAASGFTFS[SYAMS ]WVRQA
huVH145_A  EVQLVESGGGLVQPGGSLRLSCAASGFsFS[SGYDMC]WVRQA
huVH145_B  EVQLVESGGGLVQPGGSLRLSCAASGFsFS[SGYDMC]WVRQA
huVH145_C  EVQLVESGGGLVQPGGSLRLSCAASGFsFS[SGYDMs]WVRQA H50                                    H71
Hum III    PGKGLEWVA[VISGDGGSTYYADSVKG]RFTISRDNSKNTLYL
huVH145_A  PGKGLEWVA[CIDTDNDATYYASWAKG]RFTISkDsSKNTLYL
hu145-12B  PGKGLEWVA[CIDTDNDATYYAdsvKG]RFTISkDsSKNTLYL
hu145-12C  PGKGLEWVs[aIDTDNDATYYAdsvKG]RFTISkDsSKNTLYL Hum III    QMNSLRAEDTAVYYCAR[GRVGYSLYDY]WGQGTLVTVSS
huVH145_A  QMNSLRAEDTAVYYCAR[THGDYVAFKL]WGQGTLVTVSS
huVH145_B  QMNSLRAEDTAVYYCAR[THGDYVAFKL]WGQGTLVTVSS
huVH145_C  QMNSLRAEDTAVYYCAR[THGDYVAFKL]WGQGTLVTVSS
```

Figure 18

Alignment of humanized variable heavy (VH) domains of clone 119-4 and human VH consensus framework

```
                                                         H28              H35a
          1
hum III   EVQLVESGGGLVQPGGSLRLSCAASGFTFS[SYAMS  ]WVRQA
huVH119_A EVQLVESGGGLVQPGGSLRLSCAASGFsFS[DHYWMC]WVRQA
huVH119_B EVQLVESGGGLVQPGGSLRLSCAASGFsFS[DHYWMC]WVRQA
huVH119_C EVQLVESGGGLVQPGGSLRLSCAASGFsFS[DHYWMs]WVRQA H50                                  H71
Hum III   PGKGLEWVA[VISGDGGSTYYADSVKG]RFTISRDNSKNTLYL
huVH119_A PGKGLEWVA[CIYTADSDSYYASWAKG]RFTISkDsSKNTLYL
huVH119_A PGKGLEWVA[CIYTADSDSYYAdsVKG]RFTISkDsSKNTLYL
huVH119_A PGKGLEWVs[aIYTADSDSYYAdsVKG]RFTISkDsSKNTLYL Hum III   QMNSLRAEDTAVYYCAR[ GRVGYSLYDY  ]WGQGTLVTVSS
huVH119_A QMNSLRAEDTAVYYCAR[NGAYAGGPYGDL]WGQGTLVTVSS
huVH119_B QMNSLRAEDTAVYYCAR[NGAYAGGPYGDL]WGQGTLVTVSS
huVH119_C QMNSLRAEDTAVYYCAR[NGAYAGGPYGDL]WGQGTLVTVSS
```

Figure 19

Alignment of humanized variable light (VL) domains of clone 119-4 and clone 45-12 and human VL consensus framework

```
            1
hu_K1     DIQMTQSPSSLSASVGDRVTITC[RASQSISNYLA  ]WYQQK
hu119_4   DIQMTQSPSSLSASVGDRVTITC[KASQSIRTSLV  ]WYQQK
hu145_12  DIQMTQSPSSLSASVGDRVTITC[QSSQSVYKNNDLS]WYQQK hu_K1     PGKAPKLLIY[AASSLES ]GVPSRFSGSGSGTDFTLTISSLQP
hu119_4   PGKAPKLLIY[KASDLPS ]GVPSRFSGSGSGTDFTLTISSLQP
hu145_12  PGKAPKLLIY[QASKLAS ]GVPSRFSGSGSGTDFTLTISSLQP hu_K1     EDFATYYC[QQYNSLPWT        ]FGQGTKVEIKR
hu119_4   EDFATYYC[QSYDFRDTINNGHS]FGQGTKVEIKR
hu145_12  EDFATYYC[AGGYTASIYA     ]FGQGTKVEIKR
```

MONOCLONAL ANTI-CD95L ANTIBODY

This application is a continuation of PCT/EP2016/072757, filed Sep. 23, 2016; which claims the priority of EP 15186468.3, filed Sep. 23, 2015. The contents of the above applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Mar. 19, 2018, and a size of 96.5 kilobytes. The Sequence Listing filed via EFS-Web is part of the specification and is hereby incorporated in its entirety by reference herein.

DESCRIPTION

The present invention relates to a specific CD95L antibody and to the use thereof in the treatment or diagnosis of diseases involving CD95L induced signalling, e.g. cancer disease.

The field of the present invention can be seen in particular in the improvement of cancer therapy and cancer diagnostic.

The present invention provides a monoclonal antibody that specifically binds to a linear epitope of CD95L and is capable to inhibit CD95L induced signalling. It was surprisingly found, that the antibody of the invention inhibits signalling induced by CD95/CD95L with higher efficacy than previously known antagonists of CD95/CD95L, in particular other anti-CD95L antibodies, soluble CD95 molecules or fusion proteins like APG101.

Thus, a first aspect of the invention is a monoclonal anti-CD95L antibody specifically binding to an epitope of human CD95L comprising the amino acid sequence NSKYP.

The binding epitope comprises the amino acid sequence RNSKYP, preferably RNSKYPQ, which is found in CD95L of many different species. Preferably, the antibody binds to a linear epitope of CD95L comprising the amino acid sequence RNSKYPQD and/or RNSKYPED. Human CD95L as well as CD95L from monkeys, e.g. *Macaca fascicularis*, comprises the epitope RNSKYPQD, while mouse CD95L from *Mus musculus* comprises the epitope RNSKYPED. According to a preferred aspect of the invention, the antibody is capable to specifically bind to CD95L derived from different species, e.g. human, monkey and mouse. It is preferred that the antibody specifically binds to human, and at least one of monkey (e.g. *Macaca fascicularis*) and mouse (*Mus musculus*) CD95L, more preferably to human, monkey and mouse CD95L.

The term "antibody" particularly refers to molecules comprising at least one immunoglobulin heavy chain and at least one immunoglobulin light chain. Each heavy and light chain may comprise a variable and a constant domain. The antigen binding site may be formed from the variable domains of a heavy chain and a light chain. A variable region (also referred to as variable domain) comprises complementarity determining regions (CDRs), e.g., a CDR1, a CDR2 and a CDR3 region and framework regions (FRs) flanking the CDRs.

The term "complementarity determining region" is readily understood by the skilled person (see, e.g., Harlow and Lane (EDS.), Antibodies: A Laboratory Manual, CSHL Press, Cold Spring Harbour, N.Y., 1988) and refers to the stretches of amino acids within the variable domain of an antibody that primarily make contact with the antigen and determine antibody specificity. This region is also known as the hypervariable region.

The present invention encompasses both full length immunoglobulin and functional immunoglobulin fragments like Fab, Fab', F(ab')2 fragments, Fv fragments, diabodies, single-chain antibody molecules and single-domain antibodies. Also other fragments are included as long as they exhibit the desired capability of binding to an epitope comprising amino acids 214-219 of human CD95L, comprising the amino acid sequence "RNSKYP", preferably amino acids 214-220, comprising the amino acid sequence "RNSKYPQ" and most preferably amino acids 214-221, comprising the amino acid sequence "RNSKYPQD". For a review of certain antibody fragments, see Hudson et al., Nat. Met. 9: 129-134 (2003).

"Diabodies" are antibody fragments with two antigen-binding sites that may be bivalent or bispecific (see, e.g., Hudson et al., 2003). "Single-chain antibodies" are antibody fragments comprising all or a portion of the heavy chain variable domain, or all or a portion of the light chain variable domain of an antibody. Antibody fragments can be made by various techniques, including but not limited to proteolytic digestion of an intact antibody as well as production by recombinant hosts (e.g., *E-coli* or phage) as described herein.

Also encompassed by the present invention are human antibodies. The term "human antibody" is meant to encompass any fully human or humanized antibodies. Human antibodies may be prepared from genetically engineered animals, e.g., animals comprising a xenogeneic immune system or from antibody display libraries according to known techniques. Human antibodies are described generally in Van Dijk and Van De Winkel (Car. Opin. Pharmacol. 5: 368-74 (2001)) and Lonberg (Car. Opin. Immunol. 20: 450-459 (2008)).

Humanized antibodies may be prepared by humanization of monoclonal antibodies derived from other species (e.g. mouse, rat, rabbit) according to known techniques. Typically, a non-human antibody is humanized to reduce immunogenicity to humans, while retaining the specificity and affinity of the parental non-human antibody. Humanized antibodies and methods of making them are reviewed, e.g. in Alamagro and Fransson, *Front. Biosci.* 13: 1619-1633 (2008).

The antibodies of the present invention are characterized in that they specifically bind to an epitope of CD95L comprising the amino acid sequence RNSKYP, preferably RNSKYPQ and more preferably RNSKYPQD of human CD95L. This binding epitope has been shown to be unique for its suitability to inhibit CD95L-induced signalling. Antibodies binding to this epitope directly compete with the binding of CD95L to the CD95 receptor. Next to apoptosis, the corresponding receptor CD95 mediates, depending on the tissue and condition non-apoptotic signals (such as NF-kB, MAPK or PI3K), that promote inflammation, contribute to carcinogenesis and modulate immunoncological parameters (e.g. tumour infiltrating T-cell populations). All of these activities are potentially inhibited by antibodies described herein.

The term "bind" or "binding" of an antibody means an at least temporary interaction or association with or to a target antigen, i.e. human CD95L comprising fragments thereof containing an epitope described herein. In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g. $10^{-9}$ M to $10^{13}$M). Methods for determining the Kd value are known to the person skilled in the art.

In one embodiment, Kd is measured by a radio-labelled antigen binding assay (Radioimmunoassay, RIA) performed with the Fab version of an antibody of interest and its antigen.

According to another embodiment, Kd is measured using surface plasmon resonance assays with immobilized antigen. According to another embodiment Kd is measured by a quartz crystal microbalance (QCM) with immobilized antigen. According to a preferred embodiment of the present invention, the antibodies are human monoclonal antibodies directed against an epitope of human CD95L as described herein.

The antibodies of the invention may be of various immunoglobulin (Ig) types, for example of the IgA-, IgD-, IgE-, IgG- or IgM-type, preferably of the IgG- or IgM-type including but not limited to the IgG1-, IgG2-, IgG3-, IgG4-, IgM1 and IgM2-type. In one preferred embodiment the antibody is of the IgG1 type.

Preferably, the antibodies of the invention are monoclonal antibodies.

In certain embodiments of the present invention, the antibody may comprise specific heavy chain complementarity determining regions CDRH1, CDRH2 and/or CDRH3. The CDR sequences described herein are numbered using the Kabat scheme.

In one embodiment, the antibody comprises a heavy chain comprising:

a heavy chain complementarity determining region 1 (CDRH1) having the amino acid sequence as shown in SEQ ID NO: 1 or 11, a heavy chain complementarity determining region 2 (CDRH2) having the amino acid sequence as shown in SEQ ID NO: 2 or 12, and/or a heavy chain complementarity determining region 3 (CDRH3) having the amino acid sequence as shown in SEQ ID NO: 3 or 13.

The antibody according to the invention may also comprise specific light chain complementarity determining regions CDRL1, CDRL2 and/or CDRL3. Accordingly, in one embodiment, the antibody comprises a light chain comprising:

a light chain complementarity determining region 1 (CDRL1) having the amino acid sequence as shown in SEQ ID NO: 4 or 14, a light chain complementarity determining region 2 (CDRL2) having the amino acid sequence as shown in SEQ ID NO: 5 or 15, and/or a light chain complementary determining region 3 (CDRL3) having the amino acid sequence as shown in SEQ ID NO: 6 or 16.

In a preferred embodiment, the antibody comprises a specific combination of CDRs within one heavy chain and/or within one light chain. Accordingly, a particularly preferred antibody of the present invention comprises a heavy chain including a CDRH1 as shown in SEQ ID NO: 1 or 11,
    a CDRH2 as shown in SEQ ID NO: 2 or 12, and
    a CDRH3 as shown in SEQ ID NO: 3 or 13, and
a light chain including
    a CDRL1 as shown in SEQ ID NO: 4 or 14,
    a CDRL2 as shown in SEQ ID NO: 5 or 15, and
    a CDRL3 as shown in SEQ ID NO: 6 or 16.

Preferred is an antibody comprising a heavy chain comprising CDRH1 as shown in SEQ ID NO: 1, CDRH2 as shown in SEQ ID NO: 2 and CDRH3 as shown in SEQ ID NO: 3 and a light chain comprising CDRL1 as shown in SEQ ID NO: 4, CDRL2 as shown in SEQ ID NO: 5 and CDRL3 as shown in SEQ ID NO: 6.

Also preferred is an antibody comprising a heavy chain comprising CDRH1 as shown in SEQ ID NO: 11, CDRH2 as shown in SEQ ID NO: 12 and CDRH3 as shown in SEQ ID NO: 13 and a light chain comprising CDRL1 as shown in SEQ ID NO: 14, CDRL2 as shown in SEQ ID NO: 15 and CDRL3 as shown in SEQ ID NO: 16.

In a preferred embodiment of the invention, the anti-CD95L antibody comprises a heavy chain variable region (VH) as shown in SEQ ID NO: 7 or 17 or a sequence having a sequence identity of at least 90% over the whole heavy chain variable region, preferably at least 95% sequence identity, more preferably at least 96%, 97%, 98% or 99% sequence identity. Furthermore, the antibody of the invention preferably comprises a light chain variable region (VL) as shown in SEQ ID NO: 8 or 18 or a sequence having a sequence identity of at least 90% over the whole light chain variable region, preferably at least 95% sequence identity, more preferably at least 96%, 97%, 98% or 99% sequence identity. Particularly preferred are antibodies comprising a heavy chain variable region as shown in SEQ ID NO: 7 or 17 and a light chain variable region as shown in SEQ ID NO: 8 or 18.

Preferably, an antibody of the invention comprises a heavy chain variable region as shown in SEQ ID NO: 7 and a light chain variable region as shown in SEQ ID NO: 8 or a heavy chain variable region as shown in SEQ ID NO: 17 and a light chain variable region as shown in SEQ ID NO: 18.

According to a particularly preferred embodiment of the invention, the antibody of the invention comprises a heavy chain comprising the amino acid sequence as shown in SEQ ID NO: 9 or 19, or an amino acid sequence having a sequence identity of at least 90% thereto over the whole heavy chain amino acid sequence, and a light chain comprising an amino acid sequence as shown in SEQ ID NO: 10 or 20, or an amino acid sequence having a sequence identity of at least 90% thereto over the whole length of the light chain amino acid sequence. The sequence identity of the heavy chain and the light chain amino acid sequence is preferably at least 95%, more preferably at least 96%, 97%, 98% or 99% to the sequences shown in SEQ ID NO: 9, 10, 19 and 20. Most preferred is an antibody comprising the heavy chain amino acid sequence as shown in SEQ ID NO: 9 and the light chain amino acid sequence as shown in SEQ ID NO: 10 as well as an antibody comprising the heavy chain amino acid sequence as shown in SEQ ID NO: 19 and the light chain amino acid sequence as shown in SEQ ID NO: 20.

Preferred Humanized Antibodies of the Invention

To determine the epitope on human CD95L recognized by the antibody, chemically prepared arrays of short peptides derived from the amino acid sequence of human CD95L can be used to locate and identify antibody epitopes (Reinike W., Methods Mol. Biol., 2004, 248: 443-63). A further method to map the epitopes in human CD95L bound by the antibodies of the invention comprises Snaps/SELDI (Wang et al., Int. J. Cancer, 2001, June 15, 92(6): 871-6) or a routine cross-blocking assay such as described in *Antibodies, A Laboratory Manual*, Cold Spring Harbor Laboratory, Ed Harlow and David Lane (1988) can be performed.

As mentioned above, the antibodies of the invention show advantageous properties with respect to their binding specificity and biological activity, in particular with respect to their capability to inhibit CD95L-induced signalling.

The antibodies of the present invention may be coupled to a heterologous group, e.g., a label or an effector group.

An antibody conjugate comprising an antibody of the invention coupled to an effector group is particularly suitable for therapeutic applications. As used herein, the term "effector group" refers to a therapeutic group, a toxin, a cytotoxic group, an antigen or other effector group known in the art.

An antibody conjugate comprising an antibody of the invention coupled to a label group is particularly suitable for diagnostic applications. As used herein, the term "label group" refers to a detectable marker, e.g., a radiolabelled amino acid or biotin moiety, a fluorescent marker, an enzyme or any other type of marker which is known in the art.

The invention also relates to a nucleic acid molecule encoding the antibody as disclosed above. The term "nucleic acid molecule" encompasses DNA, e.g., single- or double-stranded DNA or RNA. The DNA may be of genomic, cDNA or synthetic origin, or a combination thereof. The nucleic acid molecule of the invention may be in operative linkage to an expression control sequence, i.e. to a sequence which is necessary to effect the expression of coding nucleic acid sequences. Such expression control sequences may include promoters, enhancers, ribosomal binding sites and/or transcription termination sequences. Specific examples of suitable expression control sequences are known in the art.

According to a preferred embodiment, the invention is directed to an isolated nucleic acid molecule comprising a nucleic acid sequence selected from the group consisting of
  (a) a nucleic acid sequence encoding an antibody, or a functional fragment thereof as defined above,
  (b) a nucleic acid sequence complementary to any one of the sequences in (a), and
  (c) a nucleic acid sequence capable of hybridizing to (a) or (b) under stringent conditions.

According to a particularly preferred embodiment of the invention, a nucleic acid molecule comprises a sequence encoding the amino acid sequence of the variable region of the heavy chain and a sequence encoding the amino acid sequence of the variable region of the light chain of the antibody. In an alternative embodiment, a combination of two nucleic acid molecules is provided, wherein one nucleic acid molecule encodes the amino acid sequence of the light chain of the antibody and the other nucleic acid molecule encodes the amino acid sequence of the heavy chain of the antibody. A preferred nucleic acid molecule of the invention is an isolated nucleic acid molecule comprising a nucleic acid sequence as shown in any one of SEQ ID NOs: 21-24. For example, an isolated nucleic acid molecule may comprise the nucleic acid sequences as shown in SEQ ID NOs: 21 and 22 or the nucleic acid sequences as shown in SEQ ID NOs: 23 and 24.

The term "hybridizing under stringent conditions" means that two nucleic acid fragments hybridize with one another under standardized hybridization conditions as described, for example in Sambrook et al., "*Expression of cloned Genes in E. coli*" in *Molecular Cloning: A Laboratory Manual* (1989), Cold Spring Harbor Laboratory Press, New York, USA. Such conditions are, for example, hybridization in 6.0×SSC (Saline Sodium Citrate) at about 45° C. followed by a washing step with 2.0×SSC at 50° C., preferably 2.0×SSC at 65° C. or 0.2×SSC at 50° C., preferably 0.2×SSC at 65° C.

The nucleic acid molecule of the invention may be located on a vector which may additionally contain a replication origin and/or a selection marker gene. Examples of vectors are e.g. plasmids, cosmids, phages, viruses etc. Thus, a further embodiment of the invention is a vector comprising a nucleic acid sequence as disclosed herein. Preferably, the vector is an expression vector. Said vector may, for example, be a phage, plasmid, viral or retro viral vector. Retro viral vectors may be replication competent or replication defective. In the latter case, viral propagation generally will occur only in complementing hosts/cells.

The nucleic acid molecules of the invention may be joined to a vector containing selectable markers for propagation in a host. Generally, a plasmid vector is introduced in a precipitate such as a calcium phosphate precipitate or rubidium chloride precipitate or in a complex with a charged lipid or in carbon-based clusters such as fullerenes. Should the vector be a virus, it may be packed in vitro using an appropriate packaging cell line prior to application to host cells.

Preferably, the vector of the invention is an expression vector, wherein the nucleic acid molecule is operatively linked to one or more control sequences allowing the transcription and optionally expression in prokaryotic and/or eukaryotic host cells. Expression of said nucleic acid molecule comprises transcription of the nucleic acid molecule, preferably into a translatable mRNA. Regulatory elements ensuring expression in eukaryotic cells, preferably mammalian cells, are well-known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Expression vectors derived from viruses such as retrovirus, vaccina virus, adeno-associated virus, herpes virus or bovine papilloma virus may be used for delivery of the polynucleotides or vector of the invention into targeted cell population. Methods which are well-known to those skilled in the art can be used to construct recombinant viral vectors; see for example the techniques described in Sambrook, *Molecular Cloning, A Laboratory Manual*, Cold Spring Harbor Laboratory Press (2001, 3$^{rd}$ edition), N.Y. and Ausubel, *Current Protocols in Molecular Biology*, Green Publishing Associates and Wiley Interscience, N.Y. (1994). Alternatively, the nucleic acid molecules of the invention can be reconstituted into liposomes for delivery to target cells.

Further, the invention refers to a host which comprises the nucleic acid molecule or the vector as described above. The nucleic acid molecule or the vector may be introduced into the host by transformation, transfection or transduction according to any method known in the art.

Said host may be a prokaryotic or eukaryotic cell or a non-human transgenic animal. The nucleic acid or vector of the invention which is present in the host may either be integrated into the genome of the host or it may be maintained extrachromosomally. In this respect, it is also to be understood that the nucleic acid molecule of the invention can be used for "gene targeting" and/or "gene replacement", for restoring a mutant gene or for creating a mutant gene via homologous recombination; see for example Mouellic, *Proc. Natl. Acad. Sci. USA*, 87 (1990), 4712-4716; Joyner, *Gene Targeting, A Practical Approach*, Oxford University Press.

The host can be any prokaryotic or eukaryotic cell such as a bacterial, insect, fungal, plant, animal, mammalian or preferably a human cell. The transformed hosts can be grown in fermenters and cultured according to techniques known in the art to achieve optimal cell growth. The antibodies, antibody fragments or derivatives thereof of the invention can then be isolated from the growth medium, cellular lysates or cellular membrane fractions. The isolation and purification of the microbially or otherwise expressed antibodies, antibody fragments or derivatives thereof of the invention may be by any conventional means, such as for example preparative chromatographic separations and immunological separations such as those involving the use of monoclonal or polyclonal antibodies.

According to one embodiment of the invention, the host is a human, bacteria, animal, fungal, amphibian or plant cell. Preferred animal cells include but are not limited to Chinese hamster ovary (CHO) cells, baby hamster kidney (BHK) cells, monkey kidney cells (COS), mouse embryonic fibroblast cells (NIH-3T3) and a number of other cell lines, including human cells. In a particularly preferred embodiment, said animal cell is a CHO cell.

In a particularly preferred embodiment, said animal cell is a rabbit cell. Preferred insect cells include but are not limited to cells from the SF9 cell lines.

The antibody of the invention may be prepared by a method, wherein said antibody is obtained from a host as described herein above. Thus, a further embodiment of the present invention is a method for the preparation of an antibody comprising culturing the host cell of the invention under conditions that allow synthesis of said antibody and recovering said antibody from said culture.

The transformed hosts can be grown in fermenters and cultured according to techniques known to those skilled in the art to achieve optimal cell growth. In addition, efficient expression and processing of newly synthetized protein may depend on the presence of further amino acid domains like signal peptides. In a further embodiment, antibodies of the invention may comprise an N-terminal signal sequence, which allows secretion from a host cell after recombinant expression. Although signal peptides are heterogeneous, and many prokaryotic and eukaryotic signal peptides are functionally interchangeable, the skilled person is aware of means to choose a suitable signal peptide according to the used expression system. Therefore, as a non-limiting example reference is made to the signal peptide of SEQ ID NO: 52. Once expressed, the whole antibodies, their dimers, individual light and heavy chains, or other immunoglobulin forms of the present invention can be purified according to standard procedures of the art, including ammonium sulphate precipitation, affinity columns, column chromatography, gel electrophoresis and the like; see Scopes, "*Protein Purification*", Springer-Verlag, N. Y. (1982). The antibody or its corresponding immunoglobulin chain(s) of the invention can then be isolated from the growth medium, cellular lysates or cellular membrane fractions. The isolation and purification of the e.g. microbially expressed antibodies or immunoglobulin chains of the invention may be by any conventional means, such as for example preparative chromatographic separations and immunological separations such as those involving the use of monoclonal or polyclonal antibodies directed e.g. against the constant region of the antibody of the invention.

It will be apparent to those skilled in the art that the antibodies of the invention can be further coupled to other moieties, e.g. drug targeting and imaging applications, i.e. effector or labelling groups as defined herein. Such coupling may be conducted chemically after expression of the antibody or antigen to side of attachment or the coupling product may be engineered into the antibody or antigen of the invention at the DNA level. The DNAs are then expressed in a suitable host system, and the expressed proteins are collected and renatured if necessary.

According to one embodiment, a recombinant cell as described above is cultured under conditions which allow expression of the antibody encoding nucleic acid molecules. The antibody may be collected from the cultured cell or the culture supernatant. Preferably, the antibody is prepared from a mammalian, particularly from a human cell. In another preferred embodiment the antibody is prepared from CHO cells.

Still a further aspect of the present invention relates to a pharmaceutical composition comprising the antibody as described above, optionally together with a pharmaceutically acceptable carrier. According to the invention, the pharmaceutical composition is adapted for a therapeutic use.

The term "carrier" includes agents, e.g. diluents, stabilizers, adjuvants or other types of excipients that are non-toxic to the cell or mammal being exposed thereto at the dosages and concentrations employed. Examples of pharmaceutically acceptable carriers are well-known in the art and include phosphate-buffered saline solutions, water, emulsions such as oil/water emulsions, various types of wetting agents, sterile solutions, etc. Preferred examples of physiologically acceptable carriers include buffers such as phosphate, citrate and other organic acids (however, with regard to the formulation of the present invention, a phosphate buffer is preferred); anti-oxidants including ascorbic acid, low molecular weight (less than about 10 residues) polypeptides; proteins such as serum albumin, gelatine or immunoglobulins; hydrophilic polymers such as polyvinyl pyrrolidone; amino acids such as glycine, glutamine, asparagine, arginine or lysine; monosaccharides, disaccharides, and other carbohydrates including glucose, mannose or dextrins, chelating agents such as EDTA, sugar, alcohols such as mannitol or sorbitol; salt-forming counter ions such as sodium; and/or non-ionic surfactants such as TWEEN, polyethylene or polyethylene glycol.

The pharmaceutical composition may be formulated by well-known conventional methods, i.e. by mixing the active agent with carriers and optionally other agents that are usually incorporated into the formulation.

Another aspect of the present invention relates to a pharmaceutical composition as described above, which contains at least one further active agent. Which further active agent is used depends on the indication to be treated. For example, cytotoxic agents such as doxorubicin, cisplatin or carboplatin, cytokines or other anti-neoplastic agents may be used in the treatment of cancer. In particular for cancer treatment a combination with known immunotherapeutic agents in preferred. This combination includes but is not limited to agents like: anti PD-1 antibodies, anti-PD-L1 antibodies and anti-CTLA-4 antibodies.

According to a preferred embodiment the monoclonal antibody or the pharmaceutical composition according to the invention can be used to inhibit the CD95 signalling pathway. In particular, the antibody or the composition can be used in the prophylaxis and/or treatment of disorders selected from autoimmune disorders, AIDS, heart disorders, e.g. myocardial infarction, graft-versus-host disorders, transplant rejection, brain damage, e.g. stroke, spinal cord injuries, sepsis, hepatitis, NASH, disorders associated with inflammation, ischemic reperfusion injury and renal disorders. Of course, the composition described herein may be used for the treatment of cancers, preferably solid cancers as well as lymphomas. Solid cancers comprise sarcomas and carcinomas. For example, the cancer to be treated may be colon, lung, breast, pancreas, renal, colorectal, liver or brain cancers, e.g., glioblastomas and/or metastasis thereof. Alternatively, the cancer to be treated may be a cancer of lymphoid or myeloid origin.

A further aspect of the present invention is a method of treatment of cancer, said method comprising administering a monoclonal anti-CD95L antibody of the present invention to a patient. For therapeutic use the CD95L antibody can be administered systemically, for example by infusion or injection.

The therapeutic method of the invention preferably includes a preceding step of determining the expression of CD95L in a cancer sample obtained from a patient. This diagnostic classification of cancer by the extent of CD95L expression enables an adapted therapy for those patients suffering from a cancer expressing CD95L. It is preferred that the monoclonal anti-CD95L antibody of the invention is administered only if expression of CD95L has been detected in the cancer sample. This strategy is advantageous, because the anti-CD95L antibody is administered to those patients only in which a therapeutic success can be expected. This is not disadvantageous in patients suffering from a cancer not expressing CD95L, because these patients will probably not benefit from a treatment with a CD95L inhibitor.

Expression of CD95L can be determined by any know method. For example, CD95L or CD95L mRNA can be determined. A preferred example of a suitable method is a histological, histochemical, immunohistochemical and/or flow cytometry based method. In particular, the expression of CD95L in the cancer sample can be determined by contacting the sample with an agent specifically binding to CD95L. For example, CD95L inhibitors specifically binding to CD95L can be used for determination of CD95L.

Exemplary CD95L inhibitors include antibodies, soluble CD95 molecules, fusion proteins, etc. Suitable antibodies can be prepared by known methods. An example of a suitable antibody is a monoclonal antibody of the invention suitable for detection of CD95L in flow cytometry based analysis. Also preferred are anti-CD95L-specific antibodies or a CD95L-recognizing fragment thereof binding to an intracellular epitope of CD95L. According to an especially preferred embodiment the anti-CD95L-specific antibody or CD95L-recognising fragment thereof binds to tyrosine (Y) in N-terminal position 13 of human CD95L. According to especially preferred embodiments a diagnostic anti-CD95L antibody or a CD95L-recognizing fragment thereof recognizes an epitope that includes the N-terminal amino acids 13-19 of human CD95L. An example of a suitable antibody is described in WO 2014/177576.

According to an especially preferred embodiment of the invention, the antibodies described herein can be used for the determination of CD95L expression in a first step and if CD95L expression is detected, the inventive antibodies can be used for therapeutic purposes in a second step.

In the present invention, expression of CD95L is determined by any known suitable method, but using the antibody of the present invention. For example, the determination may comprise a histological, histochemical immunohistochemical (IHC) or/and flow cytometry based method using the above-described anti-CD95L antibody. Immunohistochemical methods are particularly preferred.

The sample employed in the classification of cancer as described herein can be an archived tumour tissue, for example a biopsy or surgery material embedded in paraffin, which has been obtained in an earlier stage of the disease.

The cancer disease can be classified by the level of CD95L expression into a CD95L positive cancer disease or a CD95L negative cancer disease.

In particular the CD95L positive cancer disease is characterised by a cell expressing CD95L on the cell surface. However, the methods described herein may also be based on the detection of intracellular epitopes of CD95L.

A cancer can be regarded as CD95L positive, if at least 1%, at least 2%, at least 5%, at least 10%, at least 20%, or at least 50% of the cells in a cancer sample express CD95L. The number of CD95L positive cells can be determined by counting the cells in a microscopic section.

CD95L expression is considered to be absent (CD95L negative) if essentially no cells expressing CD95L can be detected in the tissue sample, or if the sample is a sample which does not fulfil the criteria defined herein for a CD95L positive sample (non-positive sample). In a CD95L negative sample, the number of tumour cells expressing CD95L can be below the threshold defined herein for CD95L positive samples, for example below 1%, below 2%, below 3%, below 4%, below 5%, or below 10% of tumour cells.

A cancer can also be regarded as CD95L positive, if CD95L can be detected on at least 1%, at least 2%, at least 5%, at least 10%, at least 20%, or at least 50% of the area of tumour tissue in a tissue section. This value is termed herein as "% CD95L positive area of tumour tissue". Non-tumour tissue is excluded in this analysis. A tissue section can be prepared by known methods. Suitable methods for detection of CD95L are described in WO 2014/177576. An exemplary method and an example for the determination of the area of CD95L positive tumour tissue is given in WO 2014/177576. CD95L expression can be considered to be absent (CD95L negative) if essentially no CD95L can be detected in the tissue sample, or if the value of % CD95L positive area of tumour tissue is below the threshold defined for a CD95 positive sample, for example below 1%, below 2%, below 3%, below 4%, below 5%, or below 10% of tumour area.

CD95L expression (e.g. in terms of cell number or surface in a tissue section) can be determined by known methods, for example by methods based upon automatized analysis of tissue sections.

By the method of the present invention, any type of cancer, in particular solid tumour tissue, can be diagnosed for expression of CD95L. The cancer to be diagnosed or/and treated may also be a cancer of lymphoid or myeloid origin.

Diagnosis based upon the expression of CD95L is of particular importance for diagnosis and treatment of those cancer types which include CD95L expression sub-types, and thus require a specific therapy adapted to the diagnosed CD95L expression sub-type. An example of CD95L expression sub-types of glioblastoma identified in the present invention is CD95L positive glioblastoma and CD95L negative glioblastoma, as described herein. The solution provided herein includes a specific therapy based upon the diagnosis of the CD95L expression sub-types identified in the present invention.

Any type of cancer, in particular solid tumour tissue, can be determined to be CD95L expression positive or CD95L expression negative. The cancer can be characterised by invasive growth. The cancer disease to be diagnosed according to the present invention as CD95L positive cancer or CD95L negative cancer can be selected from the group consisting of brain cancer, colon cancer, colorectal cancer, pancreatic cancer, breast cancer, lung cancer, renal cancer, liver cancer or/and metastatic disease thereof. In particular, the cancer disease is glioma, more particular glioblastoma.

For example, according to the present invention, the diagnosis brain tumour by hitherto known diagnostic methods can be specified to be a CD95L positive brain tumour or a CD95L negative brain tumour, based upon the outcome of determination of CD95L expression in a tumour sample, as described herein. Such known diagnostic methods include known histological or histopathological methods such as known methods of tissue staining and known immunohistochemical methods.

Yet another aspect of the present invention is a monoclonal antibody of the invention for use in classifying a cancer disease according the level of CD95L expression. In this aspect, the cancer disease can be classified by the level of CD95L expression into a CD95L positive cancer disease or a CD95L negative cancer disease. The level of CD95L expression is preferably determined in an immunohistochemcial method using the antibody of the invention.

In this aspect, the cancer can be any cancer, as described herein. In particular, the cancer disease is selected from the group consisting of brain cancer, colon cancer, colorectal cancer, pancreatic cancer, breast cancer, lung cancer, renal cancer, liver cancer or/and metastatic disease thereof. More particular, the cancer disease is glioma, most particular glioblastoma.

Another aspect of the present invention is an anti-CD95L antibody of the invention for use in providing a prognosis about the overall survival time or/and the relapse-free survival time in a cancer patient, by classifying the cancer disease of the patient by the level of CD95L expression. The level of CD95L expression is preferably determined in an immunohistochemcial method using the antibody of the invention.

In this aspect, the cancer can be any cancer, as described herein. In particular, the cancer disease is selected from the group consisting of brain cancer, colon cancer, colorectal cancer, pancreatic cancer, breast cancer, lung cancer, renal cancer, liver cancer or/and metastatic disease thereof. More particular, the cancer disease is glioma, most particular glioblastoma.

In the present invention, the overall survival time (OS) denotes the chances of staying alive for a group of individuals suffering from a cancer. It denotes the percentage of individuals in the group who are likely to be alive after a particular duration of time.

Yet another aspect of the present invention is a method of providing a prognosis about the overall survival time or/and the relapse-free survival time in a cancer patient, said method comprising
(a) determining CD95L expression in a cancer sample using an antibody of the invention, and
(b) providing a prognosis about the survival time or/and the relapse-free survival time of the patient by the level of CD95L expression, wherein the CD95L expression is negatively correlated with the survival time of the patient.

The invention is further illustrated by the following Figures and Examples.

FIGURE LEGENDS

FIG. 1: Peptide array with anti-CD95L antibody clone 119-4 (A) and intensity plot derived from said assay (B)

Figure 2B:
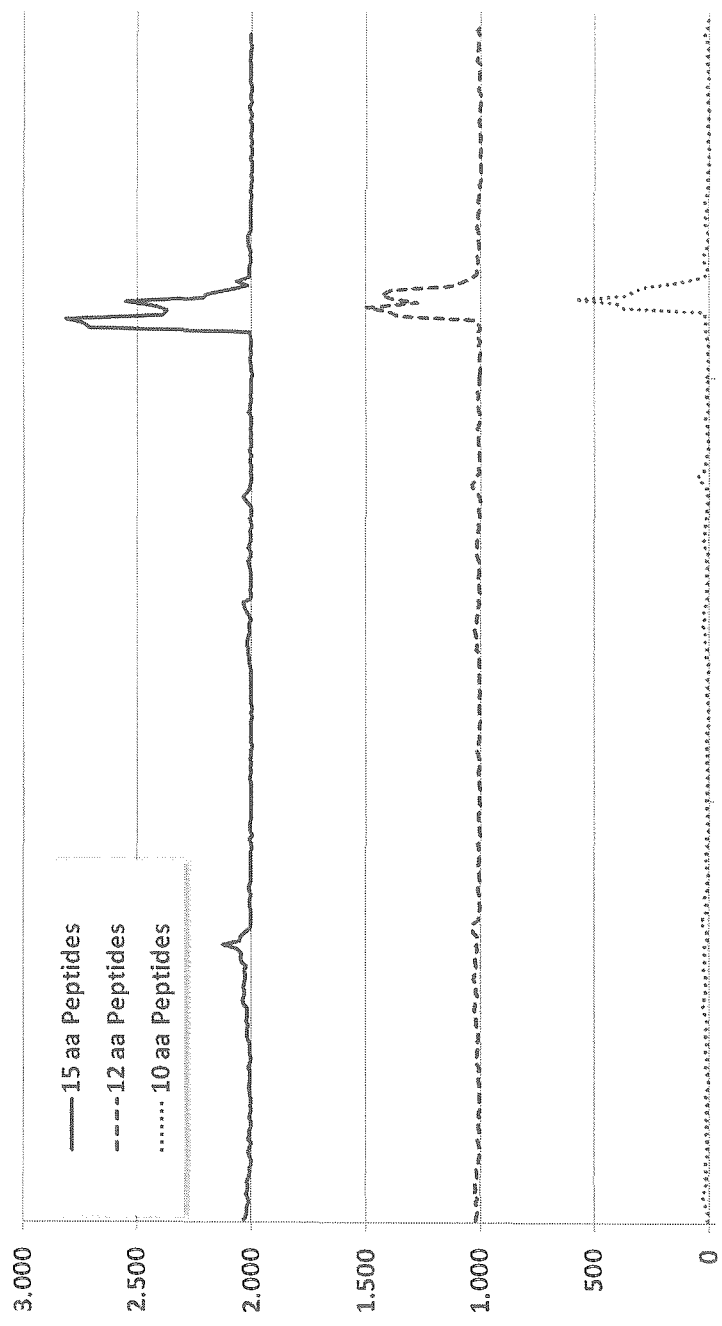

FIGS. 2A and 2B: Peptide array with anti-CD95L antibody clone 145-12 (A) and intensity plot derived from said assay (B)

Figure 3A:
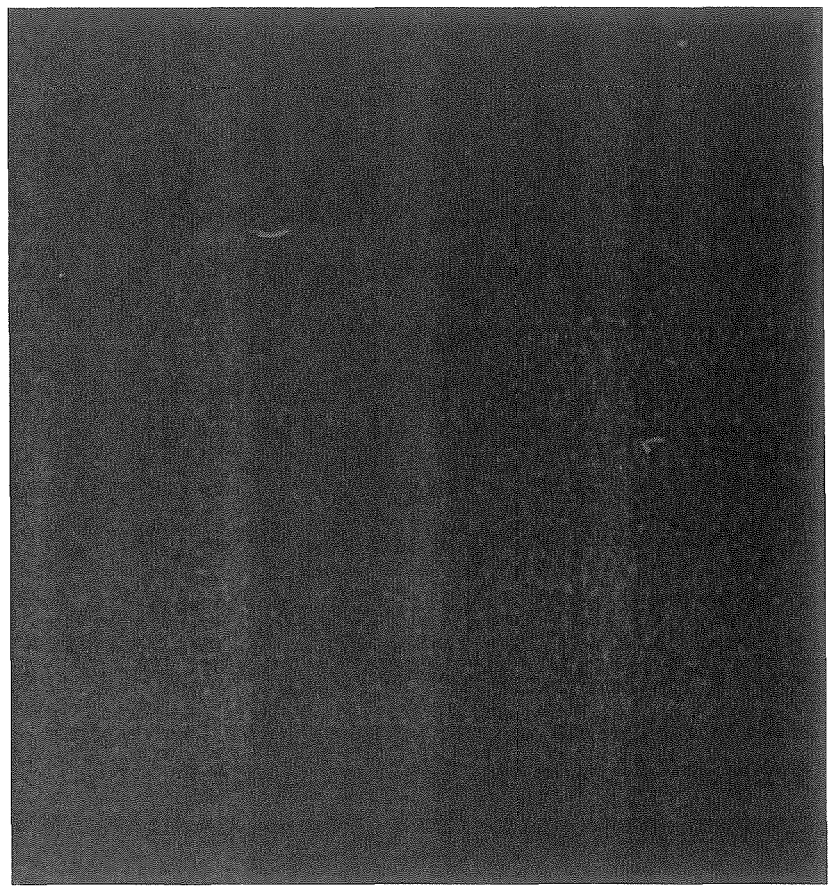
Figure 3B:
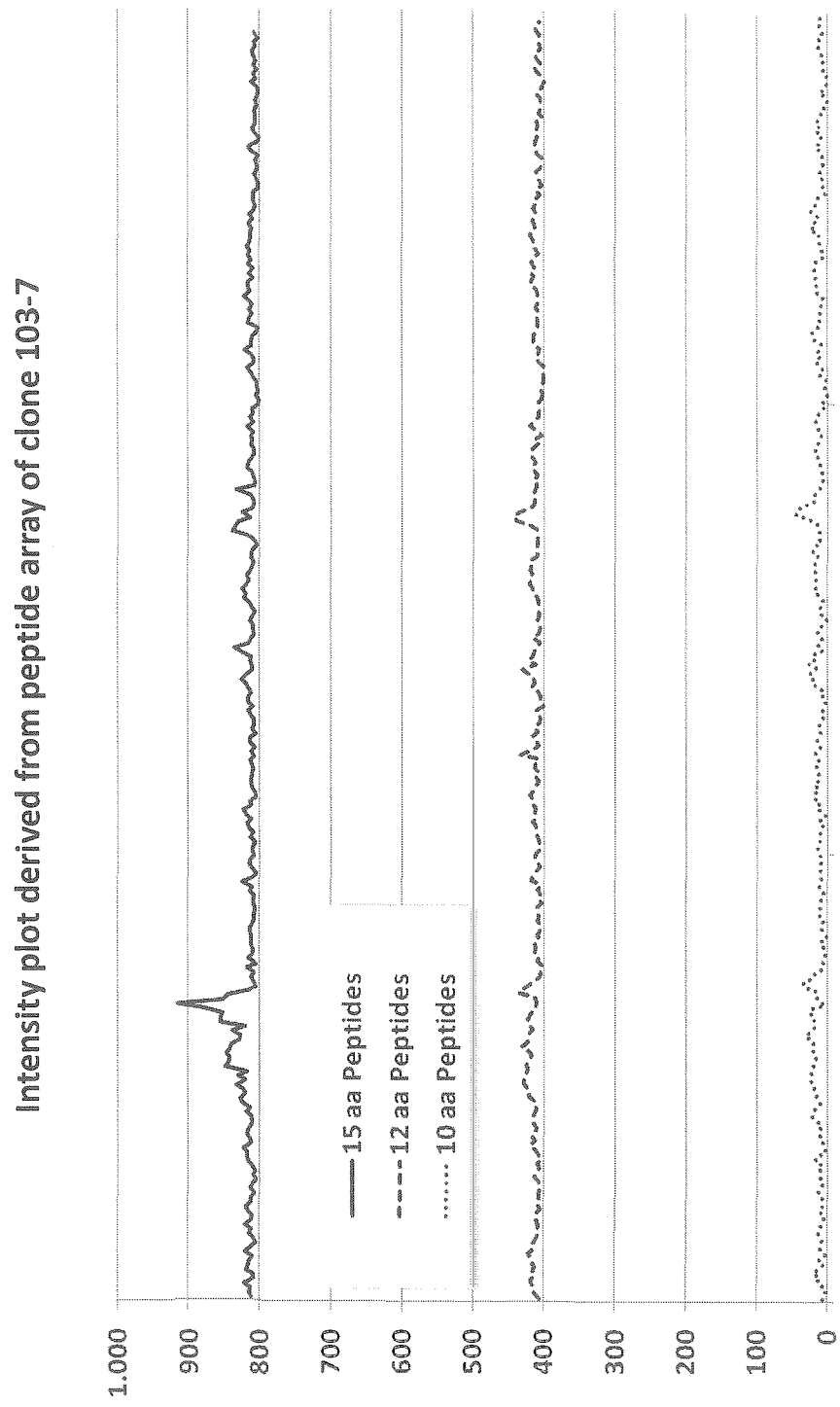

FIGS. 3A and 3B: Peptide array with anti-CD96L antibody clone 103-7 (A) and intensity plot derived from said assay (B)

Figure 4:
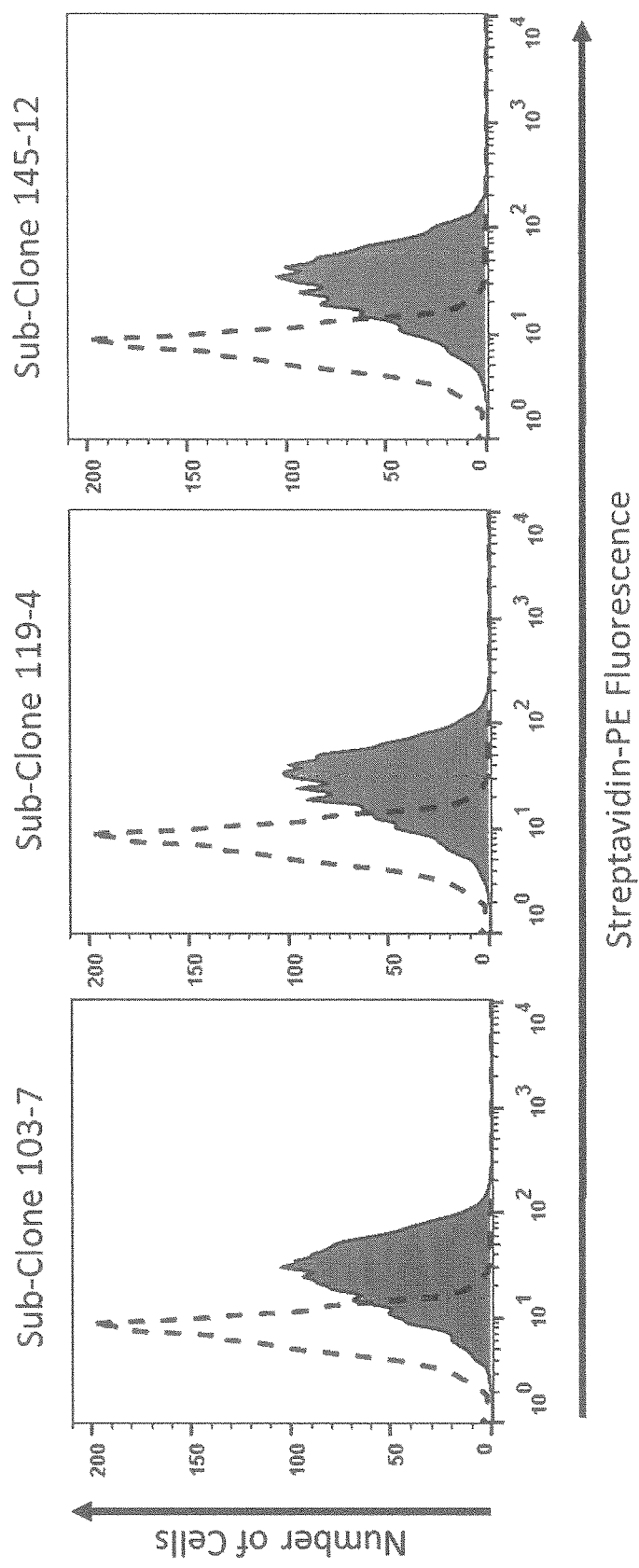

FIG. 4: Flow cytometric based detection of CD95L using the antibodies 119-4, 145-12 and 103-7. Dashed histogram: rabbit isotype control; filled histogram: sub-clone supernatant FIG. 5: Competition ELISA with specific competitor APG296

Figure 6:
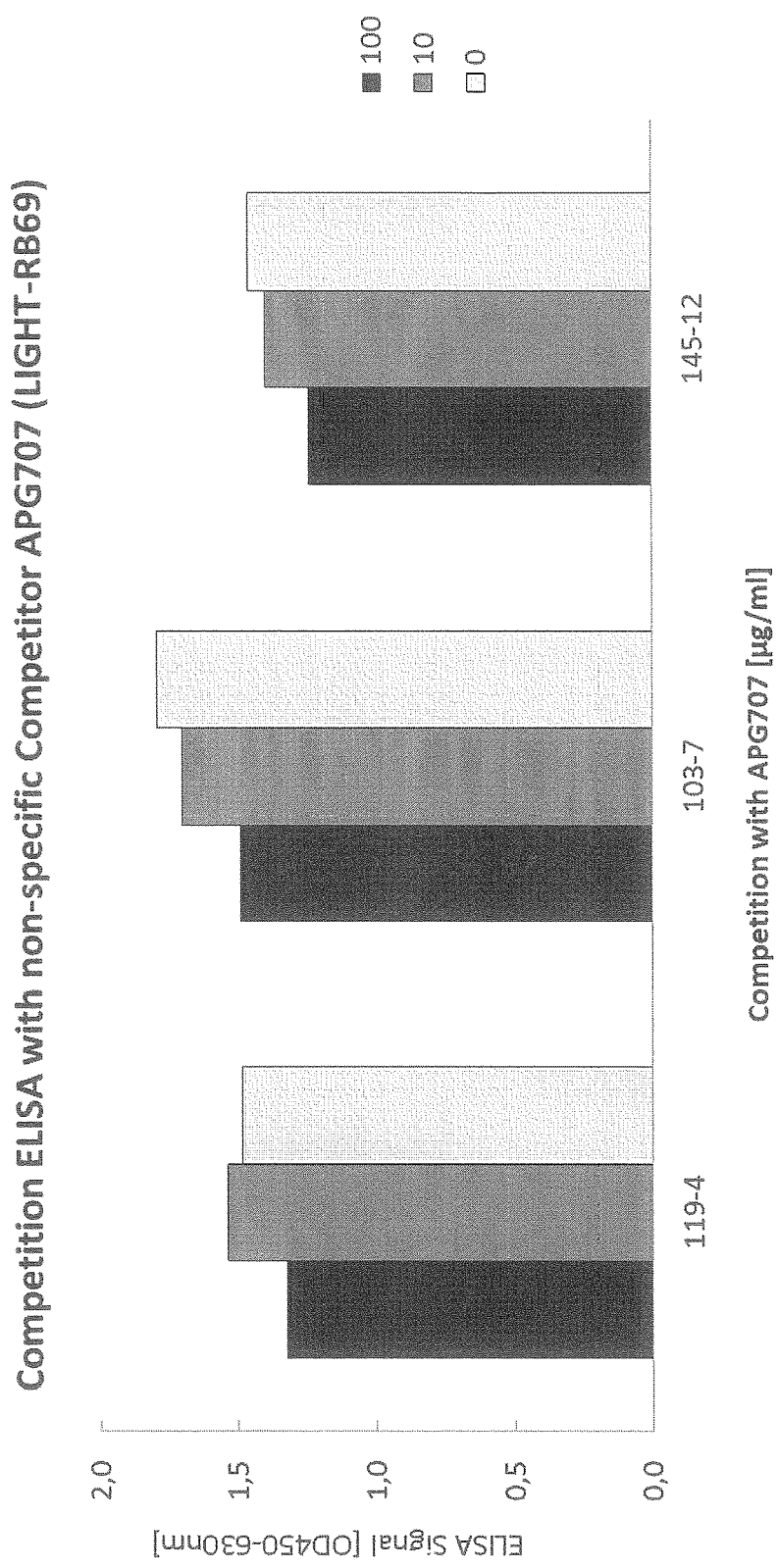

FIG. 6: Competition ELISA with non-specific competitor APG707

Figure 7:
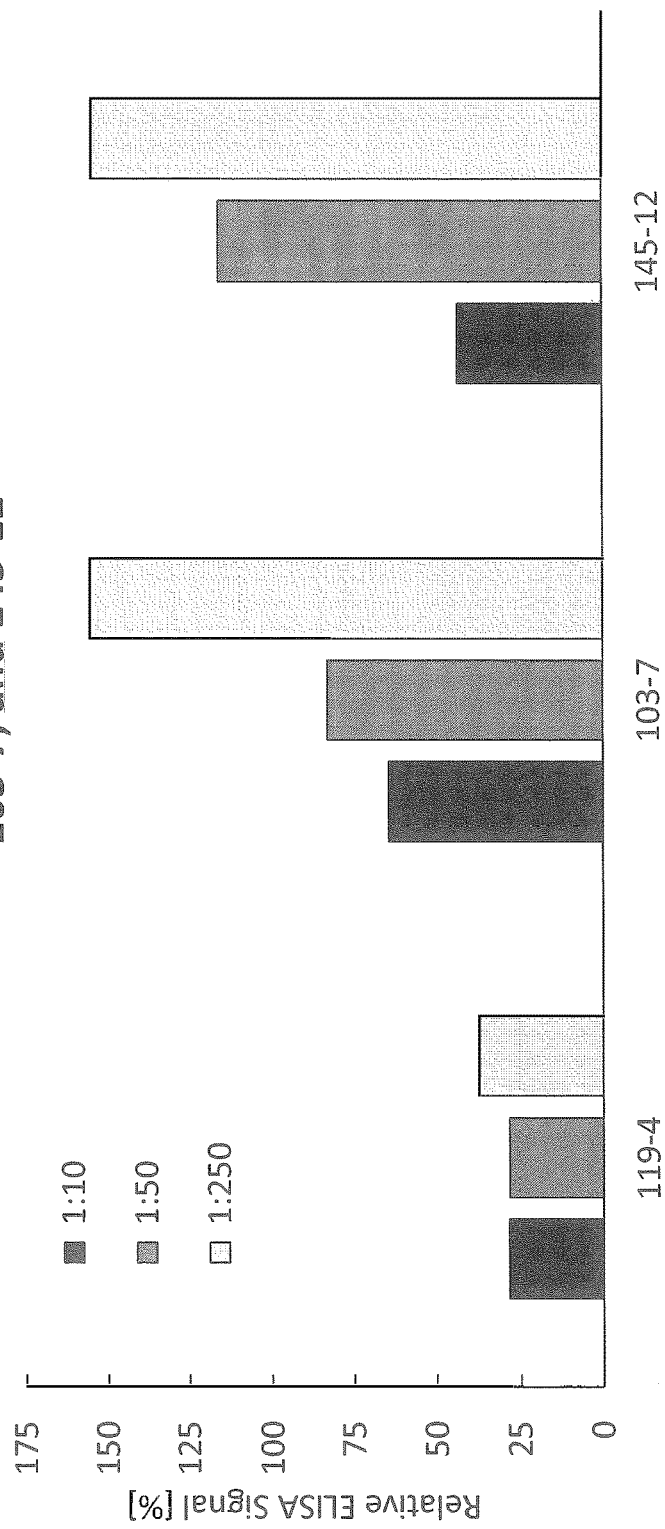

FIG. 7: Neutralization of APG101 binding to CD95L by subclones 119-4, 103-7 and 145-12

Figure 8:
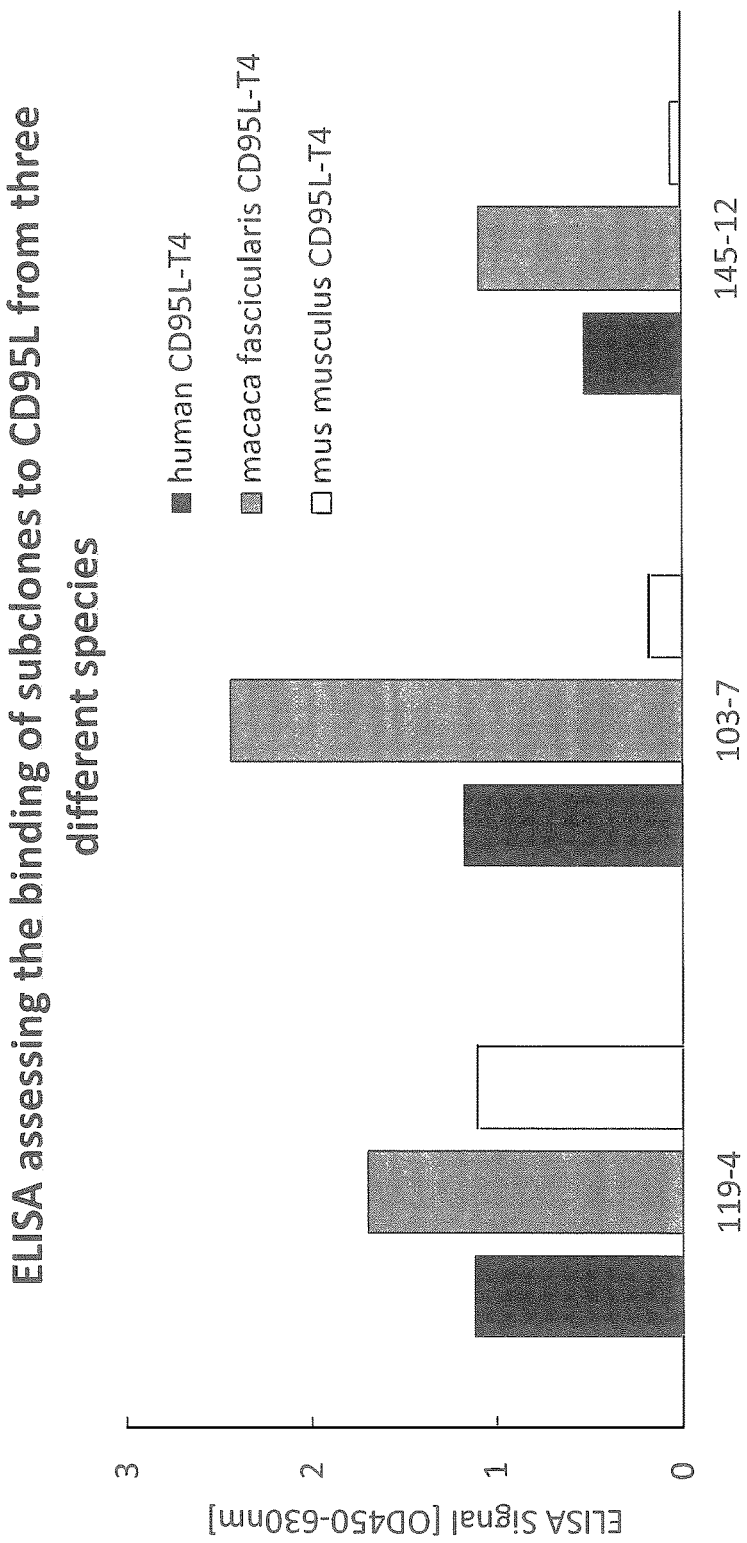

FIG. 8: ELISA assessing the binding of subclones to CD95L from three different species FIG. 9: Biological activity of CD95L-blockers: antagonism of human CD95L-induced apoptosis on Jurkat A3 cells FIG. 10: Biological activity of CD95L-blockers: antagonism of immobilized human CD95L-induced apoptosis on Jurkat A3 cells FIG. 11: Biological activity of CD95L-blockers: antagonism of immobilized monkey CD95L-induced apoptosis on Jurkat A3 cells FIG. 12: Biological activity of CD95L-blockers: antagonism of immobilized mouse CD95L-induced apoptosis on Jurkat A3 cells FIG. 13: Epitope mapping 119-4 peptide ELISA FIG. 14: Epitope mapping 145-12 peptide ELISA FIG. 15: Epitope mapping 103-7 peptide ELISA FIG. 16: Determination of the $K_D$ for antibodies 119-4 and 145-12

FIG. 17: Alignments of the amino acid sequences of the three humanized variable heavy ($V_H$) domains comprising either the original or the modified CDR-H's of rabbit monoclonal antibody 145-12 with the human $V_H$ consensus frameworks (hum III, heavy subgroup III) used. Complementarity Determining Regions (CDRs) are in brackets. The CDR'S of the recipient hum III are printed in italic and important heavy chain framework residues are marked (H28, H31a, H50, H71). All modifications described in the humanization procedure are printed in small letters and underlined. Shown is Hum III of SEQ ID NO:53; huVH145_A of SEQ ID NO:30; huVH145_B of SEQ ID NO:31 and huVH145_C of SEQ ID NO:32

FIG. 18: Alignment of the amino acid sequences of the three humanized variable heavy ($V_H$) domains comprising either the original or the modified CDR-H's of rabbit monoclonal antibody 119-4 with the human $V_H$ consensus frameworks (hum III, heavy subgroup III) used. Complementarity Determining Regions (CDRs) are in brackets. The CDR'S of the recipient hum III are printed in italic and important heavy chain framework residues are marked (H28, H31a, H50, H71). All modifications described in the humanization procedure are printed in small letters and underlined. Shown is Hum III of SEQ ID NO:53; huVH119_A of SEQ ID NO:41; huVH119_B of SEQ ID NO:42 and huVH119_C of SEQ ID NO:43

FIG. 19: Alignment of the amino acid sequences of humanized variable light chain ($V_L$) domains of rabbit monoclonal antibodies 119-4 and 154-12 and human $V_L$ consensus framework. Complementarity Determining Regions (CDRs) are in brackets. The CDR'S of the recipient sequence are printed in italic. Shown is hu_k1 of SEQ ID NO:54; hu119_4 of SEQ ID NO:44 and hu145_12 of SEQ ID NO:33

Example 1: Immunization/Screening Strategy For Anti-CD95L

For the generation of CD95L-antibodies rabbits were immunised with recombinant CD95L (APG296; SEQ ID NO: 26). Animals showing a high serum titer against CD95L (APG296) by ELISA were selected for the generation of rabbit monoclonal antibodies. For this procedure lymphocytes were isolated from rabbit spleen and fused with rabbit myeloma cells. Growing hybridoma cells were screened for the presence of antibodies in the cell culture supernatant and subsequently tested for their specificity to recognize CD95L. In summary, 163 supernatants of growing hybridoma were tested for detection of CD95L in an ELISA based assay as a primary screen. About 70 clones showed interaction with CD95L and were further characterized in detail by ELISA, IHC, Western-Blot and FACS-analysis. Three clones (103, 119 and 145) were selected and sub-cloned via limited dilution to ensure monoclonality. The (sub)clones 103-7, 119-4, 145-12 were finally selected for further characterisation.

Example 2: Peptide Array

Pre-staining of the peptide array was done with the secondary goat anti-rabbit IgG (H+L) DyLight680 antibody at a dilution of 1:5000 to investigate background interactions that could interfere with the main assays. Subsequent incubation of the peptide microarrays with rabbit monoclonal antibody clones 103-7, 119-4 and 145-12 at dilution of 1:1000 and 1:100 (103-7 and 145-12) in incubation buffer was followed by staining with the secondary goat anti-rabbit IgG (H+L) DyLight680 antibody and read-out of the fluorescence intensities.

Quantification of spot intensities and peptide annotation were done with PepSlide® Analyzer and listed in an Excel file. A software algorithm breaks down fluorescence intensities of each spot into raw, foreground and background signal and calculates the standard deviation of foreground median intensities. Based on averaged foreground median intensities, an intensity map was generated and binders in the peptide map highlighted The averaged spot intensities of the assays were plotted with rabbit monoclonal antibodies 103-7, 119-4 and 145-12 against the human CD95L sequence from the N- to the C-terminus to visualize overall spot intensities and signal to noise ratios (see FIGS. 1, 2 and 3). The intensity plots were finally correlated with peptide and intensity maps as well as with visual inspection of the microarray scans to identify the peptides and consensus motif that interacted with the monoclonal antibody sample.

Example 3: Epitope Mapping of Rabbit Monoclonal Antibodies

Incubation of one of the peptide microarrays with rabbit monoclonal antibody 119-4 at a dilution of 1:1000 (left) was followed by staining with the secondary goat anti-rabbit IgG (H+L) DyLight680 antibody. We observed a strong and well-defined threefold spot pattern formed by rows of neighboured peptides. This was in accordance with the microarray layout shown in the peptide map with the 10 aa peptides on top, the 12 aa peptides in the middle and the 15 aa peptides on bottom of the peptide microarray.

Data quantification was followed by generation of peptide and intensity maps as well as of an intensity plot. In accordance with the microarray scan, we observed a strong and well-defined threefold epitope-like spot pattern after incubation with rabbit monoclonal antibody 119-4 at a dilution of 1:1000 in incubation buffer. The rows of neighboured spots at all peptide lengths were correlated with the consensus motif that formed the epitope of rabbit monoclonal antibody 119-4 (FIG. 1). Similar arrays were done for antibodies 145-12 and 103-7 (FIGS. 2 and 3).

For antibodies 119-4 and 145-12 a consensus epitope encoding the amino acids RNSKYPQD could be assigned.

No epitope could be assigned for clone 103-7. The corresponding antibody has a non-linear structural epitope.

Example 4: Facs Analysis of CD95L Expression

Flow cytometric analysis of CD95L expression was performed on KFL9 cell. Prior to the incubation with primary antibodies cells were blocked with FACS buffer (PBS, 5% FCS, 1/100 Gammunex). Subsequently, the primary antibodies 103-7, 119-4 and 145-12 (or a respective isotype control antibody) were added and incubated for 30 min. After three washing steps with PBS a secondary goat anti-rabbit biotin antibody was added. Specifically, bound antibodies were detected by addition of PE-conjugated Streptavidin. The entire protocol was performed on ice or at 4° C. Flow cytometric analysis was performed by a Guava EasyCyte Mini. The histograms of FIG. 4 show the fluorescence intensity of the clones 103-7, 119-4 and 145-12 in comparison to the rabbit isotype control antibody (dashed line). All clones are equally capable of specific detection of CD95L on the cell surface of KFL9 cells.

Example 5: Competition Elisa with Specific Competitor APG296

Figure 5:
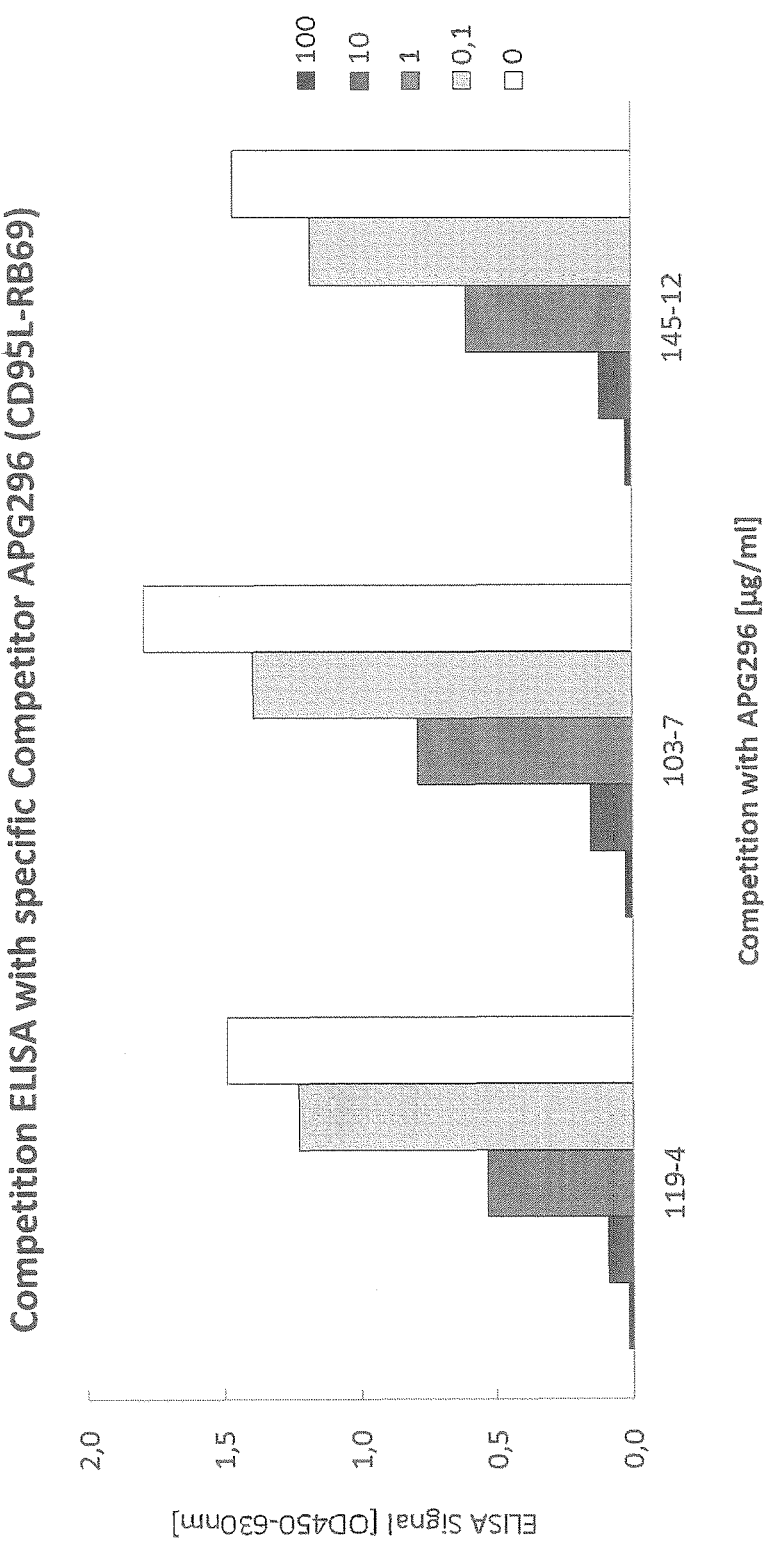

For the competition ELISA, 96-well microtiter plates were coated with 10 µg/ml APG296 (CD95L-RB69; SEQ ID NO: 26). After blocking with StartingBlock, wells were incubated with antibodies from subclones 119-4, 103-7 and 145-12 at a final dilution of 1:200 in the absence or presence of the specific competitor APG296 (0, 0.1, 1, 10 or 100 µg/ml). Binding of the rabbit monoclonal antibodies was detected by incubation with goat anti rabbit IgG-Peroxidase (Sigma; dilution 1:5000) and subsequent detection of the converted Peroxidase-substrate TMB one at a wavelength of 450 nm in an ELISA reader (FIG. 5).

For antibodies from clones 119-4, 103-7 and 145-12 a dose-dependent competition of the ELISA signal was observed in the presence of the specific competitor. At the highest concentration tested (100 µg/ml) the ELISA signal was reduced to background level.

Example 6: Competition Elisa with Non-Specific Competitor APG707

For the competition ELISA, 96-well microtiter plates were coated with 10 µg/ml APG296 (CD95L-RB69). After blocking with StartingBlock, wells were incubated with antibodies from subclones 119-4, 103-7 and 145-12 at a final dilution of 1:200 in the absence or presence of the non-specific competitor APG707 (LIGHT-RB69; SEQ ID NO: 27; 0, 10 or 100 µg/ml). Binding of the rabbit monoclonal antibodies was detected by incubation with goat anti rabbit IgG-Peroxidase (Sigma; dilution 1:5000) and subsequent detection of the converted Peroxidase-substrate TMBone at a wavelength of 450 nm in an ELISA reader (FIG. 6).

No competition was seen for antibodies from subclones 119-4, 103-7 and 145-12 in the presence of an unspecific competitor. Even high concentrations of APG707 showed no significant competition of the ELISA signal.

Example 7: Neutralization of CD95 (Receptor) Binding to CD95L by Antibodies from Subclones 119-4, 103-7 and 145-12

APG101 is a fusion protein comprising the Fc-part of human IgG1 and the extracelluar "Ligand Binding Domain"

of CD95. APG101 shows strong binding to CD95L and is particularly suited to analyse the ability of CD95L-antibodies to interfere with CD95L/CD95 interaction:

The neutralization of the binding of APG101 to CD95L by subclones 119-4, 103-7 and 145-12 was assessed by ELISA. 96-well microtiter plates were coated with 5 µg/ml StrepMabImmo (IBA). After blocking with StartingBlock, wells were incubated with 1 µg/ml CD95L-T4 (APG293) containing a StrepTag which is captured by StrepMabImmo. Wells were then incubated with subclones 119-4, 103-7 and 145-12 at dilutions of 1:10, 1:50 and 1:250. In a next incubation step, APG101 at a concentration of 1 µg/ml was added. Binding of APG101 to CD95L was detected by incubation with goat anti human IgG-Peroxidase (Sigma; dilution 1:5000) and subsequent detection of the converted Peroxidase-substrate TMBone at a wavelength of 450 nm in an ELISA reader. Data are expressed as relative ELISA signal with a 100% value indicating no neutralisation of the binding of APG101 to CD95L and a 0% value indicating a complete neutralization of the binding of APG101 to CD95L (FIG. 7).

Antibodies from subclones 103-7 and 145-12 showed neutralisation of APG101 binding in a dose dependent manner. In comparison antibodies from subclone 119-4 showed a more efficient neutralisation of APG101 binding.

Example 8: Elisa Assessing the Binding of Antibody Subclones to CD95L from Three Different Species For the ELISA assessing the species specificity of three different subclones, 96-well microtiter plates were coated with 0.5 µg/ml human CD95L-T4 (black) or 0.5 µg/ml *Macaca fascicularis* CD95L-T4 (dark grey) or 0.5 µg/ml *Mus musculus* CD95L-T4 (light grey). After blocking with StartingBlock, wells were incubated with subclones 119-4, 103-7 and 145-12 at a final dilution of 1:200. Binding of the rabbit monoclonal antibodies was detected by incubation with goat anti rabbit IgG-Peroxidase (Sigma; dilution 1:5000) and subsequent detection of the converted Peroxidase-substrate TMBone at a wavelength of 450 nm in an ELISA reader (FIG. 8).

Clone 119-4 shows strong binding to CD95L from all tested species. Antibodies from clone 103-7 and 119-4 showed strong binding to human and monkey CD95L and only weak binding to CD95L derived from mouse.

Figure 9:
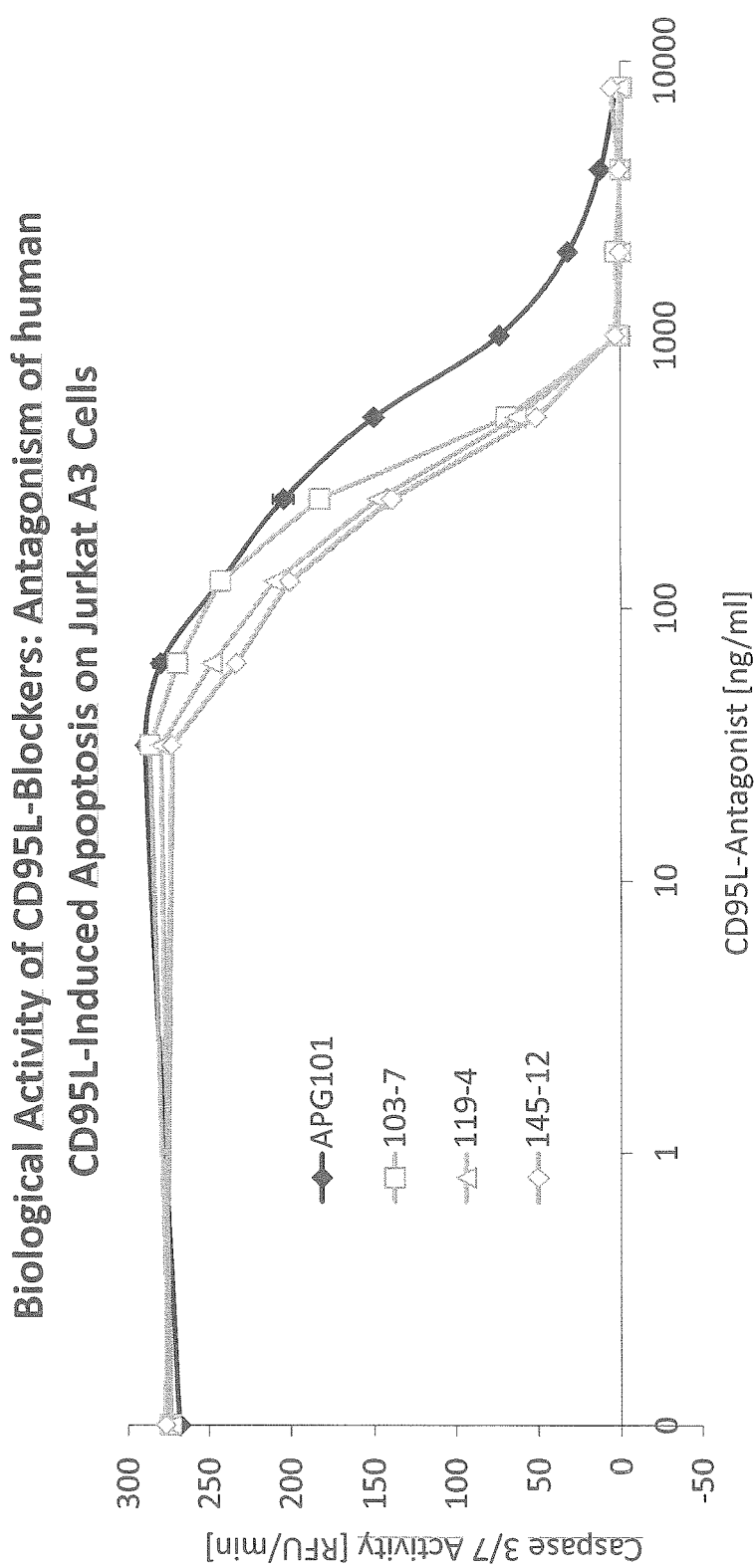

Example 9: Biological Activity of CD95L-BLOCKERS: Antagonism of Human CD95L-Induced Apoptosis on Jurkat A3 CELLS For the cellular assay assessing the biological activity of three different subclones (103-7, 119-4, 145-12) in comparison to APG101, 96-well microtiter plates were pipetted with 100000 Jurkat A3 cells per well. Then, the wells were supplemented with a constant concentration of finally 250 ng/ml APG293 (human CD95L-T4; SEQ ID NO: 25) and a titration of CD95L-antagonist as indicated on the x-axis. After 3 hours incubation at 37° C., cells were lysed with lysis buffer (250 mM HEPES, 50 mM MgCl2, 10 mM EGTA, 5% Triton-X-100, 100 mM DTT, 10 mM AEBSF, pH 7.5) and plates were put on ice for 30 minutes to 2 hours. Cleavage of the caspase substrate Ac-DEVD-AFC was used to determine the extent of apoptosis: 20 µl cell lysate was transferred to a black 96-well microtiter plate; after the addition of 80 µl buffer containing 50 mM HEPES, 1% Sucrose, 0.1% CHAPS, 50 µM Ac-DEVD-AFC, and 25 mM DTT, pH 7.5, the plate was transferred to a Tecan microtiter plate reader and the increase in fluorescence intensity was monitored (excitation 400 nm, emission 505 nm) (FIG. 9).

All four CD95L-antagonists show a dose-dependent inhibition of Caspase induction. The three antibodies (subclones 103-7, 119-4, 145-12) reveal a higher antagonistic activity compared to APG101.

Figure 10:
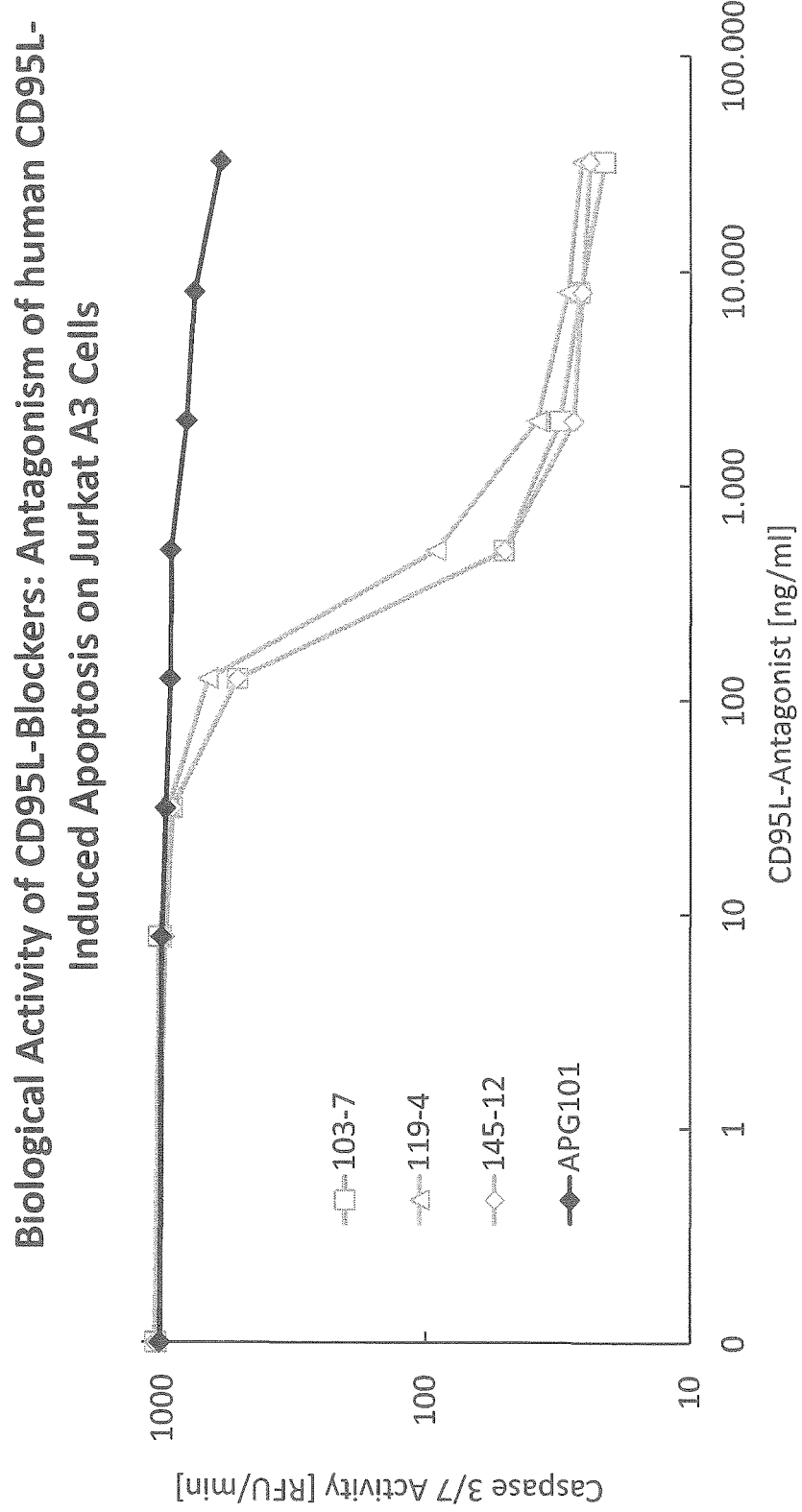

Example 10: Biological Activity of CD95L-Blockers: Antagonism of Apoptosis Induced on Jurkat A3 Cells by Immobilized Human CD95L For the cellular assay assessing the biological activity of three different subclones (103-7, 119-4, 145-12) in comparison to APG101, 96-well StrepTactin microtiter plates (IBA) were incubated for 1 hour with 250 ng/ml human CD95L-RB69 (APG296) which was captured by the immobilised StrepTactin via its Strep-Tag. After washing the plate, CD95L-antagonists at different concentrations as indicated on the x-axis were incubated for 1 hour. After washing, 100000 Jurkat A3 cells per well were added. After 3 hours incubation at 37° C., cells were lysed with lysis buffer (250 mM HEPES, 50 mM MgCl2, 10 mM EGTA, 5% Triton-X-100, 100 mM DTT, 10 mM AEBSF, pH 7.5) and plates were put on ice for 30 minutes to 2 hours. Cleavage of the caspase substrate Ac-DEVD-AFC was used to determine the extent of apoptosis: 20 µl cell lysate was transferred to a black 96-well microtiter plate; after the addition of 80 µl buffer containing 50 mM HEPES, 1% Sucrose, 0.1% CHAPS, 50 µM Ac-DEVD-AFC, and 25 mM DTT, pH 7.5, the plate was transferred to a Tecan microtiter plate reader and the increase in fluorescence intensity was monitored (excitation 400 nm, emission 505 nm) (FIG. 10).

All tested antibodies showed efficient inhibition of apoptosis induced by recombinant human CD95L (APG296). Compared to the known CD95L-antagonist APG101 the antibodies showed a much higher efficacy.

Figure 11:
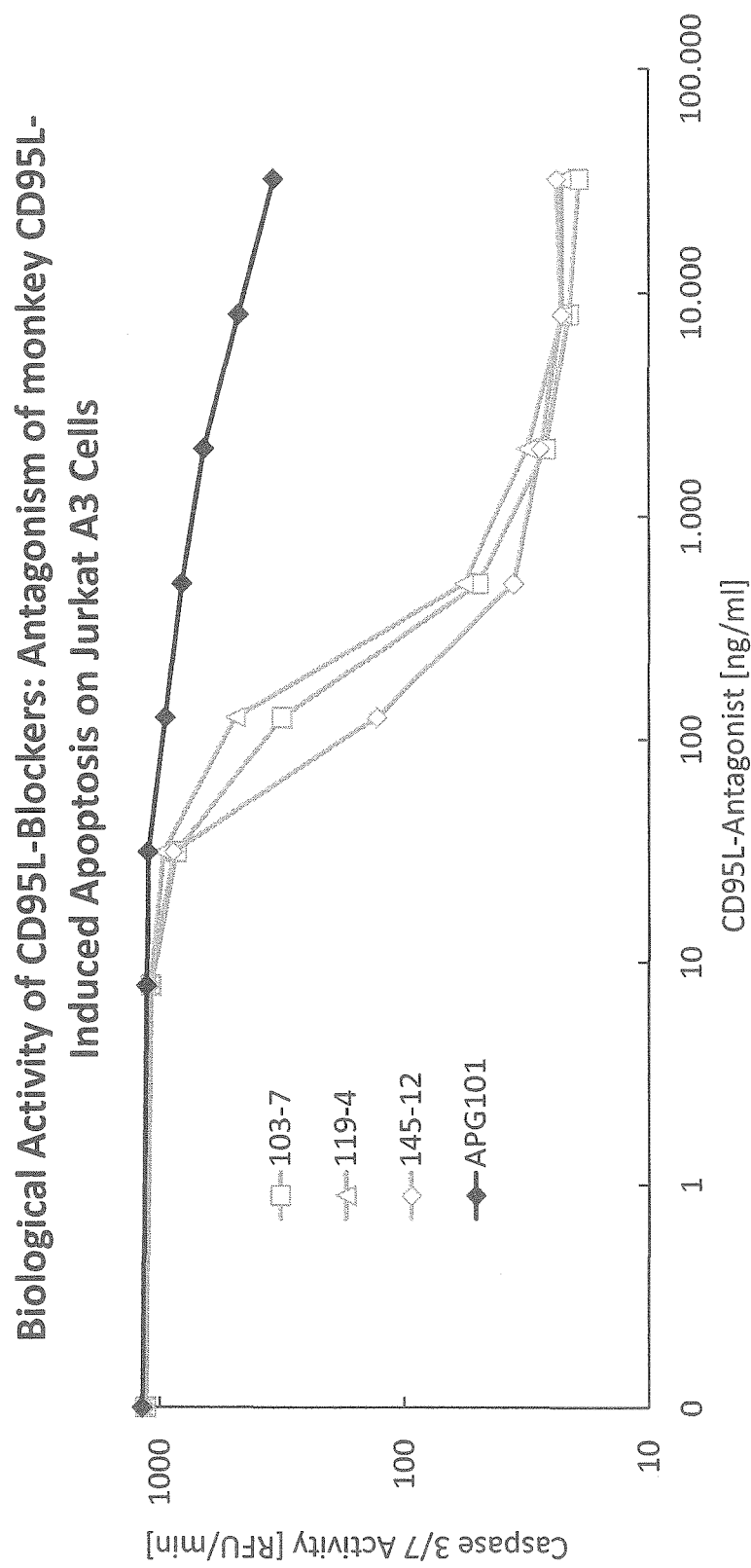

Example 11: Biological Activity of CD95L-Blockers: Antagonism of Apoptosis Induced on Jurkat A3 Cells by Immobilized Monkey CD95L For the cellular assay assessing the biological activity of three different subclones (103-7, 119-4, 145-12) in comparison to APG101, 96-well StrepTactin microtiter plates (IBA) were incubated for 1 hour with 250 ng/ml monkey CD95L-RB69 (*Macaca fascicularis*; APG1249) which was captured by the immobilised StrepTactin via its Strep-Tag. After washing the plate, CD95L-antagonists at different concentrations as indicated on the x-axis were incubated for 1 hour. After washing, 100000 Jurkat A3 cells per well were added. After 3 hours incubation at 37° C., cells were lysed with lysis buffer (250 mM HEPES, 50 mM MgCl2, 10 mM EGTA, 5% Triton-X-100, 100 mM DTT, 10 mM AEBSF, pH 7.5) and plates were put on ice for 30 minutes to 2 hours. Cleavage of the caspase substrate Ac-DEVD-AFC was used to determine the extent of apoptosis: 20 µl cell lysate was transferred to a black 96-well microtiter plate; after the addition of 80 µl buffer containing 50 mM HEPES, 1% Sucrose, 0.1% CHAPS, 50 µM Ac-DEVD-AFC, and 25 mM DTT, pH 7.5, the plate was transferred to a Tecan microtiter plate reader and the increase in fluorescence intensity was monitored (excitation 400 nm, emission 505 nm) (FIG. 11).

All tested antibodies showed efficient inhibition of apoptosis induced by recombinant monkey CD95L (APG1249). Compared to the known CD95L-antagonist APG101 the antibodies showed a much higher efficacy.

Example 12: Biological Activity of CD95L-Blockers: Antagonism of Apoptosis Induced on Jurkat A3 Cells by Immobilized Mouse CD95L For the cellular assay assessing the biological activity of three different subclones (103-7, 119-4, 145-12) in comparison to APG101, 96-well StrepTactin microtiter plates (IBA) were incubated for 1 hour with 250 ng/ml mouse CD95L-RB69 (*Mus musculus*; APG1250) which was captured by the immobilised StrepTactin via its Strep-Tag. After washing the plate, CD95L-antagonists at different concentrations as indicated on the x-axis were incubated for 1 hour. After washing, 100000 Jurkat A3 cells per well were added. After 3 hours incubation at 37° C., cells were lysed with lysis buffer (250 mM HEPES, 50 mM MgCl2, 10 mM EGTA, 5% Triton-X-100, 100 mM DTT, 10 mM AEBSF, pH 7.5) and plates were put on ice for 30 minutes to 2 hours. Cleavage of the caspase substrate Ac-DEVD-AFC was used to determine the extent of apoptosis: 20 μl cell lysate was transferred to a black 96-well microtiter plate; after the addition of 80 μl buffer containing 50 mM HEPES, 1% Sucrose, 0.1% CHAPS, 50 μM Ac-DEVD-AFC, and 25 mM DTT, pH 7.5, the plate was transferred to a Tecan microtiter plate reader and the increase in fluorescence intensity was monitored (excitation 400 nm, emission 505 nm).

Figure 12:
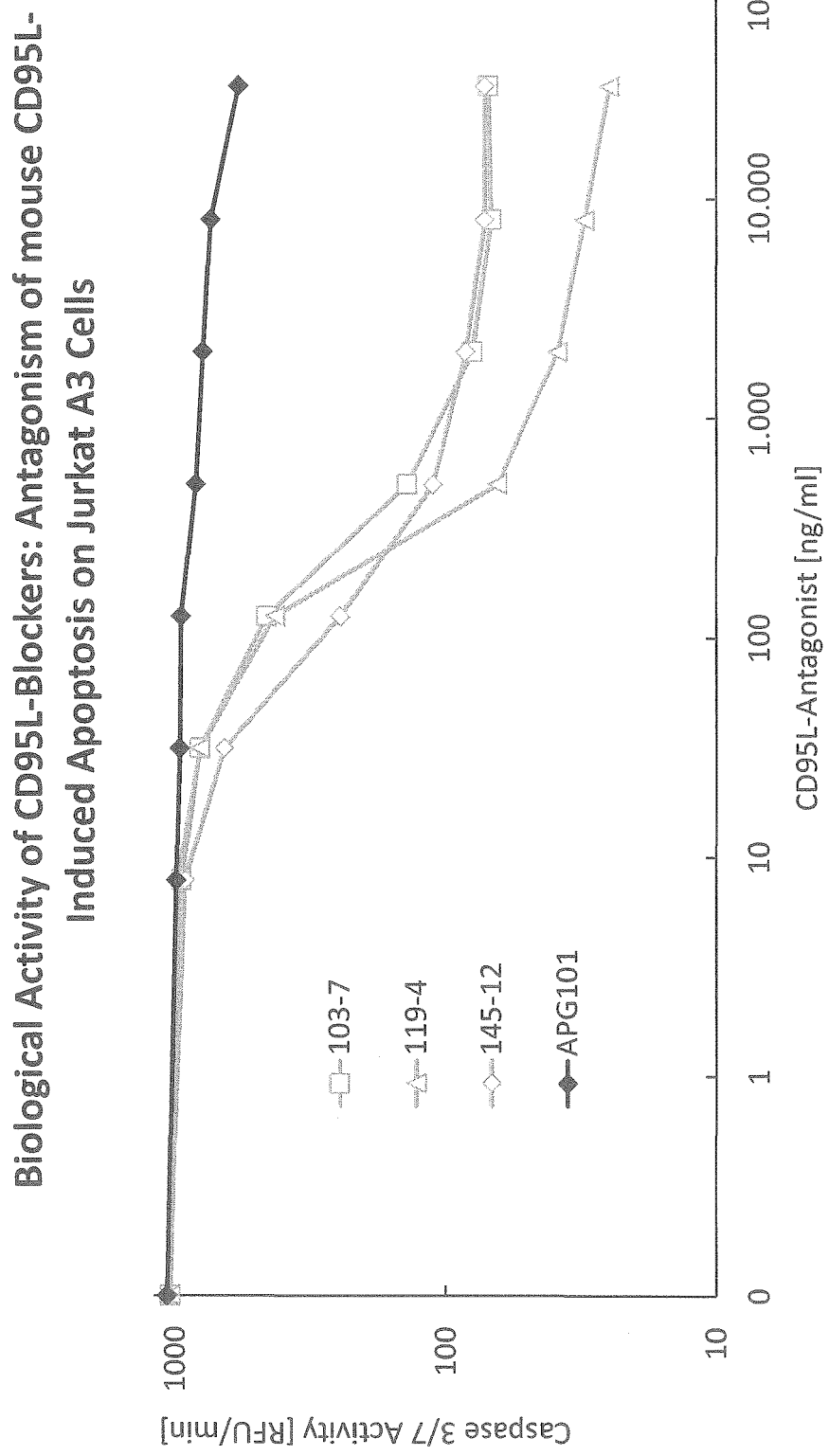

All tested antibodies showed efficient inhibition of apoptosis induced by recombinant mouse CD95L (APG1250). Compared to the known CD95L-antagonist APG101 the antibodies showed a much higher efficacy. However, only the subclone 119-4 is able to reduce Caspase activity induced by mouse CD95L to baseline levels (FIG. 12).

Example 13: Epitope Mapping 119-4 Peptide Elisa

Figure 13:
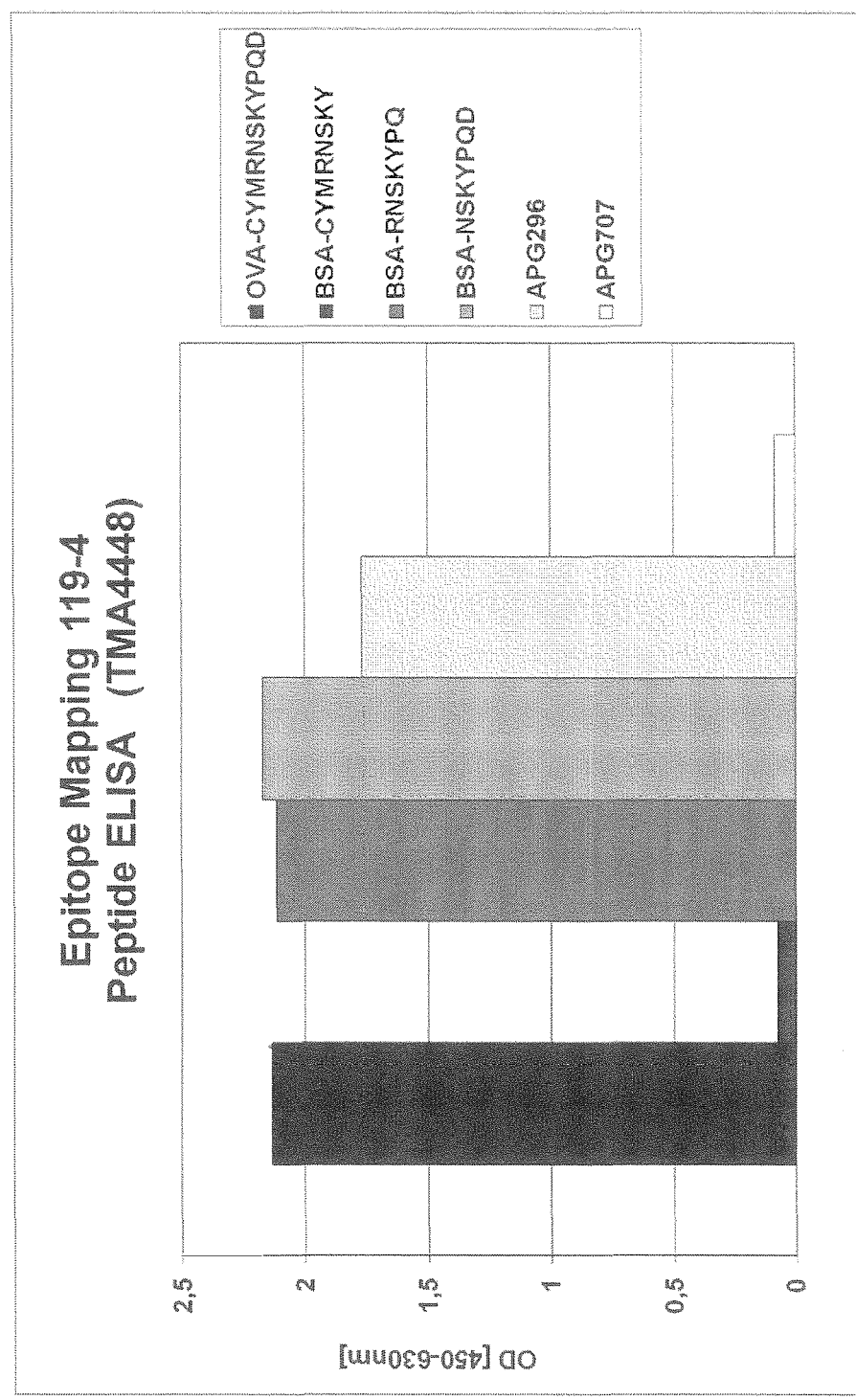

For the ELISA assessing the epitope of clone 119-4, 96-well microtiter plates were coated with 2 μg/ml human CD95L (APG296) or 2 μg/ml human LIGHT (APG707) or peptides immobilized to BSA or ovalbumin that comprise a part of the extracellular amino acid sequence of human CD95L. After blocking with StartingBlock, wells were incubated with clone 119-4 at a concentration of 2 μg/ml. Binding of the rabbit monoclonal antibody was detected by incubation with goat anti rabbit IgG-Peroxidase (Sigma; dilution 1:5000) and subsequent detection of the converted Peroxidase-substrate TMBone at a wavelength of 450 nm in an ELISA reader (FIG. 13).

Antibody 119-4 shows binding to APG296 and to all tested peptides except of the peptide "C-YMRNSKY". The respective binding pattern indicates a minimal epitope comprising the amino-acids "NSKYPQ".

Example 14: Epitope Mapping 145-12 Peptide Elisa

Figure 14:
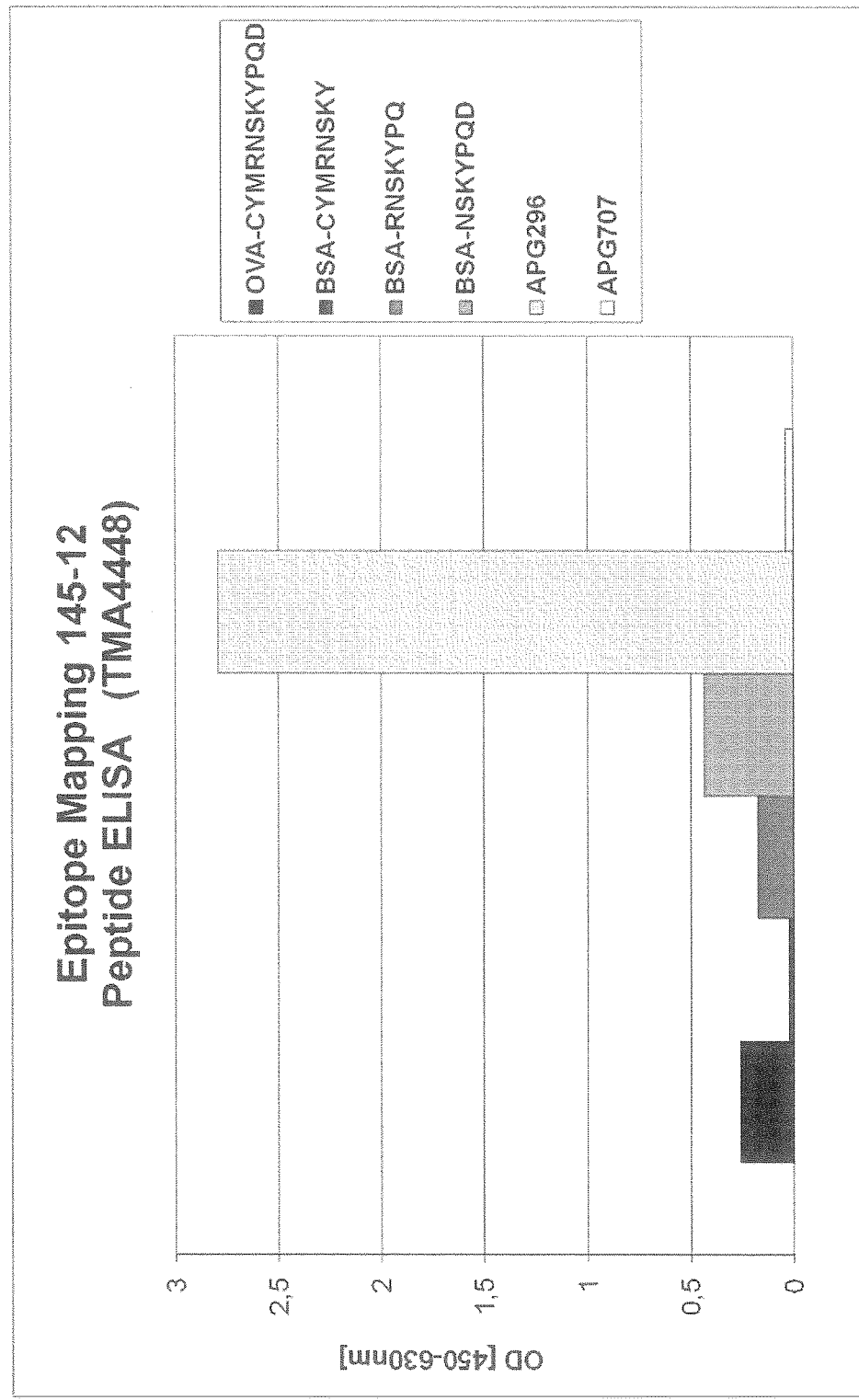

For the ELISA assessing the epitope of clone 145-12, 96-well microtiter plates were coated with 2 μg/ml human CD95L (APG296) or 2 μg/ml human LIGHT (APG707) or peptides immobilized to BSA or ovalbumin that comprise a part of the extracellular amino acid sequence of human CD95L. After blocking with StartingBlock, wells were incubated with clone 145-12 at a concentration of 2 μg/ml. Binding of the rabbit monoclonal antibody was detected by incubation with goat anti rabbit IgG-Peroxidase (Sigma; dilution 1:5000) and subsequent detection of the converted Peroxidase-substrate TMBone at a wavelength of 450 nm in an ELISA reader (FIG. 14).

Antibody 145-12 shows specific binding to APG296. However, binding to the tested peptides is weak or even absent (peptide "C-YMRNSKY"). Although the antibody shares the same epitope as clone 119-4 (as shown by peptide-array) it is conceivable that other possibly structural components of CD95L are required to define the full epitope of the 145-12 antibody.

Example 15: Epitope Mapping 103-7 Peptide Elisa

Figure 15:
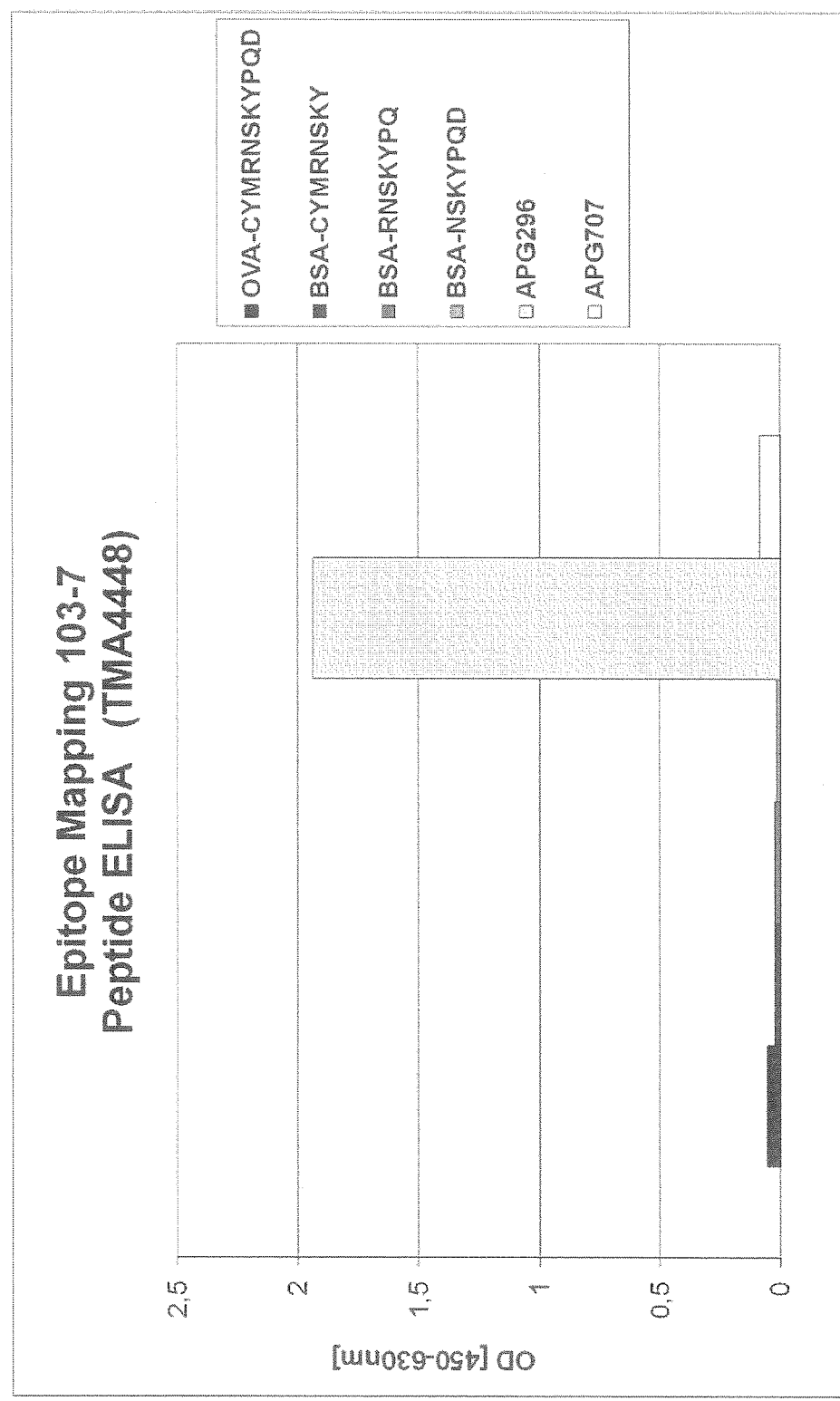

For the ELISA assessing the epitope of clone 103-7, 96-well microtiter plates were coated with 2 μg/ml human CD95L (APG296) or 2 μg/ml human LIGHT (APG707) or peptides immobilized to BSA or ovalbumin that comprise a part of the extracellular amino acid sequence of human CD95L. After blocking with StartingBlock, wells were incubated with clone 103-7 at a concentration of 2 μg/ml. Binding of the rabbit monoclonal antibody was detected by incubation with goat anti rabbit IgG-Peroxidase (Sigma; dilution 1:5000) and subsequent detection of the converted Peroxidase-substrate TMBone at a wavelength of 450 nm in an ELISA reader (FIG. 15).

Antibody 103-7 shows specific binding to APG296. All peptide based linear epitopes are not detected by antibody 103-7, indicating an epitope that is defined by the three dimensional structure of CD95L.

Example 16: Determination of the KO for Antibodies 119-4 and 145-12

The equilibrium binding constant (K) of antibodies 119-4 and 145-12 to the epitope-comprising peptide "YMRNSKYPQD" was calculated based on kinetic binding data ($k_{on}$ and $k_{off}$) determined with an automated biosensor system (Attana A100). The A100 allows to investigate molecular interactions in real-time based on the Quartz Crystal Microbalance (QCM) technique. For this purpose, the respective epitope comprising peptide was coupled to BSA and subsequently immobilized to the surface of a carboxyl-activated QCM-chip. Antibodies 119-4 and 145-12 were used as soluble analytes at different concentrations. Binding ($k_{on}$) and dissociation ($k_{off}$) was analyzed in real time, and the respective $K_D$ was calculated (see table in FIG. 16).

Antibody 119-4 shows a higher affinity towards the epitope comprising peptide in comparison to antibody 145-12. $K_D$ could not be analysed for clone 103-7 with the chosen setup (data not shown).

Proteins Used for Immunization and Analysis:

The receptor-binding-domains of human, mouse and monkey CD95L (CD95L-RBD) were expressed as homotrimeric fusion proteins with a C-terminal positioned stabilization domain. Two versions of the human CD95L-RBD were generated, identical regarding the CD95L-derived sequence, but different in the molecular layout of the stabilization domain (APG293, SEQ ID NO: 25 and APG296, SEQ ID NO: 26). For the identification and/or deselection of scaffold specific mAB's, a structural related protein from the TNF-superfamily comprising the same trimerisation scaffold was used (APG707, SEQ ID NO: 27). For binding analysis, the monkey CD95L-RBD (APG1249, SEQ ID NO: 28) as well as mouse CD95L-RBD (APG1250, SEQ ID NO: 29) were expressed with the same fusion protein technology. The general layout of aforementioned proteins and examples for their production are described in U.S. Pat. No. 8,147,843B2 and US008580273B2.

Example 17: In Silico Humanization

In the following, residue numbering follows the Kabat enumeration. For humanization of the rabbit VH and VL antibody fragments derived from the rabbit mAB 119-4 (SEQ ID NO:7 and SEQ ID NO:8) and mAB145-12 (SEQ ID NO:17 and SEQ ID NO:18) the following strategy was used: Instead of searching individual human VH/VL-germline sequences with high similarity to the individual donor VH/VL-rabbit sequences, a human recipient VH/VL domain pair (VH subgroup III, SEQ ID 53 and VL kappa subgroup I SEQ ID 54) was chosen, which was used frequently for the humanization procedure of murine VH/VL-domains as acceptor framework (Presta et al. 1997, Adams et al., 2006). For the humanization of the rabbit VL fragments of both antibodies, a direct in silico grafting of the rabbit CDR-L's into the human VL-kappa subgroup I framework template (SEQ ID 54) without any changes was performed (see FIG. 19). The resulting humanized VL domain of mAB145-12 has the SEQ ID 33 and the resulting humanized VL domain of mAB119-4 has the SEQ ID 44.

For the humanization of the rabbit VH fragments of both antibodies, in silico grafting of the rabbit CDR-H's into the human framework template was performed and three humanized VH-sequence variants were created for each donor rabbit-VH domain (see FIG. 17 and FIG. 18). In both humanized variant A sequences, positions H28, H71 and H73 were switched from the recipient (H28-T, H71-R, H73-N) to the donor sequence residues (H28-S, H71-K, H73-S). Variant A was the template for further modifications resulting in variants B. In both humanized variant B sequences, in addition to aforementioned mutation of the framework residues H28, H71 and H73, the CDR-H2 positions H61, H62 and H63 of CDR-H2 were mutated from the rabbit donor (H61-S, H62-W, H63-A) to the human acceptor residues (H61-D, H62-S, H63-V). Variant B was the template for further modifications resulting in variants C. In both humanized variant C sequences, in addition to variant B mutations, the cysteine in the rabbit CDR-H1 (position H35a) was mutated to serine and the cysteine in the rabbit CDR-H2 (position H50) was mutated to alanine as cysteines are rare at those positions in human VH domains. The adjacent framework position H49 in both humanized variant C sequences was mutated from alanine to serine giving potentially a better structural support of the modified CDR-H2 in variants C. The resulting humanized VH domains of mAB145-12 have the SEQ ID 30 (Variant A), SEQ ID 31 (Variant B) and SEQ ID 32 (Variant C). The resulting humanized VH domains of mAB119-4 have the SEQ ID 41 (Variant A), SEQ ID 42 (Variant B) and SEQ ID 43 (Variant C).

In the case of the VH, Presta et al. defined the CDR-H1 by structural aspects to comprise heavy chain residues H26-H35, whereas the sequence based definition of the CDR-H1 comprises residues H31-H35 (Kabat enumeration). As the positions H26-H30 are involved in CDR-H1 loop conformation and position H28 is surface exposed, residue H28 is likely to be mutated to the donor sequence. In addition, heavy chain positions H69, H71 and H73 are known to be critical with respect to the conformation of the CDR-H loops of the VH subgroup III in general. For the chosen human VH/VL recipient domain pair it was discovered that replacement of the human to the donor residues was essential to enable functional engraftment of mouse CDR's in the aforementioned positions (Adams et al., 2006).

By visually inspecting the crystal structure of an Fab-fragment derived from a monoclonal rabbit antibody (pdb entry 4ZT0, Chain H, SEQ ID 61), additional general features of the rabbit VH domain framework and the rabbit CDR-H's were discovered. First of all, the CDR-H2 of the rabbit VH of SEQ ID 61 comprises C-terminal a tryptophane (residue H62-W) which is anchoring a loop formed by residues H60-H65 positioned lateral at the VH-scaffold structure supporting the N-terminal CDR-H2 conformation at the surface which is involved in antigen recognition. By its relative position close to the surface, this H62-tryptophane containing sequence motif is likely to be potential immunogenic in a humanized antibody intended for therapeutic purposes. A similar CDR-H2 loop-forming sequence is part of the mAb119-4 as well as of the mAb145-12. Therefore, we replaced the rabbit residues H61-H63 with the human residues H61-H63 as described above to reduce the immunogenicity risk of the resulting antibody fragment in humans, as implemented in SEQ ID 31, SEQ ID 32, SEQ ID 42 and SEQ ID 43. An additional structural feature observed in the aforementioned structure is a disulfide-bridge formed by the rabbit residues H35a and H50. Interestingly, this disulfide-bridge is buried in the rabbit VH/VL domain interface and links two antiparallel beta-barrels of the domain. As these beta-barrels support CDR-H1 and CDR-H2, a covalent linkage restricts potentially the structural flexibility of the CDR-H1 and CDR-H2. This could lead to structural features enabling and/or enhancing binding of the recognized antigen. As to proof this hypothesis for mAB119-4 and mAB145-12, in which the H35a and H50 cysteines are present, the human VH variants C (SEQ ID 32 and SEQ ID 43) were created where these cysteine residues were replaced.

Example 18: Functional Screening of the Humanized VH and VL-Domains of m145-12 and 119-4

For the compound based verification of the in silico humanization procedure, the scFv-minibody format was selected. Hingeless scFv-minibodies containing the humanized VH/VL pairs presenting the mAb145-12 and mAb119-4 specific CDR's were created according to Olafsen et al. 2004. The following modifications were implemented: The scFvs were generated in VH-VL orientation with a shorter 16 residue (GGGS)×4 linker. The C-terminal serine of the human VH and the C-terminal arginine of the human VL are not present in the constructs. The CH3 scaffold used comprises an N-terminal 5 residue linker element and a C-terminal Streptag-II for efficient affinity purification purposes at neutral pH. As a control the corresponding scFv-minibodies comprising the VH/VL domains of mAb 145-12 and mAb 119-4 were produced. In the rabbit VL-domains, the singular cysteine forming the disulfide-bridge to the rabbit kappa-constant domain was mutated to serine. For mammalian based secretory pathway based production, synthetic cDNA-cassettes were generated encoding a suitable signal peptide in frame to the scFv-minibody of interest and cloned into expression vectors suitable for stable expression in mammalian cells. Production of the scFv-minibodies was performed by the methods as described below. All scFv-minibodies produced were finally purified by size exclusion chromatography ensuring multimer and aggregate depletion prior to further analytics, thereby excluding avidity effects in the subsequent activity assays performed. The SEC-purified anti-CD95L specific scFv-minibodies were analysed for their capability to neutralize CD95L induced apoptosis on Jurkat A3 cells. Functional reconstitution of the CD95L epitope recognition in the humanized scFv-Minibodies created with the mAB145-12 or mAB119-4 CDR's is assumed to directly translate in EC50 values comparable or lower than the EC50 values of the rabbit control scFv-minibodies comprising the rabbit donor VH/VL-domains.

Example 19: Methods for Cloning, Expression and Purification of Recombinant Full Length Antibodies or Antibody Fragments The aforementioned full length antibodies or antibody fragments are usually expressed recombinantly in two different eukaryotic host cells:

For initial analysis of aforementioned full length antibodies or antibody fragments, Hek293T cells grown in DMEM+ GlutaMAX (GibCo) supplemented with 10% FBS, 100 units/ml Penicillin and 100 [mu]g/ml Streptomycin are transiently transfected with a plasmid containing an expression cassette for recombinant polypeptide and an appropriate selection marker, e.g. a functional expression cassette comprising a blasticidine, puromycin or hygromycin resistance gene. In those cases, where a plurality of polypeptide chains is necessary to achieve the final product (e.g. full format antibodies), the expression cassettes are either combined on one plasmid or positioned on different plasmids during the transfection. Cell culture supernatant containing recombinant fusion polypeptides is harvested three days post transfection and clarified by centrifugation at 300×g followed by filtration through a 0.22 μm sterile filter.

For larger scale expression of aforementioned full length antibodies or antibody fragments to be used in vivo, synthetic DNA cassettes encoding the aforementioned proteins are inserted into eukaryotic expression vectors comprising appropriate selection markers (e.g. a functional expression cassette comprising a blasticidin, puromycin or hygromycin resistance gene) and genetic elements suitable to enhance the number of transcriptionally active insertion sites within the host cells genome, e.g the human β-globin matrix attachment region (MAR). The sequence verified expression vectors are introduced by electroporation into suspension adapted Chinese Hamster Ovary cells (CHO-S, Invitrogen). Appropriate selection pressure was applied three days post-transfection to the transfected cells. Surviving cells carrying the vector derived resistance gene(s) are recovered by subsequent cultivation under selection pressure. Upon stable growth of the selected cell pools in chemically defined medium (PowerCHO2-CD, Lonza) at 37° C. and 7% CO2 atmosphere in an orbital shaker incubator (100 rpm, 50 mm shaking throw), the individual supernatants are analyzed by ELISA-assays detecting the aforementioned proteins and the cell pools with the highest specific productivity are expanded in shake flasks prior to protein production (orbital shaker, 100 rpm, shaking throw 50 mm).

For lab-scale protein production, individual cell pools are cultured for 7-12 days in chemically defined medium (PowerCHO2-CD, Lonza) at 37° C. and 7% CO2 atmosphere in a Wave bioreactor 20/50 EHT (GE-Healthcare). The basal medium is PowerCHO2-CD supplemented with 4 mM Glutamax. Wave culture started with a viable cell concentration of 0.3 to 0.4×10e6 cells/ml and the following settings (for a five- or ten liter bag): shaking frequency 18 rpm, shaking ankle 7°, gas current 0.2-0.3 L/min, 7% CO2, 36.5° C. During the Wave run, the cell culture are fed twice with PowerFeed A (Lonza), usually on day 2 (20% feed) and day 5 (30% feed). After the second feed, shaking frequency is increased to 22 rpm, as well as the shaking ankle to 8°.

The bioreactor is usually harvested in between day 7 to day 12 when the cell viability dropped below 80%. First, the culture supernatant is clarified using a manual depth filtration system (Millipore Millistak Pod, MC0HC 0.054 m2). For Strep-tagged proteins, Avidin is added to a final concentration of 0.5 mg/L. Finally, the culture supernatant containing the aforementioned full length antibodies or antibody fragments is sterile filtered using a bottle top filter (0.22 μm, PES, Corning) and stored at 2-8° C. until further processing.

For affinity purification Streptactin Sepharose is packed to a column (gel bed 1 ml), equilibrated with 15 ml buffer W (100 mM Tris-HCl, 150 mM NaCl, pH 8.0) or PBS pH 7.4 and the cell culture supernatant is applied to the column with a flow rate of 4 ml/min. Subsequently, the column is washed with 15 ml buffer W and bound polypeptide is eluted stepwise by addition of 7×1 ml buffer E (100 mM Tris HCl, 150 mM NaCl, 2.5 mM Desthiobiotin, pH 8.0). Alternately, PBS pH 7.4 containing 2.5 mM Desthiobiotin can be used for this step.

Alternately to the Streptactin Sepharose based method, the affinity purification is performed employing a column with immobilized Protein-A as affinity ligand and a Akta chromatography system (GE-Healthcare). A solid phase material with high affinity for the FC-domain of the fusion protein is chosen: MABSelect Sure™ (GE Healthcare). Briefly, the clarified cell culture supernatant is loaded on a HiTrap MabSelectSure column (CV=5 ml) equilibrated in wash-buffer-1 (20 mM Pi, 95 mM NaCl, pH7.2) not exceeding a load of 10 mg fusion protein per ml column-bed. The column is washed with ten column-volumes (10CV) of aforementioned equilibration buffer followed by four column-volumes (4CV) of wash-buffer-2 (20 mM Pi, 95 mM NaCl, pH 8.0) to deplete host-cell protein and host-cell DNA. The column is then eluted with elution buffer (20 mM Pi, 95 mM NaCl, pH 3.5) and the eluate is collected in up to ten fractions with each fraction having a volume equal to column-bed volume (5 ml). Each fraction is neutralized with an equal volume of aforementioned wash-buffer-2. The linear velocity is set to 150 cm/h and kept constant during the aforementioned affinity chromatography method. The protein amount of the eluate fractions is quantitated and peak fractions are concentrated by ultrafiltration and further purified by size exclusion chromatography (SEC).

SEC is performed on Superdex 200 10/300 GL or HiLoad 26/60 columns using an Akta chromatography system (GE-Healthcare). The columns are equilibrated with phosphate buffered saline and the concentrated, affinity-purified polypeptide is loaded onto the SEC column with the sample volume not exceeding 2% (v/v) of the column-volume. In the case of Superdex 200 10/300 GL columns (GE Healthcare), a flow rate of 0.5 ml per minute is applied. In the case of HiLoad 26/60 Superdex200 columns, a flow rate of 2.5 ml per minute is applied. The elution profile of the polypeptide is monitored by absorbance at 280 nm.

Example 20: Potency of CD95L Blockers

Standard potency assay, according to Example 9, was used to analyse the antagonistic CD95L activity of humanized VH/VL-domains in the scFv-Minibody format. Functional reconstitution of the CD95L epitope recognition in the humanized scFv-Minibodies created with the mAB145-12 or mAB119-4 CDR's is assumed to directly translate in EC50 values comparable or lower than the EC50 values of the rabbit control scFv-minibodies (SEC ID 37 representing mAb145-12 specificity and SEQ ID 48 representing mAb119-4 specificity). The chosen humanization strategy allowed to preserve activity in the range of the initial rabbit antibody as represented by the unmodified CDRs exemplified in the scFv-minibodies with SEQ ID 38 and 49. Surprisingly, the deimmunisation of the CDR-H2 of mAB145-12 as examplified in SEQ ID 39 increased potency. The deimmunisation of the CDRH2 of mAb119-4 worked also, as the relative activity of scFv-minibody SEQ ID 50 is comparable compared to the scFV-minibody with the SEQ ID 49. In contrast, modifications in of H35a in CDRH1 and H50 in CDRH2 significantly decreased potency as demonstrated with the SEQ ID 40 and SEQ ID 51 based scFv-minibodies.

| Compound | Assay 1 | Assay 2 | Assay 3 | Assay 4 | Assay 5 | Assay 6 | Mean | STABW |
|---|---|---|---|---|---|---|---|---|
| APG101 | 774 | 789 | 707 | 714 | — | — | 746 | 42 |
| maB145-12 | 187 | 198 | 225 | 192 | — | — | 201 | 16.9 |
| SEQ ID 37 | 124 | 117 | — | — | 113 | 118 | 118 | 4.7 |
| SEQ ID 38 | 118 | 114 | — | — | 95.7 | 111 | 110 | 9.7 |
| SEQ ID 39 | 99.4 | 105 | — | — | 86.5 | 83.4 | 93 | 10.2 |
| SEQ ID 40 | 532 | 591 | — | — | 701 | 571 | 599 | 72.5 |
| SEQ ID 48 | — | — | 116 | 90.8 | 84.4 | 97.5 | 97 | 13.8 |
| SEQ ID 49 | — | — | 172 | 144 | 117 | 127 | 140 | 24 |
| SEQ ID 50 | — | — | 169 | 136 | 128 | 140 | 143 | 18 |
| SEQ ID 51 | — | — | 1549 | 2256 | 1479 | 1737 | 1755 | 351 |

Table shows biological in vitro activity of different CD95L neutralizing reagents. Activity is determined as the antagonizing activity of the compounds with respect to the apoptosis induction of 250 ng/ml soluble CD95L-T4 on Jurkat A3 cells. Apoptosis induction is measured as cleavage of the substrate Ac-DEVD-AFC by Caspase 3/7. Values are expressed as EC50 in ng/ml.

Example 21: Generation of Full Length Antibody Formats

Full length human antibody formats can be generated by fusing the humanized VH and VL domains on appropriate scaffolds comprising the antibodies constant regions. An appropriate example sequence for the human constant kappa light chain is given in SEQ ID 58. Appropriate example sequences for the IGG1 constant heavy chain regions are given in SEQ ID 59 and SEQ ID 60. As an example, fusing humanized VL of mAb145-12 (SEQ ID 33) to the kappa constant light chain results in SEQ ID 36 representing a full length kappa light chain suitable to generate full format human antibodies with mAb145-12 specificity. Accordingly, by fusing humanized VL of mAb119-4 (SEQ ID NO 44) to the kappa constant light chain SEQ ID 58 results in SEQ ID 47 representing a full length kappa light chain suitable to generate full format human antibodies with mAb119-4 specificity. Similarly, the necessary human heavy chains are created by fusing SEQ ID 42 with SEQ ID 59 or SEQ ID 60 resulting in a full length human heavy chains (SEQ ID 46 and SEQ ID 45) suitable for the generation of full format human antibodies with mAb119-4 specificity.

Accordingly, fusing SEQ ID 31 with SEQ ID 59 or SEQ ID 60 results in a full length human heavy chains (SEQ ID 35 and SEQ ID 34) suitable for the generation of full format human antibodies with mAb145-12 specificity. Expression technologies to produce full format recombinant antibodies in mammalian cell culture are well established in the art.

For those ordinary skilled in the art, it is obvious that that other antibody scaffold technologies can be applied by employing the humanized VH/VL domains to generate different formats with the desired antibody specificity.

The invention claimed is:

1. A monoclonal anti-CD95L antibody, comprising
   a heavy chain amino acid sequence including CDRH1 as shown in SEQ ID NO: 1, CDRH2 as shown in SEQ ID NO: 2, and CDRH3 as shown in SEQ ID NO: 3, and
   a light chain amino acid sequence including CDRL1 as shown in SEQ ID NO: 4, CDRL2 as shown in SEQ ID NO: 5, and CDRL3 as shown in SEQ ID NO: 6.

2. The monoclonal antibody according to claim 1, which is a full-length immunoglobulin or a functional immunoglobulin fragment thereof selected from the group consisting of Fab, Fab', F(ab')2, Fv, and single chain antibodies (scFv).

3. The monoclonal antibody according to claim 1, comprising a heavy chain variable region having the amino acid sequence of SEQ ID NO: 7, and a light chain variable region having the amino acid sequence of SEQ ID NO: 8, or an amino acid sequence having a sequence identity of at least 95% thereto, provided that CDRH1 has the sequence of SEQ ID NO: 1, CDRH2 has the sequence of SEQ ID NO: 2 and CDRH3 has the sequence of SEQ ID NO: 3, CDRL1 has the sequence of SEQ ID NO: 4, CDRL2 has the sequence of SEQ ID NO: 5, and CDRL3 has the sequence of SEQ ID NO: 6.

4. The monoclonal antibody according to claim 1, comprising
   a heavy chain amino acid sequence of SEQ ID NO: 9, and
   a light chain amino acid sequence of SEQ ID NO: 10, or an amino acid sequence having a sequence identity of at least 95% thereto, provided that CDRH1 has the sequence of SEQ ID NO: 1, CDRH2 has the sequence of SEQ ID NO: 2 and CDRH3 has the sequence of SEQ ID NO: 3, CDRL1 has the sequence of SEQ ID NO: 4, CDRL2 has the sequence of SEQ ID NO: 5, and CDRL3 has the sequence of SEQ ID NO: 6.

5. The monoclonal antibody according to claim 1, which is a humanized or human antibody.

6. The monoclonal antibody according to claim 1, wherein a label or effector group is covalently attached to the antibody.

7. A humanized monoclonal antibody comprising at least a heavy chain variable region having the amino acid sequence of SEQ ID NO: 41, 42 or 43, and
   a light chain variable region having the amino acid sequence of SEQ ID NO: 44.

8. A humanized monoclonal antibody comprising
   a heavy chain variable region having the amino acid sequence of SEQ ID NO: 41 or 42 or 43 fused to human IgG1 heavy chain scaffold of SEQ ID NO: 59 or SEQ ID NO: 60, and
   a light chain amino acid sequence of SEQ ID NO: 47.

9. A humanized monoclonal antibody comprising
   a heavy chain amino acid sequence of SEQ ID NO: 45 or 46, and
   a light chain amino acid sequence of SEQ ID NO: 47.

10. A monoclonal single chain antibody having the sequence selected of SEQ ID NO: 48, 49, 50 or 51.

* * * * *

SEQUENCE LISTING

```
<160> NUMBER OF SEQ ID NOS: 60

<210> SEQ ID NO 1
<211> LENGTH: 6
<212> TYPE: PRT
<213> ORGANISM: Artificial Sequence
<220> FEATURE:
<223> OTHER INFORMATION: CDR-H1

<400> SEQUENCE: 1

Asp His Tyr Trp Met Cys
1               5

<210> SEQ ID NO 2
<211> LENGTH: 17
<212> TYPE: PRT
<213> ORGANISM: Artificial Sequence
<220> FEATURE:
<223> OTHER INFORMATION: CDR-H2

<400> SEQUENCE: 2

Cys Ile Tyr Thr Ala Asp Ser Asp Ser Tyr Tyr Ala Ser Trp Ala Lys
1               5                   10                  15

Gly

<210> SEQ ID NO 3
<211> LENGTH: 12
<212> TYPE: PRT
<213> ORGANISM: Artificial Sequence
```

```
<220> FEATURE:
<223> OTHER INFORMATION: CDR-H3

<400> SEQUENCE: 3

Asn Gly Ala Tyr Ala Gly Gly Pro Tyr Gly Asp Leu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CDR-L1

<400> SEQUENCE: 4

Gln Ala Ser Gln Ser Ile Arg Thr Ser Leu Val
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDR-L2

<400> SEQUENCE: 5

Lys Ala Ser Asp Leu Pro Ser
1               5

<210> SEQ ID NO 6
<211> LENGTH: 14
<212> TYPE: PRT
<213> ORGANISM: Artificial Sequence
<220> FEATURE:
<223> OTHER INFORMATION: CDR-L3

<400> SEQUENCE: 6

Gln Ser Tyr Asp Phe Arg Asp Thr Ile Asn Asn Gly His Ser
1               5                   10

<210> SEQ ID NO 7
<211> LENGTH: 120
<212> TYPE: PRT
<213> ORGANISM: Artificial Sequence
<220> FEATURE:
<221> NAME/KEY: REGION
<222> LOCATION: 1..29
<223> OTHER INFORMATION: HFR1
<220> FEATURE:
<223> OTHER INFORMATION: vH
<220> FEATURE:
<221> NAME/KEY: REGION
<222> LOCATION: 30..35
<223> OTHER INFORMATION: CDR-H1
<220> FEATURE:
<221> NAME/KEY: REGION
<222> LOCATION: 36..49
<223> OTHER INFORMATION: HFR2
<220> FEATURE:
<221> NAME/KEY: REGION
<222> LOCATION: 50..66
<223> OTHER INFORMATION: CDR-H2
<220> FEATURE:
<221> NAME/KEY: REGION
<222> LOCATION: 67..97
<223> OTHER INFORMATION: HFR3
<220> FEATURE:
<221> NAME/KEY: REGION
<222> LOCATION: 98..109
<223> OTHER INFORMATION: CDR-H3
```

-continued

```
<220> FEATURE:
<221> NAME/KEY: REGION
<222> LOCATION: 110..119
<223> OTHER INFORMATION: HFR4

<400> SEQUENCE: 7
```

Gln Ser Leu Glu Glu Ser Gly Gly Asp Leu Val Lys Pro Gly Gly Thr
1               5                   10                  15

Leu Thr Leu Thr Cys Thr Thr Ser Gly Phe Ser Phe Ser Asp His Tyr
            20                  25                  30

Trp Met Cys Trp Val Arg Gln Ala Pro Gly Lys Gly Leu Glu Trp Ile
            35                  40                  45

Ala Cys Ile Tyr Thr Ala Asp Ser Asp Ser Tyr Tyr Ala Ser Trp Ala
        50                  55                  60

Lys Gly Arg Phe Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Asn Gly Ala Tyr Ala Gly Gly Pro Tyr Gly Asp Leu Trp Gly Pro
            100                 105                 110

Gly Thr Leu Val Thr Val Ser Ser
        115                 120

```
<210> SEQ ID NO 8
<211> LENGTH: 113
<212> TYPE: PRT
<213> ORGANISM: Artificial Sequence
<220> FEATURE:
<221> NAME/KEY: REGION
<222> LOCATION: 1..23
<223> OTHER INFORMATION: LFR1
<220> FEATURE:
<223> OTHER INFORMATION: vL
<220> FEATURE:
<221> NAME/KEY: REGION
<222> LOCATION: 24..34
<223> OTHER INFORMATION: CDR-L1
<220> FEATURE:
<221> NAME/KEY: REGION
<222> LOCATION: 35..49
<223> OTHER INFORMATION: LFR2
<220> FEATURE:
<221> NAME/KEY: REGION
<222> LOCATION: 50..56
<223> OTHER INFORMATION: CDR-L2
<220> FEATURE:
<221> NAME/KEY: REGION
<222> LOCATION: 57..88
<223> OTHER INFORMATION: LFR3
<220> FEATURE:
<221> NAME/KEY: REGION
<222> LOCATION: 89..102
<223> OTHER INFORMATION: CDR-L3
<220> FEATURE:
<221> NAME/KEY: REGION
<222> LOCATION: 103..113
<223> OTHER INFORMATION: LFR4

<400> SEQUENCE: 8
```

Asp Ile Val Met Thr Gln Thr Pro Ser Ser Val Glu Ala Ala Val Gly
1               5                   10                  15

Gly Thr Val Thr Ile Lys Cys Gln Ala Ser Gln Ser Ile Arg Thr Ser
            20                  25                  30

Leu Val Trp Tyr Gln Gln Lys Pro Gly Gln Pro Pro Lys Leu Leu Ile
            35                  40                  45

Tyr Lys Ala Ser Asp Leu Pro Ser Gly Val Pro Ser Arg Phe Lys Gly
         50                  55                  60

Ser Gly Ser Gly Thr Gln Phe Thr Leu Thr Ile Ser Asp Leu Glu Cys
 65                  70                  75                  80

Ala Asp Ala Ala Thr Tyr Tyr Cys Gln Ser Tyr Asp Phe Arg Asp Thr
                 85                  90                  95

Ile Asn Asn Gly His Ser Phe Gly Gly Gly Thr Glu Val Val Val Lys
                100                 105                 110

Gly

<210> SEQ ID NO 9
<211> LENGTH: 462
<212> TYPE: PRT
<213> ORGANISM: Artificial Sequence
<220> FEATURE:
<223> OTHER INFORMATION: heavy chain (119-1)
<220> FEATURE:
<221> NAME/KEY: REGION
<222> LOCATION: 20..139
<223> OTHER INFORMATION: vH

<400> SEQUENCE: 9

Met Glu Thr Gly Leu Arg Trp Leu Leu Leu Val Ala Val Leu Lys Gly
 1               5                  10                  15

Val Gln Cys Gln Ser Leu Glu Glu Ser Gly Gly Asp Leu Val Lys Pro
                 20                  25                  30

Gly Gly Thr Leu Thr Leu Thr Cys Thr Thr Ser Gly Phe Ser Phe Ser
                 35                  40                  45

Asp His Tyr Trp Met Cys Trp Val Arg Gln Ala Pro Gly Lys Gly Leu
         50                  55                  60

Glu Trp Ile Ala Cys Ile Tyr Thr Ala Asp Ser Asp Ser Tyr Tyr Ala
 65                  70                  75                  80

Ser Trp Ala Lys Gly Arg Phe Thr Ile Ser Lys Thr Ser Ser Thr Thr
                 85                  90                  95

Val Thr Leu Gln Met Thr Ser Leu Thr Ala Ala Asp Thr Ala Thr Tyr
                100                 105                 110

Phe Cys Ala Arg Asn Gly Ala Tyr Ala Gly Gly Pro Tyr Gly Asp Leu
         115                 120                 125

Trp Gly Pro Gly Thr Leu Val Thr Val Ser Ser Gly Gln Pro Lys Ala
130                 135                 140

Pro Ser Val Phe Pro Leu Ala Pro Cys Cys Gly Asp Thr Pro Ser Ser
145                 150                 155                 160

Thr Val Thr Leu Gly Cys Leu Val Lys Gly Tyr Leu Pro Glu Pro Val
                165                 170                 175

Thr Val Thr Trp Asn Ser Gly Thr Leu Thr Asn Gly Val Arg Thr Phe
                180                 185                 190

Pro Ser Val Arg Gln Ser Ser Gly Leu Tyr Ser Leu Ser Ser Val Val
                195                 200                 205

Ser Val Thr Ser Ser Ser Gln Pro Val Thr Cys Asn Val Ala His Pro
    210                 215                 220

Ala Thr Asn Thr Lys Val Asp Lys Thr Val Ala Pro Ser Thr Cys Ser
225                 230                 235                 240

Lys Pro Thr Cys Pro Pro Pro Glu Leu Leu Gly Gly Pro Ser Val Phe
                245                 250                 255

Ile Phe Pro Pro Lys Pro Lys Asp Thr Leu Met Ile Ser Arg Thr Pro
                260                 265                 270

-continued

```
Glu Val Thr Cys Val Val Val Asp Val Ser Gln Asp Pro Glu Val
            275                 280                 285

Gln Phe Thr Trp Tyr Ile Asn Asn Glu Gln Val Arg Thr Ala Arg Pro
290                 295                 300

Pro Leu Arg Glu Gln Gln Phe Asn Ser Thr Ile Arg Val Val Ser Thr
305                 310                 315                 320

Leu Pro Ile Ala His Gln Asp Trp Leu Arg Gly Lys Glu Phe Lys Cys
                325                 330                 335

Lys Val His Asn Lys Ala Leu Pro Ala Pro Ile Glu Lys Thr Ile Ser
                340                 345                 350

Lys Ala Arg Gly Gln Pro Leu Glu Pro Lys Val Tyr Thr Met Gly Pro
            355                 360                 365

Pro Arg Glu Glu Leu Ser Ser Arg Ser Val Ser Leu Thr Cys Met Ile
370                 375                 380

Asn Gly Phe Tyr Pro Ser Asp Ile Ser Val Glu Trp Glu Lys Asn Gly
385                 390                 395                 400

Lys Ala Glu Asp Asn Tyr Lys Thr Thr Pro Ala Val Leu Asp Ser Asp
                405                 410                 415

Gly Ser Tyr Phe Leu Tyr Ser Lys Leu Ser Val Pro Thr Ser Glu Trp
                420                 425                 430

Gln Arg Gly Asp Val Phe Thr Cys Ser Val Met His Glu Ala Leu His
            435                 440                 445

Asn His Tyr Thr Gln Lys Ser Ile Ser Arg Ser Pro Gly Lys
            450                 455                 460

<210> SEQ ID NO 10
<211> LENGTH: 239
<212> TYPE: PRT
<213> ORGANISM: Artificial Sequence
<220> FEATURE:
<223> OTHER INFORMATION: light chain (119-1)
<220> FEATURE:
<221> NAME/KEY: REGION
<222> LOCATION: 24..136
<223> OTHER INFORMATION: vL

<400> SEQUENCE: 10

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ser
            20                  25                  30

Ser Val Glu Ala Ala Val Gly Gly Thr Val Thr Ile Lys Cys Gln Ala
        35                  40                  45

Ser Gln Ser Ile Arg Thr Ser Leu Val Trp Tyr Gln Gln Lys Pro Gly
    50                  55                  60

Gln Pro Pro Lys Leu Leu Ile Tyr Lys Ala Ser Asp Leu Pro Ser Gly
65                  70                  75                  80

Val Pro Ser Arg Phe Lys Gly Ser Gly Ser Gly Thr Gln Phe Thr Leu
                85                  90                  95

Thr Ile Ser Asp Leu Glu Cys Ala Asp Ala Ala Thr Tyr Tyr Cys Gln
                100                 105                 110

Ser Tyr Asp Phe Arg Asp Thr Ile Asn Asn Gly His Ser Phe Gly Gly
            115                 120                 125

Gly Thr Glu Val Val Val Lys Gly Asp Pro Val Ala Pro Thr Val Leu
        130                 135                 140

Ile Phe Pro Pro Ala Ala Asp Gln Val Ala Thr Gly Thr Val Thr Ile
145                 150                 155                 160
```

```
Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235

<210> SEQ ID NO 11
<211> LENGTH: 6
<212> TYPE: PRT
<213> ORGANISM: Artificial Sequence
<220> FEATURE:
<223> OTHER INFORMATION: CDR-H1

<400> SEQUENCE: 11

Ser Gly Tyr Asp Met Cys
1               5

<210> SEQ ID NO 12
<211> LENGTH: 17
<212> TYPE: PRT
<213> ORGANISM: Artificial Sequence
<220> FEATURE:
<223> OTHER INFORMATION: CDR-H2

<400> SEQUENCE: 12

Cys Ile Asp Thr Asp Asn Asp Ala Thr Tyr Tyr Ala Ser Trp Ala Lys
1               5                   10                  15

Gly

<210> SEQ ID NO 13
<211> LENGTH: 10
<212> TYPE: PRT
<213> ORGANISM: Artificial Sequence
<220> FEATURE:
<223> OTHER INFORMATION: CDR-H3

<400> SEQUENCE: 13

Thr His Gly Asp Tyr Val Ala Phe Lys Leu
1               5                   10

<210> SEQ ID NO 14
<211> LENGTH: 13
<212> TYPE: PRT
<213> ORGANISM: Artificial Sequence
<220> FEATURE:
<223> OTHER INFORMATION: CDR-L1

<400> SEQUENCE: 14

Gln Ser Ser Gln Ser Val Tyr Lys Asn Asn Asp Leu Ser
1               5                   10

<210> SEQ ID NO 15
<211> LENGTH: 7
<212> TYPE: PRT
<213> ORGANISM: Artificial Sequence
<220> FEATURE:
<223> OTHER INFORMATION: CDR-L2
```

```
<400> SEQUENCE: 15

Gln Ala Ser Lys Leu Ala Ser
1               5

<210> SEQ ID NO 16
<211> LENGTH: 10
<212> TYPE: PRT
<213> ORGANISM: Artificial Sequence
<220> FEATURE:
<223> OTHER INFORMATION: CDR-L3

<400> SEQUENCE: 16

Ala Gly Gly Tyr Thr Ala Ser Ile Tyr Ala
1               5                   10

<210> SEQ ID NO 17
<211> LENGTH: 118
<212> TYPE: PRT
<213> ORGANISM: Artificial Sequence
<220> FEATURE:
<221> NAME/KEY: REGION
<222> LOCATION: 1..29
<223> OTHER INFORMATION: HFR1
<220> FEATURE:
<223> OTHER INFORMATION: vH
<220> FEATURE:
<221> NAME/KEY: REGION
<222> LOCATION: 30..35
<223> OTHER INFORMATION: CDR-H1
<220> FEATURE:
<221> NAME/KEY: REGION
<222> LOCATION: 36..49
<223> OTHER INFORMATION: HFR2
<220> FEATURE:
<221> NAME/KEY: REGION
<222> LOCATION: 50..66
<223> OTHER INFORMATION: CDR-H2
<220> FEATURE:
<221> NAME/KEY: REGION
<222> LOCATION: 67..97
<223> OTHER INFORMATION: HFR3
<220> FEATURE:
<221> NAME/KEY: REGION
<222> LOCATION: 98..107
<223> OTHER INFORMATION: CDR-H3
<220> FEATURE:
<221> NAME/KEY: REGION
<222> LOCATION: 108..118
<223> OTHER INFORMATION: HFR4

<400> SEQUENCE: 17

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Gly Tyr
                20                  25                  30

Asp Met Cys Trp Val Arg Gln Ala Pro Gly Lys Gly Leu Glu Trp Ile
            35                  40                  45

Ala Cys Ile Asp Thr Asp Asn Asp Ala Thr Tyr Tyr Ala Ser Trp Ala
        50                  55                  60

Lys Gly Arg Phe Thr Ile Ser Lys Pro Ser Ser Thr Val Leu Leu
65                  70                  75                  80

Gln Ile Thr Ser Leu Thr Ala Ala Asp Thr Ala Thr Tyr Phe Cys Ala
                85                  90                  95

Thr Thr His Gly Asp Tyr Val Ala Phe Lys Leu Trp Gly Pro Gly Thr
            100                 105                 110

Leu Val Thr Val Ser Ser
        115
```

```
<210> SEQ ID NO 18
<211> LENGTH: 110
<212> TYPE: PRT
<213> ORGANISM: Artificial Sequence
<220> FEATURE:
<221> NAME/KEY: REGION
<222> LOCATION: 1..22
<223> OTHER INFORMATION: LFR1
<220> FEATURE:
<223> OTHER INFORMATION: vL
<220> FEATURE:
<221> NAME/KEY: REGION
<222> LOCATION: 23..35
<223> OTHER INFORMATION: CDR-L1
<220> FEATURE:
<221> NAME/KEY: REGION
<222> LOCATION: 36..50
<223> OTHER INFORMATION: LFR2
<220> FEATURE:
<221> NAME/KEY: REGION
<222> LOCATION: 51..57
<223> OTHER INFORMATION: CDR-L2
<220> FEATURE:
<221> NAME/KEY: REGION
<222> LOCATION: 58..89
<223> OTHER INFORMATION: LFR3
<220> FEATURE:
<221> NAME/KEY: REGION
<222> LOCATION: 90..99
<223> OTHER INFORMATION: CDR-L3
<220> FEATURE:
<221> NAME/KEY: REGION
<222> LOCATION: 100..110
<223> OTHER INFORMATION: LFR4

<400> SEQUENCE: 18

Gln Val Leu Thr Gln Thr Ala Ser Ser Val Ser Ala Ala Val Gly Gly
1               5                   10                  15

Thr Val Thr Ile Asn Cys Gln Ser Ser Gln Ser Val Tyr Lys Asn Asn
            20                  25                  30

Asp Leu Ser Trp Tyr Gln Gln Lys Pro Arg Gln Pro Pro Lys Leu Leu
        35                  40                  45

Ile Tyr Gln Ala Ser Lys Leu Ala Ser Gly Val Pro Ser Arg Phe Lys
    50                  55                  60

Gly Ser Gly Ser Gly Thr Gln Phe Thr Leu Thr Ile Gly Asp Leu Glu
65                  70                  75                  80

Cys Asp Asp Gly Ala Thr Tyr Tyr Cys Ala Gly Gly Tyr Thr Ala Ser
                85                  90                  95

Ile Tyr Ala Phe Gly Gly Gly Thr Glu Val Val Val Lys Gly
            100                 105                 110

<210> SEQ ID NO 19
<211> LENGTH: 460
<212> TYPE: PRT
<213> ORGANISM: Artificial Sequence
<220> FEATURE:
<223> OTHER INFORMATION: heavy chain (145-12)
<220> FEATURE:
<221> NAME/KEY: REGION
<222> LOCATION: 20..137
<223> OTHER INFORMATION: vH

<400> SEQUENCE: 19

Met Glu Thr Gly Leu Arg Trp Leu Leu Leu Val Ala Val Phe Lys Gly
1               5                   10                  15

Ser Gln Cys Gln Ser Leu Glu Glu Ser Gly Gly Asp Leu Val Lys Pro
            20                  25                  30
```

-continued

Gly Ala Ser Leu Thr Leu Thr Cys Thr Ala Ser Gly Phe Ser Phe Ser
            35                  40                  45
Ser Gly Tyr Asp Met Cys Trp Val Arg Gln Ala Pro Gly Lys Gly Leu
 50                  55                  60
Glu Trp Ile Ala Cys Ile Asp Thr Asp Asn Asp Ala Thr Tyr Tyr Ala
65                  70                  75                  80
Ser Trp Ala Lys Gly Arg Phe Thr Ile Ser Lys Pro Ser Ser Thr Thr
                85                  90                  95
Val Leu Leu Gln Ile Thr Ser Leu Thr Ala Ala Asp Thr Ala Thr Tyr
                100                 105                 110
Phe Cys Ala Thr Thr His Gly Asp Tyr Val Ala Phe Lys Leu Trp Gly
            115                 120                 125
Pro Gly Thr Leu Val Thr Val Ser Ser Gly Gln Pro Lys Ala Pro Ser
            130                 135                 140
Val Phe Pro Leu Ala Pro Cys Cys Gly Asp Thr Pro Ser Ser Thr Val
145                 150                 155                 160
Thr Leu Gly Cys Leu Val Lys Gly Tyr Leu Pro Glu Pro Val Thr Val
                165                 170                 175
Thr Trp Asn Ser Gly Thr Leu Thr Asn Gly Val Arg Thr Phe Pro Ser
                180                 185                 190
Val Arg Gln Ser Ser Gly Leu Tyr Ser Leu Ser Ser Val Val Ser Val
                195                 200                 205
Thr Ser Ser Ser Gln Pro Val Thr Cys Asn Val Ala His Pro Ala Thr
            210                 215                 220
Asn Thr Lys Val Asp Lys Thr Val Ala Pro Ser Thr Cys Ser Lys Pro
225                 230                 235                 240
Thr Cys Pro Pro Pro Glu Leu Leu Gly Gly Pro Ser Val Phe Ile Phe
                245                 250                 255
Pro Pro Lys Pro Lys Asp Thr Leu Met Ile Ser Arg Thr Pro Glu Val
                260                 265                 270
Thr Cys Val Val Val Asp Val Ser Gln Asp Asp Pro Glu Val Gln Phe
                275                 280                 285
Thr Trp Tyr Ile Asn Asn Glu Gln Val Arg Thr Ala Arg Pro Pro Leu
            290                 295                 300
Arg Glu Gln Gln Phe Asn Ser Thr Ile Arg Val Val Ser Thr Leu Pro
305                 310                 315                 320
Ile Ala His Gln Asp Trp Leu Arg Gly Lys Glu Phe Lys Cys Lys Val
                325                 330                 335
His Asn Lys Ala Leu Pro Ala Pro Ile Glu Lys Thr Ile Ser Lys Ala
            340                 345                 350
Arg Gly Gln Pro Leu Glu Pro Lys Val Tyr Thr Met Gly Pro Pro Arg
            355                 360                 365
Glu Glu Leu Ser Ser Arg Ser Val Ser Leu Thr Cys Met Ile Asn Gly
            370                 375                 380
Phe Tyr Pro Ser Asp Ile Ser Val Glu Trp Glu Lys Asn Gly Lys Ala
385                 390                 395                 400
Glu Asp Asn Tyr Lys Thr Thr Pro Ala Val Leu Asp Ser Asp Gly Ser
                405                 410                 415
Tyr Phe Leu Tyr Ser Lys Leu Ser Val Pro Thr Ser Glu Trp Gln Arg
            420                 425                 430

```
Gly Asp Val Phe Thr Cys Ser Val Met His Glu Ala Leu His Asn His
            435                 440                 445

Tyr Thr Gln Lys Ser Ile Ser Arg Ser Pro Gly Lys
    450                 455                 460

<210> SEQ ID NO 20
<211> LENGTH: 236
<212> TYPE: PRT
<213> ORGANISM: Artificial Sequence
<220> FEATURE:
<223> OTHER INFORMATION: light chain (145-12)
<220> FEATURE:
<221> NAME/KEY: REGION
<222> LOCATION: 24..133
<223> OTHER INFORMATION: vL

<400> SEQUENCE: 20

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Ser
                20                  25                  30

Val Ser Ala Ala Val Gly Gly Thr Val Thr Ile Asn Cys Gln Ser Ser
            35                  40                  45

Gln Ser Val Tyr Lys Asn Asn Asp Leu Ser Trp Tyr Gln Gln Lys Pro
    50                  55                  60

Arg Gln Pro Pro Lys Leu Leu Ile Tyr Gln Ala Ser Lys Leu Ala Ser
65                  70                  75                  80

Gly Val Pro Ser Arg Phe Lys Gly Ser Gly Ser Gly Thr Gln Phe Thr
                85                  90                  95

Leu Thr Ile Gly Asp Leu Glu Cys Asp Asp Gly Ala Thr Tyr Tyr Cys
            100                 105                 110

Ala Gly Gly Tyr Thr Ala Ser Ile Tyr Ala Phe Gly Gly Gly Thr Glu
            115                 120                 125

Val Val Val Lys Gly Asp Pro Val Ala Pro Thr Val Leu Ile Phe Pro
            130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
            195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235

<210> SEQ ID NO 21
<211> LENGTH: 1389
<212> TYPE: DNA
<213> ORGANISM: Artificial Sequence
<220> FEATURE:
<223> OTHER INFORMATION: heavy chain (119-1)

<400> SEQUENCE: 21
atggagactg ggctgcgctg gcttctcctg gtcgctgtgc tcaaaggtgt ccagtgtcag      60
tcgttggagg agtccggggg agacctggtc aagcctggag gaaccctgac actcacctgc     120
```

| | |
|---|---|
| acaacctctg gattctcctt cagtgaccat tactggatgt gctgggtgcg ccaggctcca | 180 |
| gggaagggc tggagtggat cgcatgcatt tatactgctg atagtgactc ttactacgcg | 240 |
| agctgggcga aaggccgatt caccatctcc aagacctcgt cgaccacggt gactctgcaa | 300 |
| atgaccagtc tgacagccgc ggacacggcc acctatttct gtgcgcggaa tggtgcttat | 360 |
| gctggtggtc cttatgggga cttgtgggc ccaggcaccc tggtcaccgt ctcctcaggg | 420 |
| caacctaagg ctccatcagt cttcccactg gccccctgct gcggggacac acccagctcc | 480 |
| acggtgaccc tgggctgcct ggtcaaaggg tacctcccgg agccagtgac cgtgacctgg | 540 |
| aactcgggca ccctcaccaa tggggtacgc accttcccgt ccgtccggca gtcctcaggc | 600 |
| ctctactcgc tgagcagcgt ggtgagcgtg acctcaagca gccagcccgt cacctgcaac | 660 |
| gtggcccacc cagccaccaa caccaaagtg gacaagaccg ttgcgccctc gacatgcagc | 720 |
| aagcccacgt gcccaccccc tgaactcctg ggggaccgt ctgtcttcat cttcccccca | 780 |
| aaacccaagg acaccctcat gatctcacgc accccgagg tcacatgcgt ggtggtggac | 840 |
| gtgagccagg atgaccccga ggtgcagttc acatggtaca taaacaacga gcaggtgcgc | 900 |
| accgcccggc cgccgctacg ggagcagcag ttcaacagca cgatccgcgt ggtcagcacc | 960 |
| ctccccatcg cgcaccagga ctggctgagg ggcaaggagt tcaagtgcaa agtccacaac | 1020 |
| aaggcactcc cggccccat cgagaaaacc atctccaaag ccagagggca gcccctggag | 1080 |
| ccgaaggtct acaccatggg ccctcccgg gaggagctga gcagcaggtc ggtcagcctg | 1140 |
| acctgcatga tcaacggctt ctaccttcc gacatctcgg tggagtggga gaagaacggg | 1200 |
| aaggcagagg acaactacaa gaccacgccg gccgtgctgg acagcgacgg ctcctacttc | 1260 |
| ctctacagca agctctcagt gcccacgagt gagtggcagc ggggcgacgt cttcacctgc | 1320 |
| tccgtgatgc acgaggcctt gcacaaccac tacacgcaga gtccatctc ccgctctccg | 1380 |
| ggtaaatga | 1389 |

<210> SEQ ID NO 22
<211> LENGTH: 720
<212> TYPE: DNA
<213> ORGANISM: Artificial Sequence
<220> FEATURE:
<223> OTHER INFORMATION: light chain (119-1)

<400> SEQUENCE: 22

| | |
|---|---|
| atggacacga gggcccccac tcagctgctg gggctcctac tgctctggct cccaggtgcc | 60 |
| agatgtgctg acattgtgat gacccagact ccatcctccg tggaggcagc tgtgggaggc | 120 |
| acagtcacca tcaagtgcca ggccagtcag agcattagga cttcattagt ctggtatcag | 180 |
| cagaaaccag ggcagcctcc caagctcctg atctacaagg catccgatct gcatctgggg | 240 |
| gtcccatcgc ggttcaaggg cagtggatct gggacacagt tcactctcac catcagcgac | 300 |
| ctggagtgtg ccgatgctgc cacttactac tgtcaaagct atgattttcg cgatactatt | 360 |
| aacaatggcc attctttcgg cggagggacc gaggtggtgg tcaaaggtga tccagttgca | 420 |
| cctactgtcc tcatcttccc accagctgct gatcaggtgg caactggaac agtcaccatc | 480 |
| gtgtgtgtgg cgaataaata ctttcccgat gtcaccgtca cctgggaggt ggatggcacc | 540 |
| acccaaacaa ctggcatcga gaacagtaaa acaccgcaga attctgcaga ttgtacctac | 600 |
| aacctcagca gcactctgac actgaccagc acacagtaca cagccacaa agagtacacc | 660 |
| tgcaaggtga cccagggcac gacctcagtc gtccagagct tcaatagggg tgactgttag | 720 |

<210> SEQ ID NO 23
<211> LENGTH: 1383
<212> TYPE: DNA
<213> ORGANISM: Artificial Sequence
<220> FEATURE:
<223> OTHER INFORMATION: heavy chain (145-12)

<400> SEQUENCE: 23

| | |
|---|---|
| atggagactg ggctgcgctg gcttctcctg gtcgctgtgt tcaaaggttc ccagtgtcag | 60 |
| tcgttggagg agtccggggg agacctggtc aagcctgggg catccctgac actcacctgc | 120 |
| acagcctctg gattctcctt cagtagcggc tacgacatgt gctgggtccg ccaggctcca | 180 |
| gggaaggggc tggagtggat cgcatgcatt gatactgata tgatgccac ttactacgcg | 240 |
| agttgggcga aaggccgatt caccatctcc aaaccctcgt cgaccacggt gcttctgcag | 300 |
| ataaccagtc tgacagccgc ggacacggcc acctatttct gtgcgacaac tcatggtgat | 360 |
| tatgtggcgt ttaagttgtg gggcccaggc accctggtca ccgtctcctc agggcaacct | 420 |
| aaggctccat cagtcttccc actggccccc tgctgcgggg acacaccag ctccacggtg | 480 |
| accctgggct gcctggtcaa agggtacctc ccggagccag tgaccgtgac ctggaactcg | 540 |
| ggcaccctca ccaatggggt acgcaccttc ccgtccgtcc ggcagtcctc aggcctctac | 600 |
| tcgctgagca gcgtggtgag cgtgacctca agcagccagc ccgtcacctg caacgtggcc | 660 |
| cacccagcca acaccaa gtggacaag ccgttgcgc cctcgacatg cagcaagccc | 720 |
| acgtgcccac cccctgaact cctgggggga ccgtctgtct tcatcttccc cccaaaaccc | 780 |
| aaggacaccc tcatgatctc acgcaccccc gaggtcacat gcgtggtggt ggacgtgagc | 840 |
| caggatgacc ccgaggtgca gttcacatgg tacataaaca acgagcaggt gcgcaccgcc | 900 |
| cggccgccgc tacgggagca gcagttcaac agcacgatcc gcgtggtcag caccctcccc | 960 |
| atcgcgcacc aggactggct gaggggcaag gagttcaagt gcaaagtcca caacaaggca | 1020 |
| ctcccggccc ccatcgagaa aaccatctcc aaagccagag gcagcccct ggagccgaag | 1080 |
| gtctacacca tgggccctcc ccgggaggag ctgagcagca ggtcggtcag cctgacctgc | 1140 |
| atgatcaacg gcttctaccc ttccgacatc tcggtggagt gggagaagaa cgggaaggca | 1200 |
| gaggacaact acaagaccac gccggccgtg ctggacagcg acggctccta cttcctctac | 1260 |
| agcaagctct cagtgcccac gagtgagtgg cagcggggcg acgtcttcac ctgctccgtg | 1320 |
| atgcacgagg ccttgcacaa ccactacacg cagaagtcca tctcccgctc tccgggtaaa | 1380 |
| tga | 1383 |

<210> SEQ ID NO 24
<211> LENGTH: 711
<212> TYPE: DNA
<213> ORGANISM: Artificial Sequence
<220> FEATURE:
<223> OTHER INFORMATION: light chain (145-12)

<400> SEQUENCE: 24

| | |
|---|---|
| atggacacga gggcccccac tcagctgctg gggctcctgc tgctctggct cccaggtgcc | 60 |
| acatttgcgc aagtgctgac ccagactgca tcgtccgtgt ctgcagctgt gggaggcaca | 120 |
| gtcaccatca attgccagtc cagtcagagt gtttataaga caacgactt atcctggtat | 180 |
| cagcagaaac caaggcagcc tcccaagctc ctgatctacc aggcatccaa actggcatct | 240 |
| ggggtcccat cgcggttcaa aggcagtgga tctgggacac agttcactct caccatcggc | 300 |
| gacctggagt gtgacgatgg tgccacttac tactgtgcag gcggttatac tgctagtatt | 360 |

| | | |
|---|---|---|
| tatgctttcg gcggagggac cgaggtggtg gtcaaggtg atccagttgc acctactgtc | 420 | |
| ctcatcttcc caccagctgc tgatcaggtg gcaactggaa cagtcaccat cgtgtgtgtg | 480 | |
| gcgaataaat actttcccga tgtcaccgtc acctgggagg tggatggcac cacccaaaca | 540 | |
| actggcatcg agaacagtaa aacaccgcag aattctgcag attgtaccta caacctcagc | 600 | |
| agcactctga cactgaccag cacacagtac aacagccaca agagtacac ctgcaaggtg | 660 | |
| acccagggca cgacctcagt cgtccagagc ttcaataggg gtgactgtta g | 711 | |

```
<210> SEQ ID NO 25
<211> LENGTH: 202
<212> TYPE: PRT
<213> ORGANISM: Artificial Sequence
<220> FEATURE:
<223> OTHER INFORMATION: fusion protein CD95L-AT4 (APG293)

<400> SEQUENCE: 25
```

Glu Leu Arg Lys Val Ala His Leu Thr Gly Lys Ser Asn Ser Arg Ser
1               5                   10                  15

Met Pro Leu Glu Trp Glu Asp Thr Tyr Gly Ile Val Leu Leu Ser Gly
            20                  25                  30

Val Lys Tyr Lys Lys Gly Gly Leu Val Ile Asn Glu Thr Gly Leu Tyr
        35                  40                  45

Phe Val Tyr Ser Lys Val Tyr Phe Arg Gly Gln Ser Cys Asn Asn Leu
    50                  55                  60

Pro Leu Ser His Lys Val Tyr Met Arg Asn Ser Lys Tyr Pro Gln Asp
65                  70                  75                  80

Leu Val Met Met Glu Gly Lys Met Met Ser Tyr Cys Thr Thr Gly Gln
                85                  90                  95

Met Trp Ala Arg Ser Ser Tyr Leu Gly Ala Val Phe Asn Leu Thr Ser
            100                 105                 110

Ala Asp His Leu Tyr Val Asn Val Ser Glu Leu Ser Leu Val Asn Phe
        115                 120                 125

Glu Glu Ser Gln Thr Phe Phe Gly Leu Tyr Lys Leu Gly Ser Ser Gly
    130                 135                 140

Ser Ser Gly Ser Ser Gly Ser Gly Tyr Ile Pro Glu Ala Pro Arg Asp
145                 150                 155                 160

Gly Gln Ala Tyr Val Arg Lys Asp Gly Glu Trp Val Leu Leu Ser Thr
                165                 170                 175

Phe Leu Ser Gly Pro Ser Ser Ser Ser His His His His His
            180                 185                 190

Ser Ala Trp Ser His Pro Gln Phe Glu Lys
            195                 200

```
<210> SEQ ID NO 26
<211> LENGTH: 195
<212> TYPE: PRT
<213> ORGANISM: Artificial Sequence
<220> FEATURE:
<223> OTHER INFORMATION: fusion protein CD95L-RB96 (APG296)

<400> SEQUENCE: 26
```

Glu Leu Arg Lys Val Ala His Leu Thr Gly Lys Ser Asn Ser Arg Ser
1               5                   10                  15

Met Pro Leu Glu Trp Glu Asp Thr Tyr Gly Ile Val Leu Leu Ser Gly
            20                  25                  30

Val Lys Tyr Lys Lys Gly Gly Leu Val Ile Asn Glu Thr Gly Leu Tyr
        35                  40                  45

```
Phe Val Tyr Ser Lys Val Tyr Phe Arg Gly Gln Ser Cys Asn Asn Leu
    50                  55                  60

Pro Leu Ser His Lys Val Tyr Met Arg Asn Ser Lys Tyr Pro Gln Asp
 65                  70                  75                  80

Leu Val Met Met Glu Gly Lys Met Met Ser Tyr Cys Thr Thr Gly Gln
                     85                  90                  95

Met Trp Ala Arg Ser Ser Tyr Leu Gly Ala Val Phe Asn Leu Thr Ser
                100                 105                 110

Ala Asp His Leu Tyr Val Asn Val Ser Glu Leu Ser Leu Val Asn Phe
                115                 120                 125

Glu Glu Ser Gln Thr Phe Phe Gly Leu Tyr Lys Leu Gly Ser Ser Gly
    130                 135                 140

Ser Ser Gly Ser Ser Gly Ser Gly Tyr Ile Glu Asp Ala Pro Ser Asp
145                 150                 155                 160

Gly Lys Phe Tyr Val Arg Lys Asp Gly Ala Trp Val Glu Leu Pro Thr
                165                 170                 175

Ala Ser Gly Pro Ser Ser Ser Ser Ser Ala Trp Ser His Pro Gln
                180                 185                 190

Phe Glu Lys
    195

<210> SEQ ID NO 27
<211> LENGTH: 205
<212> TYPE: PRT
<213> ORGANISM: Artificial Sequence
<220> FEATURE:
<223> OTHER INFORMATION: LIGHT-RB69 (APG707)

<400> SEQUENCE: 27

Glu Val Asn Pro Ala Ala His Leu Thr Gly Ala Asn Ser Ser Leu Thr
 1               5                  10                  15

Gly Ser Gly Gly Pro Leu Leu Trp Glu Thr Gln Leu Gly Leu Ala Phe
                 20                  25                  30

Leu Arg Gly Leu Ser Tyr His Asp Gly Ala Leu Val Val Thr Lys Ala
                 35                  40                  45

Gly Tyr Tyr Tyr Ile Tyr Ser Lys Val Gln Leu Gly Gly Val Gly Cys
    50                  55                  60

Pro Leu Gly Leu Ala Ser Thr Ile Thr His Gly Leu Tyr Lys Arg Thr
 65                  70                  75                  80

Pro Arg Tyr Pro Glu Glu Leu Glu Leu Leu Val Ser Gln Gln Ser Pro
                 85                  90                  95

Cys Gly Arg Ala Thr Ser Ser Ser Arg Val Trp Trp Asp Ser Ser Phe
                100                 105                 110

Leu Gly Gly Val Val His Leu Glu Ala Gly Glu Glu Val Val Val Arg
                115                 120                 125

Val Leu Asp Glu Arg Leu Val Arg Leu Arg Asp Gly Thr Arg Ser Tyr
    130                 135                 140

Phe Gly Ala Phe Met Val Gly Ser Gly Ser Ser Gly Ser Ser Gly Ser
145                 150                 155                 160

Ser Gly Tyr Ile Glu Asp Ala Pro Ser Asp Gly Lys Phe Tyr Val Arg
                165                 170                 175

Lys Asp Gly Ala Trp Val Glu Leu Pro Thr Ala Ser Gly Pro Ser Ser
                180                 185                 190

Ser Ser Ser Ala Trp Ser His Pro Gln Phe Glu Lys
    195                 200                 205
```

<210> SEQ ID NO 28
<211> LENGTH: 195
<212> TYPE: PRT
<213> ORGANISM: Artificial Sequence Sequence
<220> FEATURE:
<223> OTHER INFORMATION: monkey CD95L-RB69 (APG1249)

<400> SEQUENCE: 28

```
Glu Gln Arg Lys Val Ala His Leu Thr Gly Lys Pro Asn Ser Arg Ser
1               5                   10                  15

Met Pro Leu Glu Trp Glu Asp Thr Tyr Gly Ile Val Leu Leu Ser Gly
            20                  25                  30

Val Lys Tyr Lys Lys Gly Gly Leu Val Ile Asn Glu Thr Gly Leu Tyr
        35                  40                  45

Phe Val Tyr Ser Lys Val Tyr Phe Arg Gly Gln Ser Cys Thr Asn Leu
    50                  55                  60

Pro Leu Ser His Lys Val Tyr Met Arg Asn Ser Lys Tyr Pro Gln Asp
65                  70                  75                  80

Leu Val Met Met Glu Gly Lys Met Met Ser Tyr Cys Thr Thr Gly Gln
                85                  90                  95

Met Trp Ala His Ser Ser Tyr Leu Gly Ala Val Phe Asn Leu Thr Ser
            100                 105                 110

Ala Asp His Leu Tyr Val Asn Val Ser Glu Leu Ser Leu Val Asn Phe
        115                 120                 125

Glu Glu Ser Gln Thr Phe Phe Gly Leu Tyr Lys Leu Gly Ser Ser Gly
    130                 135                 140

Ser Ser Gly Ser Gly Ser Gly Tyr Ile Glu Asp Ala Pro Ser Asp
145                 150                 155                 160

Gly Lys Phe Tyr Val Arg Lys Asp Gly Ala Trp Val Glu Leu Pro Thr
                165                 170                 175

Ala Ser Gly Pro Ser Ser Ser Ser Ser Ala Trp Ser His Pro Gln
            180                 185                 190

Phe Glu Lys
        195
```

<210> SEQ ID NO 29
<211> LENGTH: 195
<212> TYPE: PRT
<213> ORGANISM: Artificial Sequence Sequence
<220> FEATURE:
<223> OTHER INFORMATION: mouse CD95L-RB69 (APG1250)

<400> SEQUENCE: 29

```
Glu Leu Arg Ser Val Ala His Leu Thr Gly Asn Pro His Ser Arg Ser
1               5                   10                  15

Ile Pro Leu Glu Trp Glu Asp Thr Tyr Gly Thr Ala Leu Ile Ser Gly
            20                  25                  30

Val Lys Tyr Lys Lys Gly Gly Leu Val Ile Asn Glu Thr Gly Leu Tyr
        35                  40                  45

Phe Val Tyr Ser Lys Val Tyr Phe Arg Gly Gln Ser Cys Asn Asn Gln
    50                  55                  60

Pro Leu Asn His Lys Val Tyr Met Arg Asn Ser Lys Tyr Pro Glu Asp
65                  70                  75                  80

Leu Val Leu Met Glu Glu Lys Arg Leu Asn Tyr Cys Thr Thr Gly Gln
                85                  90                  95

Ile Trp Ala His Ser Ser Tyr Leu Gly Ala Val Phe Asn Leu Thr Ser
            100                 105                 110
```

Ala Asp His Leu Tyr Val Asn Ile Ser Gln Leu Ser Leu Ile Asn Phe
          115                 120                 125

Glu Glu Ser Lys Thr Phe Phe Gly Leu Tyr Lys Leu Gly Ser Ser Gly
        130                 135                 140

Ser Ser Gly Ser Ser Gly Ser Gly Tyr Ile Glu Asp Ala Pro Ser Asp
145                 150                 155                 160

Gly Lys Phe Tyr Val Arg Lys Asp Gly Ala Trp Val Glu Leu Pro Thr
                165                 170                 175

Ala Ser Gly Pro Ser Ser Ser Ser Ser Ala Trp Ser His Pro Gln
                180                 185                 190

Phe Glu Lys
      195

<210> SEQ ID NO 30
<211> LENGTH: 120
<212> TYPE: PRT
<213> ORGANISM: Artificial Sequence
<220> FEATURE:
<223> OTHER INFORMATION: VH_hu145_12_A

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Asp Met Cys Trp Val Arg Gln Ala Pro Gly Lys Gly Leu Glu Trp
        35                  40                  45

Val Ala Cys Ile Asp Thr Asp Asn Asp Ala Thr Tyr Tyr Ala Ser Trp
50                  55                  60

Ala Lys Gly Arg Phe Thr Ile Ser Lys Asp Ser Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Thr His Gly Asp Tyr Val Ala Phe Lys Leu Trp Gly Gln
            100                 105                 110

Gly Thr Leu Val Thr Val Ser Ser
        115                 120

<210> SEQ ID NO 31
<211> LENGTH: 120
<212> TYPE: PRT
<213> ORGANISM: Artificial Sequence
<220> FEATURE:
<223> OTHER INFORMATION: VH_hu145_12_B

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Asp Met Cys Trp Val Arg Gln Ala Pro Gly Lys Gly Leu Glu Trp
        35                  40                  45

Val Ala Cys Ile Asp Thr Asp Asn Asp Ala Thr Tyr Tyr Ala Asp Ser
50                  55                  60

Val Lys Gly Arg Phe Thr Ile Ser Lys Asp Ser Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Thr His Gly Asp Tyr Val Ala Phe Lys Leu Trp Gly Gln
            100                 105                 110

Gly Thr Leu Val Thr Val Ser Ser
        115                 120

<210> SEQ ID NO 32
<211> LENGTH: 120
<212> TYPE: PRT
<213> ORGANISM: Artificial Sequence
<220> FEATURE:
<223> OTHER INFORMATION: VH_hu145_12_C

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Asp Met Ser Trp Val Arg Gln Ala Pro Gly Lys Gly Leu Glu Trp
        35                  40                  45

Val Ser Ala Ile Asp Thr Asp Asn Asp Ala Thr Tyr Tyr Ala Asp Ser
50                  55                  60

Val Lys Gly Arg Phe Thr Ile Ser Lys Asp Ser Ser Lys Asn Thr Leu
65                  70                  75                  80

Tyr Leu Gln Met Asn Ser Leu Arg Ala Glu Asp Thr Ala Val Tyr Tyr
            85                  90                  95

Cys Ala Arg Thr His Gly Asp Tyr Val Ala Phe Lys Leu Trp Gly Gln
            100                 105                 110

Gly Thr Leu Val Thr Val Ser Ser
        115                 120

<210> SEQ ID NO 33
<211> LENGTH: 111
<212> TYPE: PRT
<213> ORGANISM: Artificial Sequence
<220> FEATURE:
<223> OTHER INFORMATION: VL_hu145_12

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Tyr Lys Asn
            20                  25                  30

Asn Asp Leu Ser Trp Tyr Gln Gln Lys Pro Gly Lys Ala Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Ala Gly Gly Tyr Thr Ala
            85                  90                  95

Ser Ile Tyr Ala Phe Gly Gln Gly Thr Lys Val Glu Ile Lys Arg
        100                 105                 110

<210> SEQ ID NO 34
<211> LENGTH: 450
<212> TYPE: PRT
<213> ORGANISM: Artificial Sequence
<220> FEATURE:
<223> OTHER INFORMATION: HC_hu145_12_N297S

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Asp Met Cys Trp Val Arg Gln Ala Pro Gly Lys Gly Leu Glu Trp
        35                  40                  45

Val Ala Cys Ile Asp Thr Asp Asn Asp Ala Thr Tyr Tyr Ala Asp Ser
50                  55                  60

Val Lys Gly Arg Phe Thr Ile Ser Lys Asp Ser Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Thr His Gly Asp Tyr Val Ala Phe Lys Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ser Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 35
<211> LENGTH: 450
<212> TYPE: PRT
<213> ORGANISM: Artificial Sequence
<220> FEATURE:
<223> OTHER INFORMATION: HC_hu145_12

<400> SEQUENCE: 35

Glu Val Gln Leu Val Glu Ser Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Asp Met Cys Trp Val Arg Gln Ala Pro Gly Lys Gly Leu Glu Trp
            35                  40                  45

Val Ala Cys Ile Asp Thr Asp Asn Asp Ala Thr Tyr Tyr Ala Asp Ser
50                  55                  60

Val Lys Gly Arg Phe Thr Ile Ser Lys Asp Ser Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Thr His Gly Asp Tyr Val Ala Phe Lys Leu Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 36
<211> LENGTH: 217
<212> TYPE: PRT
<213> ORGANISM: Artificial Sequence
<220> FEATURE:
<223> OTHER INFORMATION: LC_hu145_12

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Tyr Lys Asn
            20                  25                  30

Asn Asp Leu Ser Trp Tyr Gln Gln Lys Pro Gly Lys Ala Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Ala Gly Gly Tyr Thr Ala
                85                  90                  95

Ser Ile Tyr Ala Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

```
<210> SEQ ID NO 37
<211> LENGTH: 366
<212> TYPE: PRT
<213> ORGANISM: Artificial Sequence
<220> FEATURE:
<223> OTHER INFORMATION: MB_145_12

<400> SEQUENCE: 37
```

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Gly Tyr
            20                  25                  30

Asp Met Cys Trp Val Arg Gln Ala Pro Gly Lys Gly Leu Glu Trp Ile
        35                  40                  45

Ala Cys Ile Asp Thr Asp Asn Asp Ala Thr Tyr Tyr Ala Ser Trp Ala
    50                  55                  60

Lys Gly Arg Phe Thr Ile Ser Lys Pro Ser Ser Thr Thr Val Leu Leu
65                  70                  75                  80

Gln Ile Thr Ser Leu Thr Ala Ala Asp Thr Ala Thr Tyr Phe Cys Ala
                85                  90                  95

Thr Thr His Gly Asp Tyr Val Ala Phe Lys Leu Trp Gly Pro Gly Thr
            100                 105                 110

Leu Val Thr Val Ser Gly Gly Ser Gly Gly Gly Ser Gly Gly Gly
        115                 120                 125

Ser Gly Gly Gly Ser Gln Val Leu Thr Gln Thr Ala Ser Ser Val Ser
130                 135                 140

Ala Ala Val Gly Gly Thr Val Thr Ile Asn Cys Gln Ser Ser Gln Ser
145                 150                 155                 160

Val Tyr Lys Asn Asn Asp Leu Ser Trp Tyr Gln Gln Lys Pro Arg Gln
                165                 170                 175

Pro Pro Lys Leu Leu Ile Tyr Gln Ala Ser Lys Leu Ala Ser Gly Val
            180                 185                 190

Pro Ser Arg Phe Lys Gly Ser Gly Ser Gly Thr Gln Phe Thr Leu Thr
        195                 200                 205

Ile Gly Asp Leu Glu Ser Asp Asp Gly Ala Thr Tyr Tyr Cys Ala Gly
    210                 215                 220

Gly Tyr Thr Ala Ser Ile Tyr Ala Phe Gly Gly Thr Glu Val Val
225                 230                 235                 240

Gly Ser Gly Ser Ser Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Gln Gly Ser Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Ser
            340                 345                 350

Ser Ser Ser Ser Ser Ala Trp Ser His Pro Gln Phe Glu Lys
        355                 360                 365

<210> SEQ ID NO 38
<211> LENGTH: 371
<212> TYPE: PRT
<213> ORGANISM: Artificial Sequence
<220> FEATURE:
<223> OTHER INFORMATION: MB_hu145_12A

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Asp Met Cys Trp Val Arg Gln Ala Pro Gly Lys Gly Leu Glu Trp
        35                  40                  45

Val Ala Cys Ile Asp Thr Asp Asn Asp Ala Thr Tyr Tyr Ala Ser Trp
    50                  55                  60

Ala Lys Gly Arg Phe Thr Ile Ser Lys Asp Ser Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Thr His Gly Asp Tyr Val Ala Phe Lys Leu Trp Gly Gln
            100                 105                 110

Gly Thr Leu Val Thr Val Ser Gly Gly Gly Ser Gly Gly Gly Ser Gly
        115                 120                 125

Gly Gly Ser Gly Gly Gly Ser Asp Ile Gln Met Thr Gln Ser Pro Ser
    130                 135                 140

Ser Leu Ser Ala Ser Val Gly Asp Arg Val Thr Ile Thr Cys Gln Ser
145                 150                 155                 160

Ser Gln Ser Val Tyr Lys Asn Asn Asp Leu Ser Trp Tyr Gln Gln Lys
                165                 170                 175

Pro Gly Lys Ala Pro Lys Leu Leu Ile Tyr Gln Ala Ser Lys Leu Ala
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Ala Gly Gly Tyr Thr Ala Ser Ile Tyr Ala Phe Gly Gln Gly Thr
225                 230                 235                 240

Lys Val Glu Ile Lys Gly Ser Gly Ser Ser Gly Gln Pro Arg Glu Pro
                245                 250                 255

Gln Val Tyr Thr Leu Pro Pro Ser Arg Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Gln Gly Ser Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350
```

Leu Ser Pro Gly Ser Ser Ser Ser Ser Ala Trp Ser His Pro Gln
            355                 360                 365

Phe Glu Lys
    370

<210> SEQ ID NO 39
<211> LENGTH: 371
<212> TYPE: PRT
<213> ORGANISM: Artificial Sequence
<220> FEATURE:
<223> OTHER INFORMATION: MB_hu145_12B

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Asp Met Cys Trp Val Arg Gln Ala Pro Gly Lys Gly Leu Glu Trp
            35                  40                  45

Val Ala Cys Ile Asp Thr Asp Asn Asp Ala Thr Tyr Tyr Ala Asp Ser
50                  55                  60

Val Lys Gly Arg Phe Thr Ile Ser Lys Asp Ser Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Thr His Gly Asp Tyr Val Ala Phe Lys Leu Trp Gly Gln
            100                 105                 110

Gly Thr Leu Val Thr Val Ser Gly Gly Gly Ser Gly Gly Gly Ser Gly
            115                 120                 125

Gly Gly Ser Gly Gly Gly Ser Asp Ile Gln Met Thr Gln Ser Pro Ser
        130                 135                 140

Ser Leu Ser Ala Ser Val Gly Asp Arg Val Thr Ile Thr Cys Gln Ser
145                 150                 155                 160

Ser Gln Ser Val Tyr Lys Asn Asn Asp Leu Ser Trp Tyr Gln Gln Lys
                165                 170                 175

Pro Gly Lys Ala Pro Lys Leu Leu Ile Tyr Gln Ala Ser Lys Leu Ala
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Ala Gly Gly Tyr Thr Ala Ser Ile Tyr Ala Phe Gly Gln Gly Thr
225                 230                 235                 240

Lys Val Glu Ile Lys Gly Ser Gly Ser Ser Gly Gln Pro Arg Glu Pro
                245                 250                 255

Gln Val Tyr Thr Leu Pro Pro Ser Arg Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Gln Gly Ser Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

```
Val Met His Glu Ala Leu His Asn His Tyr Thr Gln Lys Ser Leu Ser
            340                 345                 350

Leu Ser Pro Gly Ser Ser Ser Ser Ser Ala Trp Ser His Pro Gln
        355                 360                 365

Phe Glu Lys
    370

<210> SEQ ID NO 40
<211> LENGTH: 371
<212> TYPE: PRT
<213> ORGANISM: Artificial Sequence
<220> FEATURE:
<223> OTHER INFORMATION: MB_hu145_12C

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Asp Met Ser Trp Val Arg Gln Ala Pro Gly Lys Gly Leu Glu Trp
        35                  40                  45

Val Ser Ala Ile Asp Thr Asp Asn Asp Ala Thr Tyr Tyr Ala Asp Ser
    50                  55                  60

Val Lys Gly Arg Phe Thr Ile Ser Lys Asp Ser Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Thr His Gly Asp Tyr Val Ala Phe Lys Leu Trp Gly Gln
            100                 105                 110

Gly Thr Leu Val Thr Val Ser Gly Gly Gly Ser Gly Gly Gly Ser Gly
        115                 120                 125

Gly Gly Ser Gly Gly Gly Ser Asp Ile Gln Met Thr Gln Ser Pro Ser
    130                 135                 140

Ser Leu Ser Ala Ser Val Gly Asp Arg Val Thr Ile Thr Cys Gln Ser
145                 150                 155                 160

Ser Gln Ser Val Tyr Lys Asn Asn Asp Leu Ser Trp Tyr Gln Gln Lys
                165                 170                 175

Pro Gly Lys Ala Pro Lys Leu Leu Ile Tyr Gln Ala Ser Lys Leu Ala
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Ala Gly Gly Tyr Thr Ala Ser Ile Tyr Ala Phe Gly Gln Gly Thr
225                 230                 235                 240

Lys Val Glu Ile Lys Gly Ser Gly Ser Ser Gly Gln Pro Arg Glu Pro
                245                 250                 255

Gln Val Tyr Thr Leu Pro Pro Ser Arg Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Gln Gly Ser Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320
```

Thr Val Asp Lys Ser Arg Trp Gln Gln Gly Asn Val Phe Ser Cys Ser
            325                 330                 335

Val Met His Glu Ala Leu His Asn His Tyr Thr Gln Lys Ser Leu Ser
            340                 345                 350

Leu Ser Pro Gly Ser Ser Ser Ser Ser Ala Trp Ser His Pro Gln
            355                 360                 365

Phe Glu Lys
    370

<210> SEQ ID NO 41
<211> LENGTH: 122
<212> TYPE: PRT
<213> ORGANISM: Artificial Sequence
<220> FEATURE:
<223> OTHER INFORMATION: VH_hu119_4_A

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp His
            20                  25                  30

Tyr Trp Met Cys Trp Val Arg Gln Ala Pro Gly Lys Gly Leu Glu Trp
        35                  40                  45

Val Ala Cys Ile Tyr Thr Ala Asp Ser Asp Ser Tyr Tyr Ala Ser Trp
    50                  55                  60

Ala Lys Gly Arg Phe Thr Ile Ser Lys Asp Ser Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asn Gly Ala Tyr Ala Gly Gly Pro Tyr Gly Asp Leu Trp
            100                 105                 110

Gly Gln Gly Thr Leu Val Thr Val Ser Ser
        115                 120

<210> SEQ ID NO 42
<211> LENGTH: 122
<212> TYPE: PRT
<213> ORGANISM: Artificial Sequence
<220> FEATURE:
<223> OTHER INFORMATION: VH_hu119_4_B

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp His
            20                  25                  30

Tyr Trp Met Cys Trp Val Arg Gln Ala Pro Gly Lys Gly Leu Glu Trp
        35                  40                  45

Val Ala Cys Ile Tyr Thr Ala Asp Ser Asp Ser Tyr Tyr Ala Asp Ser
    50                  55                  60

Val Lys Gly Arg Phe Thr Ile Ser Lys Asp Ser Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asn Gly Ala Tyr Ala Gly Gly Pro Tyr Gly Asp Leu Trp
            100                 105                 110

Gly Gln Gly Thr Leu Val Thr Val Ser Ser
        115                 120

<210> SEQ ID NO 43
<211> LENGTH: 122
<212> TYPE: PRT
<213> ORGANISM: Artificial Sequence
<220> FEATURE:
<223> OTHER INFORMATION: VH_hu119_4_C

<400> SEQUENCE: 43

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp His
            20                  25                  30

Tyr Trp Met Ser Trp Val Arg Gln Ala Pro Gly Lys Gly Leu Glu Trp
        35                  40                  45

Val Ser Ala Ile Tyr Thr Ala Asp Ser Asp Ser Tyr Tyr Ala Asp Ser
    50                  55                  60

Val Lys Gly Arg Phe Thr Ile Ser Lys Asp Ser Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asn Gly Ala Tyr Ala Gly Gly Pro Tyr Gly Asp Leu Trp
            100                 105                 110

Gly Gln Gly Thr Leu Val Thr Val Ser Ser
        115                 120
```

<210> SEQ ID NO 44
<211> LENGTH: 113
<212> TYPE: PRT
<213> ORGANISM: Artificial Sequence
<220> FEATURE:
<223> OTHER INFORMATION: VL_hu119_4

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Ile Arg Thr Ser
            20                  25                  30

Leu Val Trp Tyr Gln Gln Lys Pro Gly Lys Ala Pro Lys Leu Leu Ile
        35                  40                  45

Tyr Lys Ala Ser Asp Leu Pro Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Asp Phe Arg Asp Thr
                85                  90                  95

Ile Asn Asn Gly His Ser Phe Gly Gln Gly Thr Lys Val Glu Ile Lys
            100                 105                 110

Arg
```

<210> SEQ ID NO 45
<211> LENGTH: 455
<212> TYPE: PRT
<213> ORGANISM: Artificial Sequence
<220> FEATURE:
<223> OTHER INFORMATION: HC_hu119_4_N297S

<400> SEQUENCE: 45

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Ser Phe Ser Asp His
            20                  25                  30

Tyr Trp Met Cys Trp Val Arg Gln Ala Pro Gly Lys Gly Leu Glu Trp
            35                  40                  45

Val Ala Cys Ile Tyr Thr Ala Asp Ser Asp Ser Tyr Tyr Ala Asp Ser
    50                  55                  60

Val Lys Gly Arg Phe Thr Ile Ser Lys Asp Ser Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asn Gly Ala Tyr Ala Gly Gly Pro Tyr Gly Asp Leu Trp
            100                 105                 110

Gly Gln Gly Thr Leu Val Thr Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Ser Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415
```

```
Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450             455
```

<210> SEQ ID NO 46
<211> LENGTH: 455
<212> TYPE: PRT
<213> ORGANISM: Artificial Sequence
<220> FEATURE:
<223> OTHER INFORMATION: HC_hu119_4

<400> SEQUENCE: 46

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp His
            20                  25                  30

Tyr Trp Met Cys Trp Val Arg Gln Ala Pro Gly Lys Gly Leu Glu Trp
        35                  40                  45

Val Ala Cys Ile Tyr Thr Ala Asp Ser Asp Ser Tyr Tyr Ala Asp Ser
50                  55                  60

Val Lys Gly Arg Phe Thr Ile Ser Lys Asp Ser Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asn Gly Ala Tyr Ala Gly Gly Pro Tyr Gly Asp Leu Trp
            100                 105                 110

Gly Gln Gly Thr Leu Val Thr Val Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320
```

```
Trp Leu Asn Gly Lys Glu Tyr Lys Cys Lys Val Ser Asn Lys Ala Leu
            325                 330                 335
Pro Ala Pro Ile Glu Lys Thr Ile Ser Lys Ala Lys Gly Gln Pro Arg
        340                 345                 350
Glu Pro Gln Val Tyr Thr Leu Pro Pro Ser Arg Glu Glu Met Thr Lys
    355                 360                 365
Asn Gln Val Ser Leu Thr Cys Leu Val Lys Gly Phe Tyr Pro Ser Asp
370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys
    450                 455
```

<210> SEQ ID NO 47
<211> LENGTH: 219
<212> TYPE: PRT
<213> ORGANISM: Artificial Sequence
<220> FEATURE:
<223> OTHER INFORMATION: LC_hu119_4

<400> SEQUENCE: 47

```
Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Ser Ile Arg Thr Ser
            20                  25                  30
Leu Val Trp Tyr Gln Gln Lys Pro Gly Lys Ala Pro Lys Leu Leu Ile
        35                  40                  45
Tyr Lys Ala Ser Asp Leu Pro Ser Gly Val Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Ser Tyr Asp Phe Arg Asp Thr
                85                  90                  95
Ile Asn Asn Gly His Ser Phe Gly Gln Gly Thr Lys Val Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215
```

```
<210> SEQ ID NO 48
<211> LENGTH: 373
<212> TYPE: PRT
<213> ORGANISM: Artificial Sequence
<220> FEATURE:
<223> OTHER INFORMATION: MB_119_4

<400> SEQUENCE: 48

Gln Ser Leu Glu Glu Ser Gly Gly Asp Leu Val Lys Pro Gly Gly Thr
1               5                   10                  15

Leu Thr Leu Thr Cys Thr Thr Ser Gly Phe Ser Phe Ser Asp His Tyr
            20                  25                  30

Trp Met Cys Trp Val Arg Gln Ala Pro Gly Lys Gly Leu Glu Trp Ile
        35                  40                  45

Ala Cys Ile Tyr Thr Ala Asp Ser Asp Ser Tyr Tyr Ala Ser Trp Ala
    50                  55                  60

Lys Gly Arg Phe Thr Ile Ser Lys Thr Ser Ser Thr Val Thr Leu
65                  70                  75                  80

Gln Met Thr Ser Leu Thr Ala Ala Asp Thr Ala Thr Tyr Phe Cys Ala
                85                  90                  95

Arg Asn Gly Ala Tyr Ala Gly Gly Pro Tyr Gly Asp Leu Trp Gly Pro
            100                 105                 110

Gly Thr Leu Val Thr Val Ser Gly Gly Ser Gly Gly Ser Gly
        115                 120                 125

Gly Gly Ser Gly Gly Gly Ser Asp Ile Val Met Thr Gln Thr Pro Ser
    130                 135                 140

Ser Val Glu Ala Ala Val Gly Gly Thr Val Thr Ile Lys Cys Gln Ala
145                 150                 155                 160

Ser Gln Ser Ile Arg Thr Ser Leu Val Trp Tyr Gln Gln Lys Pro Gly
                165                 170                 175

Gln Pro Pro Lys Leu Leu Ile Tyr Lys Ala Ser Asp Leu Pro Ser Gly
            180                 185                 190

Val Pro Ser Arg Phe Lys Gly Ser Gly Ser Gly Thr Gln Phe Thr Leu
        195                 200                 205

Thr Ile Ser Asp Leu Glu Ser Ala Asp Ala Ala Thr Tyr Tyr Cys Gln
    210                 215                 220

Ser Tyr Asp Phe Arg Asp Thr Ile Asn Asn Gly His Ser Phe Gly Gly
225                 230                 235                 240

Gly Thr Glu Val Val Val Lys Gly Ser Gly Ser Ser Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Gln Gly Ser Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350
```

Leu Ser Leu Ser Pro Gly Ser Ser Ser Ser Ala Trp Ser His
            355                 360                 365

Pro Gln Phe Glu Lys
    370

<210> SEQ ID NO 49
<211> LENGTH: 375
<212> TYPE: PRT
<213> ORGANISM: Artificial Sequence
<220> FEATURE:
<223> OTHER INFORMATION: MB_hu119_4A

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp His
            20                  25                  30

Tyr Trp Met Cys Trp Val Arg Gln Ala Pro Gly Lys Gly Leu Glu Trp
        35                  40                  45

Val Ala Cys Ile Tyr Thr Ala Asp Ser Asp Ser Tyr Ala Ser Trp
    50                  55                  60

Ala Lys Gly Arg Phe Thr Ile Ser Lys Asp Ser Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asn Gly Ala Tyr Ala Gly Gly Pro Tyr Gly Asp Leu Trp
            100                 105                 110

Gly Gln Gly Thr Leu Val Thr Val Ser Gly Gly Gly Ser Gly Gly Gly
        115                 120                 125

Ser Gly Gly Gly Ser Gly Gly Gly Ser Asp Ile Gln Met Thr Gln Ser
130                 135                 140

Pro Ser Ser Leu Ser Ala Ser Val Gly Asp Arg Val Thr Ile Thr Cys
145                 150                 155                 160

Lys Ala Ser Gln Ser Ile Arg Thr Ser Leu Val Trp Tyr Gln Gln Lys
                165                 170                 175

Pro Gly Lys Ala Pro Lys Leu Leu Ile Tyr Lys Ala Ser Asp Leu Pro
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Ser Tyr Asp Phe Arg Asp Thr Ile Asn Asn Gly His Ser Phe
225                 230                 235                 240

Gly Gln Gly Thr Lys Val Glu Ile Lys Gly Ser Gly Ser Ser Gly Gln
                245                 250                 255

Pro Arg Glu Pro Gln Val Tyr Thr Leu Pro Pro Ser Arg Glu Glu Met
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Gln Gly Ser Pro Glu Asn Asn
    290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

```
Phe Ser Cys Ser Val Met His Glu Ala Leu His Asn His Tyr Thr Gln
                340                 345                 350
Lys Ser Leu Ser Leu Ser Pro Gly Ser Ser Ser Ser Ser Ala Trp
        355                 360                 365
Ser His Pro Gln Phe Glu Lys
        370                 375

<210> SEQ ID NO 50
<211> LENGTH: 375
<212> TYPE: PRT
<213> ORGANISM: Artificial Sequence
<220> FEATURE:
<223> OTHER INFORMATION: MB_hu119_4B

<400> SEQUENCE: 50

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Ser Phe Ser Asp His
            20                  25                  30
Tyr Trp Met Cys Trp Val Arg Gln Ala Pro Gly Lys Gly Leu Glu Trp
        35                  40                  45
Val Ala Cys Ile Tyr Thr Ala Asp Ser Asp Ser Tyr Tyr Ala Asp Ser
 50                  55                  60
Val Lys Gly Arg Phe Thr Ile Ser Lys Asp Ser Ser Lys Asn Thr Leu
65                  70                  75                  80
Tyr Leu Gln Met Asn Ser Leu Arg Ala Glu Asp Thr Ala Val Tyr Tyr
                85                  90                  95
Cys Ala Arg Asn Gly Ala Tyr Ala Gly Gly Pro Tyr Gly Asp Leu Trp
            100                 105                 110
Gly Gln Gly Thr Leu Val Thr Val Ser Gly Gly Gly Ser Gly Gly Gly
        115                 120                 125
Ser Gly Gly Gly Ser Gly Gly Ser Asp Ile Gln Met Thr Gln Ser
    130                 135                 140
Pro Ser Ser Leu Ser Ala Ser Val Gly Asp Arg Val Thr Ile Thr Cys
145                 150                 155                 160
Lys Ala Ser Gln Ser Ile Arg Thr Ser Leu Val Trp Tyr Gln Gln Lys
                165                 170                 175
Pro Gly Lys Ala Pro Lys Leu Leu Ile Tyr Lys Ala Ser Asp Leu Pro
            180                 185                 190
Ser Gly Val Pro Ser Arg Phe Ser Gly Ser Gly Ser Gly Thr Asp Phe
        195                 200                 205
Thr Leu Thr Ile Ser Ser Leu Gln Pro Glu Asp Phe Ala Thr Tyr Tyr
    210                 215                 220
Cys Gln Ser Tyr Asp Phe Arg Asp Thr Ile Asn Asn Gly His Ser Phe
225                 230                 235                 240
Gly Gln Gly Thr Lys Val Glu Ile Lys Gly Ser Gly Ser Ser Gly Gln
                245                 250                 255
Pro Arg Glu Pro Gln Val Tyr Thr Leu Pro Pro Ser Arg Glu Glu Met
            260                 265                 270
Thr Lys Asn Gln Val Ser Leu Thr Cys Leu Val Lys Gly Phe Tyr Pro
        275                 280                 285
Ser Asp Ile Ala Val Glu Trp Glu Ser Gln Gly Ser Pro Glu Asn Asn
    290                 295                 300
Tyr Lys Thr Thr Pro Pro Val Leu Asp Ser Asp Gly Ser Phe Phe Leu
305                 310                 315                 320
```

```
Tyr Ser Lys Leu Thr Val Asp Lys Ser Arg Trp Gln Gln Gly Asn Val
            325                 330                 335

Phe Ser Cys Ser Val Met His Glu Ala Leu His Asn His Tyr Thr Gln
            340                 345                 350

Lys Ser Leu Ser Leu Ser Pro Gly Ser Ser Ser Ser Ser Ser Ala Trp
            355                 360                 365

Ser His Pro Gln Phe Glu Lys
    370                 375

<210> SEQ ID NO 51
<211> LENGTH: 375
<212> TYPE: PRT
<213> ORGANISM: Artificial Sequence
<220> FEATURE:
<223> OTHER INFORMATION: MB_hu119_4C

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp His
            20                  25                  30

Tyr Trp Met Ser Trp Val Arg Gln Ala Pro Gly Lys Gly Leu Glu Trp
            35                  40                  45

Val Ser Ala Ile Tyr Thr Ala Asp Ser Asp Ser Tyr Tyr Ala Asp Ser
        50                  55                  60

Val Lys Gly Arg Phe Thr Ile Ser Lys Asp Ser Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asn Gly Ala Tyr Ala Gly Gly Pro Tyr Gly Asp Leu Trp
            100                 105                 110

Gly Gln Gly Thr Leu Val Thr Val Ser Gly Gly Gly Ser Gly Gly Gly
            115                 120                 125

Ser Gly Gly Gly Ser Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Gln Ser Ile Arg Thr Ser Leu Val Trp Tyr Gln Gln Lys
                165                 170                 175

Pro Gly Lys Ala Pro Lys Leu Leu Ile Tyr Lys Ala Ser Asp Leu Pro
            180                 185                 190

Ser Gly Val Pro Ser Arg Phe Ser Gly Ser Gly Ser Gly Thr Asp Phe
            195                 200                 205

Thr Leu Thr Ile Ser Ser Leu Gln Pro Glu Asp Phe Ala Thr Tyr Tyr
    210                 215                 220

Cys Gln Ser Tyr Asp Phe Arg Asp Thr Ile Asn Asn Gly His Ser Phe
225                 230                 235                 240

Gly Gln Gly Thr Lys Val Glu Ile Lys Gly Ser Gly Ser Ser Gly Gln
                245                 250                 255

Pro Arg Glu Pro Gln Val Tyr Thr Leu Pro Pro Ser Arg Glu Glu Met
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Gln Gly Ser Pro Glu Asn Asn
290                 295                 300
```

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
            325                 330                 335

Phe Ser Cys Ser Val Met His Glu Ala Leu His Asn His Tyr Thr Gln
            340                 345                 350

Lys Ser Leu Ser Leu Ser Pro Gly Ser Ser Ser Ser Ser Ala Trp
        355                 360                 365

Ser His Pro Gln Phe Glu Lys
    370                 375

<210> SEQ ID NO 52
<211> LENGTH: 20
<212> TYPE: PRT
<213> ORGANISM: Artificial Sequence
<220> FEATURE:
<223> OTHER INFORMATION: Signal Peptitde

<400> SEQUENCE: 52

Met Glu Thr Asp Thr Leu Leu Val Phe Val Leu Leu Val Trp Val Pro
1               5                   10                  15

Ala Gly Asn Gly
            20

<210> SEQ ID NO 53
<211> LENGTH: 119
<212> TYPE: PRT
<213> ORGANISM: Artificial Sequence
<220> FEATURE:
<223> OTHER INFORMATION: Human VH-template

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Val Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Val Gly Tyr Ser Leu Tyr Asp Tyr Trp Gly Gln Gly
            100                 105                 110

Thr Leu Val Thr Val Ser Ser
        115

<210> SEQ ID NO 54
<211> LENGTH: 107
<212> TYPE: PRT
<213> ORGANISM: Artificial Sequence
<220> FEATURE:
<223> OTHER INFORMATION: Human VL-template

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys
            100                 105

<210> SEQ ID NO 55
<211> LENGTH: 16
<212> TYPE: PRT
<213> ORGANISM: Artificial Sequence
<220> FEATURE:
<223> OTHER INFORMATION: (GGGS)4-linker

<400> SEQUENCE: 55

Gly Gly Gly Ser Gly Gly Gly Ser Gly Gly Gly Ser Gly Gly Gly Ser
1               5                   10                  15

<210> SEQ ID NO 56
<211> LENGTH: 111
<212> TYPE: PRT
<213> ORGANISM: Artificial Sequence
<220> FEATURE:
<223> OTHER INFORMATION: Minibody-scaffold

<400> SEQUENCE: 56

Gly Ser Gly Ser Ser Gly Gln Pro Arg Glu Pro Gln Val Tyr Thr Leu
1               5                   10                  15

Pro Pro Ser Arg Glu Glu Met Thr Lys Asn Gln Val Ser Leu Thr Cys
            20                  25                  30

Leu Val Lys Gly Phe Tyr Pro Ser Asp Ile Ala Val Glu Trp Glu Ser
        35                  40                  45

Gln Gly Ser Pro Glu Asn Asn Tyr Lys Thr Thr Pro Pro Val Leu Asp
50                  55                  60

Ser Asp Gly Ser Phe Phe Leu Tyr Ser Lys Leu Thr Val Asp Lys Ser
65                  70                  75                  80

Arg Trp Gln Gln Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 57
<211> LENGTH: 15
<212> TYPE: PRT
<213> ORGANISM: Artificial Sequence
<220> FEATURE:
<223> OTHER INFORMATION: Streptag II

<400> SEQUENCE: 57

Ser Ser Ser Ser Ser Ser Ala Trp Ser His Pro Gln Phe Glu Lys
1               5                   10                  15

```
<210> SEQ ID NO 58
<211> LENGTH: 106
<212> TYPE: PRT
<213> ORGANISM: Artificial Sequence
<220> FEATURE:
<223> OTHER INFORMATION: Human kappa light chain constant domain
      scaffold

<400> SEQUENCE: 58

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 59
<211> LENGTH: 330
<212> TYPE: PRT
<213> ORGANISM: Artificial Sequence
<220> FEATURE:
<223> OTHER INFORMATION: Human IGG1 heavy chain CH1CH2CH3-scaffold

<400> SEQUENCE: 59

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ser Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 60
<211> LENGTH: 330
<212> TYPE: PRT
<213> ORGANISM: Artificial Sequence
<220> FEATURE:
<223> OTHER INFORMATION: Human IGG1 heavy chain CH1CH2(N297S)CH3-
      scaffold

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ser Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

-continued

```
Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```